US010000767B2

(12) United States Patent
Crawford et al.

(10) Patent No.: US 10,000,767 B2
(45) Date of Patent: Jun. 19, 2018

(54) METHODS AND COMPOSITIONS FOR PLANT PEST CONTROL

(71) Applicant: Monsanto Technology LLC, St. Louis, MO (US)

(72) Inventors: Michael J. Crawford, St. Louis, MO (US); Xiangqian Li, Chesterfield, MO (US); Mahak Kapoor, Creve Coeur, MO (US); Deryck Jeremy Williams, University City, MO (US)

(73) Assignee: Monsanto Technology LLC, St. Louis, MO (US)

( * ) Notice: Subject to any disclaimer, the term of this patent is extended or adjusted under 35 U.S.C. 154(b) by 786 days.

(21) Appl. No.: 14/165,097

(22) Filed: Jan. 27, 2014

(65) Prior Publication Data
US 2014/0215656 A1 Jul. 31, 2014

Related U.S. Application Data

(60) Provisional application No. 61/757,291, filed on Jan. 28, 2013.

(51) Int. Cl.
*C12N 15/82* (2006.01)
*A01H 1/00* (2006.01)
*C07K 14/415* (2006.01)
*A01N 65/00* (2009.01)
*A01N 63/02* (2006.01)
*A01N 63/04* (2006.01)
*A01N 37/46* (2006.01)

(52) U.S. Cl.
CPC ........... *C12N 15/8285* (2013.01); *A01H 1/00* (2013.01); *A01N 65/00* (2013.01); *C07K 14/415* (2013.01); *C12N 15/8206* (2013.01); *C12N 15/8218* (2013.01); *A01N 37/46* (2013.01); *A01N 63/02* (2013.01); *A01N 63/04* (2013.01); *C12N 15/8282* (2013.01); *Y02A 50/351* (2018.01)

(58) Field of Classification Search
CPC ............ C12N 15/8282; C12N 15/8206; C12N 15/8218; C12N 15/8286; C12N 2310/14; A01N 37/46; A01N 65/00; C07K 14/415
See application file for complete search history.

(56) References Cited

U.S. PATENT DOCUMENTS

| | | | |
|---|---|---|---|
| 3,687,808 A | 8/1972 | Alice De et al. |
| 3,850,752 A | 11/1974 | Schuurs et al. |
| 3,935,074 A | 1/1976 | Rubenstein et al. |
| 4,023,525 A | 5/1977 | Weber |
| 4,079,696 A | 3/1978 | Weber |
| 4,476,301 A | 10/1984 | Imbach et al. |
| 4,535,060 A | 8/1985 | Comai |
| 4,581,847 A | 4/1986 | Hibberd et al. |
| 4,761,373 A | 8/1988 | Anderson et al. |
| 4,769,061 A | 9/1988 | Comai |
| 4,810,648 A | 3/1989 | Stalker |
| 4,940,835 A | 7/1990 | Shah et al. |
| 4,971,908 A | 11/1990 | Kishore et al. |
| 5,004,863 A | 4/1991 | Umbeck |
| 5,013,659 A | 5/1991 | Bedbrook et al. |
| 5,015,580 A | 5/1991 | Christou et al. |
| 5,023,243 A | 6/1991 | Tullis |
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,562 A | 11/1993 | Matteucci |
| 5,264,564 A | 11/1993 | Matteucci |
| 5,304,732 A | 4/1994 | Anderson et al. |
| 5,310,667 A | 5/1994 | Eichholtz et al. |
| 5,312,910 A | 5/1994 | Kishore et al. |
| 5,331,107 A | 7/1994 | Anderson et al. |
| 5,378,824 A | 1/1995 | Bedbrook et al. |

(Continued)

FOREIGN PATENT DOCUMENTS

| | | | | |
|---|---|---|---|---|
| CN | 101914540 | | 12/2010 | |
| CN | 101914540 A | * | 12/2010 | ........... C12N 15/113 |

(Continued)

OTHER PUBLICATIONS

Eichmann, Ruth, et al. "The barley apoptosis suppressor homologue BAX inhibitor-1 compromises nonhost penetration resistance of barley to the inappropriate pathogen *Blumeria graminis* f. sp. tritici." Molecular plant-microbe interactions 17.5 (2004): 484-490.*
Sun, Chuanxin, et al. "Antisense oligodeoxynucleotide inhibition as a potent strategy in plant biology: identification of SUSIBA2 as a transcriptional activator in plant sugar signalling." The Plant Journal 44.1 (2005): 128-138.*
McMullen, M., et al, "Effects of application parameters on control of Fusarium head blight with fungicides." Proc. 2000 National Fusarium Head Blight Forum. RW Ward, SM Canty, J. Lewis, and L. Siler, eds. Erlanger, KY. 2000.*
Liu et al., "Insecticidal Activity of Surfactants and Oils Against Silverleaf Whitefly (*Bemisia argentifolii*) Nymphs (*Homoptera: aleyrodidae*) on Collards and Tomato", Pest Management Science, 2000, pp. 861-866, vol. 56.

(Continued)

*Primary Examiner* — Lee A Visone
*Assistant Examiner* — Weihua Fan
(74) *Attorney, Agent, or Firm* — Thompson Coburn LLP; William A. Holtz; Amanda J. Carmany-Rampey

(57) ABSTRACT

Provided are methods and compositions to improve fungal disease resistance in various crop plants. Also provided are combinations of compositions and methods to improve fungal disease resistance in various crop plants.

5 Claims, 2 Drawing Sheets

(56) References Cited

U.S. PATENT DOCUMENTS

| | | |
|---|---|---|
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,463,174 A | 10/1995 | Moloney et al. |
| 5,463,175 A | 10/1995 | Barry et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,519,126 A | 5/1996 | Hecht |
| 5,536,821 A | 7/1996 | Agrawal et al. |
| 5,538,880 A | 7/1996 | Lundquist et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,866,775 A | 2/1999 | Eichholtz et al. |
| 5,874,265 A | 2/1999 | Adams et al. |
| 5,876,739 A | 3/1999 | Turnblad et al. |
| 5,879,903 A | 3/1999 | Strauch et al. |
| 5,891,246 A | 4/1999 | Lund |
| 5,914,451 A | 6/1999 | Martinell et al. |
| 5,919,675 A | 7/1999 | Adams et al. |
| 5,922,602 A | 7/1999 | Kumagai et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A * | 11/1999 | Sandbrink ............. A01N 25/00 424/405 |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,225,105 B1 | 5/2001 | Sathasivan et al. |
| 6,225,114 B1 | 5/2001 | Eichholtz et al. |
| 6,245,968 B1 | 6/2001 | Boudec et al. |
| 6,248,876 B1 | 6/2001 | Barry et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,453,609 B1 | 9/2002 | Soll et al. |
| 6,506,559 B1 | 1/2003 | Fire et al. |
| 6,582,516 B1 | 6/2003 | Carlson |
| 6,635,805 B1 | 10/2003 | Baulcombe et al. |
| 6,644,341 B1 | 11/2003 | Chemo et al. |
| 6,768,044 B1 | 7/2004 | Boudec et al. |
| 6,800,748 B2 | 10/2004 | Holzberg et al. |
| 6,870,075 B1 | 3/2005 | Beetham et al. |
| 6,992,237 B1 | 1/2006 | Habben et al. |
| 7,022,896 B1 | 4/2006 | Weeks et al. |
| 7,026,528 B2 | 4/2006 | Cheng et al. |
| RE39,247 E | 8/2006 | Barry et al. |
| 7,105,724 B2 | 9/2006 | Weeks et al. |
| 7,122,719 B2 | 10/2006 | Hakimi et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,405,347 B2 | 7/2008 | Hammer et al. |
| 7,406,981 B2 | 8/2008 | Hemo et al. |
| 7,485,777 B2 | 2/2009 | Nakajima et al. |
| 7,525,013 B2 | 4/2009 | Hildebrand et al. |
| 7,622,301 B2 | 11/2009 | Ren et al. |
| 7,671,254 B2 | 3/2010 | Tranel et al. |
| 7,714,188 B2 | 5/2010 | Castle et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,143,480 B2 | 3/2012 | Axtell et al. |
| 8,642,505 B2 | 2/2014 | Kohn |
| 9,121,022 B2 | 9/2015 | Sammons et al. |
| 9,422,557 B2 | 8/2016 | Ader et al. |
| 2001/0042257 A1 | 11/2001 | Connor-Ward et al. |
| 2002/0114784 A1 | 8/2002 | Li et al. |
| 2003/0150017 A1 | 8/2003 | Mesa et al. |
| 2003/0167537 A1 | 9/2003 | Jiang |
| 2003/0235916 A1 | 12/2003 | Monahan et al. |
| 2004/0053289 A1 | 3/2004 | Christian et al. |
| 2004/0055041 A1 | 3/2004 | Labate et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0244075 A1 | 12/2004 | Cai et al. |
| 2005/0026290 A1 | 2/2005 | Ciardi et al. |
| 2005/0239728 A1 | 10/2005 | Pachuk et al. |
| 2006/0021087 A1 | 1/2006 | Baum et al. |

(56) References Cited

U.S. PATENT DOCUMENTS

| | | | |
|---|---|---|---|
| 2006/0064775 A1* | 3/2006 | Frank | C07K 14/415 800/279 |
| 2006/0111241 A1 | 5/2006 | Gerwick et al. | |
| 2006/0130172 A1 | 6/2006 | Whaley et al. | |
| 2006/0135758 A1 | 6/2006 | Wu | |
| 2006/0200878 A1 | 9/2006 | Lutfiyya et al. | |
| 2006/0247197 A1 | 11/2006 | Van De Craen et al. | |
| 2006/0272049 A1 | 11/2006 | Waterhouse et al. | |
| 2006/0276339 A1 | 12/2006 | Windsor et al. | |
| 2007/0011775 A1 | 1/2007 | Allen et al. | |
| 2007/0050863 A1 | 3/2007 | Tranel et al. | |
| 2007/0124836 A1 | 5/2007 | Baum et al. | |
| 2007/0199095 A1 | 8/2007 | Allen et al. | |
| 2007/0250947 A1 | 10/2007 | Boukharov et al. | |
| 2007/0259785 A1 | 11/2007 | Heck et al. | |
| 2007/0281900 A1 | 12/2007 | Cui et al. | |
| 2007/0300329 A1 | 12/2007 | Allen et al. | |
| 2008/0022423 A1 | 1/2008 | Roberts et al. | |
| 2008/0050342 A1 | 2/2008 | Fire et al. | |
| 2008/0092256 A1 | 4/2008 | Kohn | |
| 2008/0155716 A1 | 6/2008 | Sonnewald et al. | |
| 2008/0214443 A1 | 9/2008 | Baum et al. | |
| 2009/0011934 A1 | 1/2009 | Zawierucha et al. | |
| 2009/0018016 A1 | 1/2009 | Duck et al. | |
| 2009/0098614 A1 | 4/2009 | Zamore et al. | |
| 2009/0137395 A1 | 5/2009 | Chicoine et al. | |
| 2009/0165153 A1 | 6/2009 | Wang et al. | |
| 2009/0165166 A1 | 6/2009 | Feng et al. | |
| 2009/0188005 A1 | 7/2009 | Boukharov et al. | |
| 2009/0205079 A1 | 8/2009 | Kumar et al. | |
| 2009/0293148 A1 | 11/2009 | Ren et al. | |
| 2009/0307803 A1 | 12/2009 | Baum et al. | |
| 2010/0005551 A1 | 1/2010 | Roberts et al. | |
| 2010/0068172 A1 | 3/2010 | Van De Craen | |
| 2010/0071088 A1 | 3/2010 | Sela et al. | |
| 2010/0100988 A1 | 4/2010 | Tranel et al. | |
| 2010/0122381 A1 | 5/2010 | Buehler et al. | |
| 2010/0154083 A1 | 6/2010 | Ross et al. | |
| 2010/0247578 A1 | 9/2010 | Salama | |
| 2011/0035836 A1 | 2/2011 | Eudes et al. | |
| 2011/0098180 A1 | 4/2011 | Michel et al. | |
| 2011/0105327 A1 | 5/2011 | Nelson | |
| 2011/0126310 A1 | 5/2011 | Feng et al. | |
| 2011/0126311 A1 | 5/2011 | Velcheva et al. | |
| 2011/0152346 A1 | 6/2011 | Karleson et al. | |
| 2011/0152353 A1 | 6/2011 | Koizumi et al. | |
| 2011/0160082 A1 | 6/2011 | Woo et al. | |
| 2011/0166022 A1 | 7/2011 | Israels et al. | |
| 2011/0166023 A1 | 7/2011 | Nettleton-Hammond et al. | |
| 2011/0171287 A1 | 7/2011 | Saarma et al. | |
| 2011/0177949 A1 | 7/2011 | Krapp et al. | |
| 2011/0185444 A1 | 7/2011 | Li et al. | |
| 2011/0185445 A1 | 7/2011 | Bogner et al. | |
| 2011/0191897 A1 | 8/2011 | Poree et al. | |
| 2011/0296555 A1 | 12/2011 | Ivashuta et al. | |
| 2011/0296556 A1* | 12/2011 | Sammons | A01N 63/02 800/298 |
| 2012/0036594 A1 | 2/2012 | Cardoza et al. | |
| 2012/0137387 A1 | 5/2012 | Baum et al. | |
| 2012/0156784 A1 | 6/2012 | Adams, Jr. et al. | |
| 2012/0159672 A1 | 6/2012 | Alexandrov et al. | |
| 2012/0164205 A1 | 6/2012 | Baum et al. | |
| 2012/0185967 A1 | 7/2012 | Sela et al. | |
| 2013/0003213 A1 | 1/2013 | Kabelac et al. | |
| 2013/0041004 A1 | 2/2013 | Drager et al. | |
| 2013/0047297 A1 | 2/2013 | Sammons et al. | |
| 2013/0067618 A1 | 3/2013 | Ader et al. | |
| 2013/0096073 A1 | 4/2013 | Sidelman | |
| 2013/0097726 A1 | 4/2013 | Ader et al. | |
| 2013/0212739 A1 | 8/2013 | Giritch et al. | |
| 2013/0247247 A1 | 9/2013 | Ader et al. | |
| 2013/0254940 A1 | 9/2013 | Ader et al. | |
| 2013/0254941 A1 | 9/2013 | Ader et al. | |
| 2013/0288895 A1 | 10/2013 | Ader et al. | |
| 2013/0318657 A1 | 11/2013 | Avniel et al. | |
| 2013/0318658 A1 | 11/2013 | Ader et al. | |
| 2013/0326731 A1 | 12/2013 | Ader et al. | |
| 2014/0018241 A1 | 1/2014 | Sammons et al. | |
| 2014/0057789 A1 | 2/2014 | Sammons et al. | |
| 2014/0109258 A1 | 4/2014 | Van De Craen et al. | |
| 2014/0215656 A1 | 7/2014 | Crawford et al. | |
| 2014/0230090 A1 | 8/2014 | Avniel et al. | |
| 2014/0274712 A1 | 9/2014 | Finnessy et al. | |
| 2014/0283211 A1 | 9/2014 | Crawford et al. | |
| 2014/0296503 A1 | 10/2014 | Avniel et al. | |
| 2015/0247153 A1 | 9/2015 | Fillatti et al. | |

FOREIGN PATENT DOCUMENTS

| | | |
|---|---|---|
| EP | 1416049 A1 | 5/2004 |
| EP | 2 530 159 A1 | 12/2012 |
| JP | 2006343473 A | 12/2006 |
| WO | 1989/11789 A1 | 12/1989 |
| WO | 94/03607 A1 | 2/1994 |
| WO | 1996/005721 A1 | 2/1996 |
| WO | 1996/033270 A1 | 10/1996 |
| WO | 1996/038567 A2 | 12/1996 |
| WO | 1996/040964 A2 | 12/1996 |
| WO | 1999/024585 A1 | 5/1999 |
| WO | 99/32619 A1 | 7/1999 |
| WO | 1999/32619 A1 | 7/1999 |
| WO | 99/67367 A1 | 12/1999 |
| WO | 1999/61631 A1 | 12/1999 |
| WO | 00/32757 A2 | 6/2000 |
| WO | 2000/044914 A1 | 8/2000 |
| WO | 2001/007596 A1 | 2/2001 |
| WO | 2002/14472 A2 | 2/2002 |
| WO | 2003/106636 A2 | 12/2003 |
| WO | 2004/005485 A2 | 1/2004 |
| WO | 2004/009761 A2 | 1/2004 |
| WO | 20041022771 A2 | 3/2004 |
| WO | 2004/074443 A2 | 9/2004 |
| WO | 2005/003362 A2 | 1/2005 |
| WO | 2005/007860 | 1/2005 |
| WO | 2005/107437 A2 | 11/2005 |
| WO | 2005/110068 A2 | 11/2005 |
| WO | 2006/074400 A2 | 7/2006 |
| WO | 2006/138638 A1 | 12/2006 |
| WO | 2007/007316 A1 | 1/2007 |
| WO | 2007/035650 A2 | 3/2007 |
| WO | 2007/039454 A1 | 4/2007 |
| WO | 2007/051462 A2 | 5/2007 |
| WO | 2007/070389 A2 | 6/2007 |
| WO | 2007/074405 A2 | 7/2007 |
| WO | 2007/080126 A2 | 7/2007 |
| WO | 2007/080127 A2 | 7/2007 |
| WO | 2008/007100 A2 | 1/2008 |
| WO | 2008/063203 A2 | 5/2008 |
| WO | 2008/148223 A1 | 12/2008 |
| WO | 2009/046384 A1 | 4/2009 |
| WO | 2009/116558 A1 | 9/2009 |
| WO | 2009/125401 A2 | 10/2009 |
| WO | 2010/078912 A1 | 7/2010 |
| WO | 2010/083179 A2 | 7/2010 |
| WO | 2010/104217 A2 | 9/2010 |
| WO | 2010/108611 A1 | 9/2010 |
| WO | 2010/112826 A2 | 10/2010 |
| WO | 2010/116122 A2 | 10/2010 |
| WO | 2010/119906 A1 | 10/2010 |
| WO | 2010/130970 A1 | 11/2010 |
| WO | 2011/001434 A1 | 1/2011 |
| WO | 2011/003776 A2 | 1/2011 |
| WO | 2011/067745 A2 | 6/2011 |
| WO | 2011/080674 A2 | 7/2011 |
| WO | 2011/112570 A1 | 9/2011 |
| WO | 2011/132127 A1 | 10/2011 |
| WO | 2012/001626 A1 | 1/2012 |
| WO | 2012/056401 A1 | 5/2012 |
| WO | 2012/092580 A2 | 7/2012 |
| WO | 2013/010691 A1 | 1/2013 |
| WO | 2013/025670 A1 | 2/2013 |
| WO | 2013/039990 A1 | 3/2013 |
| WO | 2013/040005 A1 | 3/2013 |
| WO | 2013/040021 A1 | 3/2013 |

(56) References Cited

FOREIGN PATENT DOCUMENTS

| | | |
|---|---|---|
| WO | 2013/040033 A1 | 3/2013 |
| WO | 2013/040049 A1 | 3/2013 |
| WO | 2013/040057 A1 | 3/2013 |
| WO | 2013/040116 A9 | 3/2013 |
| WO | 2013/040117 A1 | 3/2013 |
| WO | 2013/040117 A9 | 6/2013 |
| WO | 2013/175480 A1 | 11/2013 |
| WO | 2014/106837 A2 | 7/2014 |
| WO | 2014/106838 A2 | 7/2014 |
| WO | 2014/151255 A1 | 9/2014 |
| WO | 2014/164761 A1 | 10/2014 |
| WO | 2014/164797 A1 | 10/2014 |
| WO | 2015/010026 A2 | 1/2015 |

OTHER PUBLICATIONS

Chen et al., "Transfection and Expression of Plasmid DNA in Plant Cells by Arginine-Rich Intracellular Delivery Peptide Without Protoplast Preparation", Federation of European Biochemical Societies Letters, 2007, pp. 1891-1897, vol. 581.
Kim et al., "Optimization of Conditions for Transient Agrobacterium-Mediated Gene Expression Assays in Arabidopsis", Plant Cell Reproduction, 2009, pp. 1159-1167, vol. 28.
Thomas et al., "Size Constraints for Targeting Post-Transcriptional Gene Silencing and for RNA-Directed Methylation in Nicotiana Benthamiana using a Potato Virus X Vector", The Plant Journal, 2001, pp. 417-425, vol. 25 No. 4.
"Agricultural Chemical Usage 2006 Vegetables Summary", Agricultural Statistics Board, Jul. 2007, pp. 1-372.
Kirkwood, "Herbicides and Plants", Botanical Journal of Scotland, Jan. 1, 1993, pp. 447-462, vol. 46 Issue 3.
Kusaba, "RNA interference in crop plants", Current Opinion in Biotechnology, 15(2):139-143 (2004).
Li et al., "The FAST technique: a simplified Agrobacterium-based transformation method for transient gene expression analysis in seedlings of *Arabidopsis* and other plant species", Plant Methods, 5(6):1-15 (2009).
Office Action for U.S. Appl. No. 13/612,985 dated Nov. 10, 2015.
Orbovic et al., "Foliar-Applied Surfactants and Urea Temporarily Reduce Carbon Assimilation of Grapefruit Leaves", Journal of the American Society for Horticultural Science, 2001, pp. 486-490, vol. 126(4).
Showalter, "Structure and Function of Plant Cell Wall Proteins", The Plant Cell, Jan. 1993, pp. 9-23, vol. 5.
Stevens et al., "New Formulation Technology—SilWet® Organosilicone Surfactants Have Physical and Physiological Properties Which Enhance the Performance of Sprays", Proceedings of the 9th Australian Weeds Conference, pp. 327-331 (1990).
Stevens, "Organosilicone Surfactants as Adjuvants for Agrochemicals", Pestic. Sci., 1993, pp. 103-122, vol. 38.
Stock et al., "Possible Mechanisms for Surfactant-Induced Foliar Uptake of Agrochemicals", Pesticide Science, 1993, pp. 165-177, vol. 38.
Zhang et al., "Cationic Lipids and Polymers Mediated Vectors for Delivery of siRNA", Journal of Controlled Release, Oct. 18, 2007, pp. 1-10, vol. 123 Issue. 1.
Office Action for U.S. Appl. No. 13/619,980 dated Apr. 7, 2016.
Schweizer et al., "Double-stranded RNA interferes with gene function at the single-cell level in cereals", The Plant Journal, 2000, pp. 895-903, vol. 24, No. 6.
Jones-Rhoades et al., "MicroRNAs and Their Regulatory Roles in Plants", Annual Review of Plant Biology, 2006, pp. 19-53, vol. 57.
Reynolds et al "Rational siRNA Design for RNA Interference", Nature Biotechnology, Mar. 2004, pp. 326-330, vol. 22 No. 3.
Pei et al., "On the Art of Identifying Effective and Specific siRNAs", Nature Methods, 2006, pp. 670-676, vol. 3 No. 9.
Zhang et al., "Agrobacterium-Mediated Transformation of Arabidopsis Thaliana Using the Floral Dip Method", Nature Protocols, 2006, pp. 641-646, vol. 1 No. 2.
Brodersen et al., "The Diversity of RNA Silencing Pathways in Plants", TRENDS in Genetics, May 2006, pp. 268-280, vol. 22 No. 5.
Tomari et al., "Perspective: Machines for RNAi", Genes and Development, 2005, pp. 517-529, vol. 19.
Vaucheret, "Post-Transcriptional Small RNA Pathways in Plants: Mechanisms and Regulations", Genes and Development, 2006, pp. 759-771, vol. 20.
Meins et al., "RNA Silencing Systems and their Relevance to Plant Development", Annual Reviews—Cell and Developmental Biology, Nov. 2005, pp. 297-318, vol. 21.
Hamilton et al., "Two Classes of Short Interfering RNA in RNA Silencing" The EMBO Journal, Sep. 2, 2002, pp. 4671-4679, vol. 21 No. 17.
Du et al, "A Systematic Analysis of the Silencing Effects of an Active siRNA at All Single-nucleotide Mismatched Target Sites", Nucleic Acids Research, 2005, pp. 1671-1677, vol. 33 No. 5.
Concise Descriptions of Relevance filed by a third party on Nov. 29, 2012 in U.S. Appl. No. 13/042,856.
Hunter et al., "RNA Interference Strategy to Suppress Psyllids and Leafhoppers" International Plant and Animal Genome XIX, Jan. 15-19, 2011.
International Search Report and Written Opinion for PCT/US2011/027528 dated May 10, 2011.
Gan et al., "Bacterially Expressed dsRNA Protects Maize Against SCMV Infection", Plant Cell Reports, 2010, pp. 1261-1268, vol. 11.
Tenllado et al., "Crude Extracts of Bacterially Expressed dsRNA Can be Used to Protect Plants Against Virus Infection", BMC Biotechnology, 2003, pp. 1-11, vol. 3 No. 3.
Sun et al., "Antisense Oligodeoxynucleotide Inhibition as a Potent Strategy in Plant Biology: Identification of SUSIBA2 as a Transcriptional Activator in Plant Sugar Signalling", The Plant Journal, 2005, pp. 128-138, vol. 44.
Baulcombe et al., "RNA Silencing and Heritable Epigenetic Effects in Tomato and Arabidopsis", Abstract 13th Annual Fall Symposium, Plant Genomes to Phenomes, Donal Danforth Plant Science, Sep. 28-30, 2011.
Himber et al., "Transitivity-Dependent and -Independent Cell-to-Cell Movement of RNA Silencing", The EMBO Journal, 2003, pp. 4523-4533, vol. 22 No. 17.
Ryabov et al., "Cell-to-Cell, but Not Long-Distance, Spread of RNA Silencing That is Induced in Individual Epidermal Cells", Journal of Virology, 2004, pp. 3149-3154, vol. 78 No. 6.
COST Action FA0806 Progress Report "Plant Virus Control Employing RNA-Based Vaccines: A Novel Non-Transgenic Strategy", 2010.
Clough, "Floral Dip: A Simplified Method for Agrobacterium-Mediated Transformation of Arabidopsis Thaliana", The Plant Journal, 1998, pp. 735-743, vol. 16 No. 6.
Nowak et al., "A new and efficient method for inhibition of RNA viruses by DNA interference", The FEBS Journal, 2009, pp. 4372-4380, vol. 276.
Klahre et al., "High Molecular Weight RNAs and Small Interfering RNAs Induce Systemic Posttranscriptional Gene Silencing in Plants", Proceedings of the National Academy of Sciences, 2002, pp. 11981-11986, vol. 99 No. 18.
Liu et al., "Comparative study on the interaction of DNA with three different kinds of surfactants and the formation of multilayer films", Bioelectrochemistry, 2007, pp. 301-307, vol. 70.
Melnyk et al., "Intercellular and systemic movement of RNA silencing signals", The EMBO Journal, 2011, pp. 3553-3563, vol. 30.
Reddy et al., "Organosilicone Adjuvants Increased the Efficacy of Glyphosate for Control of Weeds in Citrus (*Citrus* spp.)", HortScience, 1992, pp. 1003-1005, vol. 27 No. 9.
Zhu et al., "Ingested RNA Interference for Managing the Populations of the Colorado Potato Beetle, Liptinotarsa Decemlineata", Pest Management Science, 2010, pp. 175-182, vol. 67.
Maas et al., "Mechanism and optimized conditions for PEG mediated DNA transfection into plant protoplasts", Plant Cell Reports, 1989, pp. 148-151, vol. 8.

(56) References Cited

OTHER PUBLICATIONS

Wardfell, "Floral Activity in Solutions of Deoxyribonucleic Acid Extracted from Tobacco Stems", Plant Physiology, 1976, pp. 855-861, vol. 57.
Wardell, "Floral Induction of Vegetative Plants Supplied a Purified Fraction of Deoxyribonucleic Acid from Stems of Flowering Plants", Plant Physiology, 1977, pp. 885/891, vol. 60.
Hewezi et al., "Local infiltration of high- and low-molecular-weight RNA from silenced sunflower (*Helianthus annuus* L.) plants triggers post-transcriptional gene silencing in non-silenced plants", Plant Biotechnology Journal, 2005, pp. 81-89, vol. 3.
Zhao et al., "Phyllotreta Striolata (Coleoptera: Chrysomelidae): Arginine Kinase Cloning and RNAi-Based Pest Control", European Journal of Entomology, 2008, pp. 815-822, vol. 105 No. 5.
Hannon, "RNA Interference", Nature Publishing Group, 2002, pp. 244-251, vol. 481.
Tenllado et al., "RNA Interference as a New Biotechnological Tool for the Control of Virus Diseases in Plants", Virus Research, 2004, pp. 85-96, vol. 102.
Gong et al., "Silencing of Rieske Iron-Sulfur Protein Using Chemically Synthesised siRNA as a Potential Biopesticide Against Plutella Xylostella" Pest Management Science, 2011, pp. 514-520, vol. 67.
Dunoyer et al., "Small RNA Duplexes Function as Mobile Silencing Signals Between Plant Cells", Science, 2010, pp. 912-916, vol. 328.
Molnar et al., "Small Silencing RNAs in Plants are Mobile and Direct Epigenetic Modification in Recipient Cells", Science, 2010, pp. 872-875, vol. 328.
Sun et al., "Sweet Delivery—Sugar Translocators as Ports of Entry for Antisense Oligodeoxynucleotides in Plant Cells", The Plant Journal, 2007, pp. 1192-1198, vol. 52.
Vionnet et al., "Systemic Spread of Sequence-Specific Transgene RNA Degradation in Plants is Initiated by Localized Introduction of Ectopic Promoterless DNA", Cell, 1998, pp. 177-187, vol. 95.
An et al., "Transient RNAi Induction Against Endogenous Genes in Arabidopsis Protoplasts Using in Vitro-Prepared Double-Stranded RNA", Bioscience, Biotechnology and Biochemistry, 2005, pp. 415/418, vol. 69 No. 2.
Artymovich, "Using RNA Interference to Increase Crop Yield and Decrease Pest Damage", MMG 445 Basic Biotechnology, 2009, pp. 7-12, vol. 5 No. 1.
Li et al., "The FAST technique: a simplified Agrobacterium-based transformation method for transient gene expression analysis in seedlings of *Arabidopsis* and other plant species", Plant Methods, 2009, vol. 5 No. 6.
Paungfoo-Lonhienne et al., "The DNA is Taken Up by Root Hairs and Pollen, and Stimulates Root and Pollen Tube Growth", Plant Physiology, 2010, pp. 799-805, vol. 153.
Paungfoo-Lonhienne et al., "DNA Uptake by Arabidopsis Induces Changes in the Expression of CLE Peptides Which Control Root Morphology", Plant Signaling and Behavior, 2010, pp. 1112-1114, vol. 5 No. 9.
International Preliminary Report on Patentability for PCT/US2011/027528 dated Sep. 9, 2011.
Gaines et al., "Gene Amplification Confers Glyphosate Resistance in Amaranthus Palmeri", PNAS, 2010, pp. 1029-1034, vol. 107 No. 3.
Kirkwood, "Use and Mode of Action of Adjuvants for Herbicides: A Review of Some Current Work", Pest Management Science, 1993, pp. 93-102, vol. 3.
Kusaba et al., "Low Glutelin Content1: A Dominant Mutation that Suppresses the Glutelin Multigene Family via RNA Silencing in Rice", The Plant Cell, Jun. 2003, pp. 1455-1467, vol. 15 No. 6.
Unnamalai, "Cationic Oligopeptide-Mediated Delivery of dsRNA for Post-Transcriptional Gene Silencing in Plant Cells", FEBS Letters, May 21, 2004, pp. 307-310, vol. 566 No. 1.
Al-Kaff et al., "Plants Rendered Herbicide-Susceptible by Cauliflower Mosaicviurs-Elicited Suppression of a 35S Promoter-Regulated Transgene", Nature Biotechnology, Sep. 2000, pp. 995-999, vol. 18 No. 9.

Gao et al., "Nonviral Methods for siRNA Delivery", Molecular Pharmaceutics, Dec. 30, 2008, pp. 651-658, vol. 6 No. 3.
Busch et al., "RNAi for Discovery of Novel Cropproection Products", Pflanzenchutz-Nachrichten Bayer, 2005, pp. 34-50, vol. 58 No. 1.
Roberts, "Fast-Track Applications: The Potential for Direct Delivery of Proteins and Nucleic Acids to Plant Cells for the Discovery of Gene Function", Plant Methods, Dec. 15, 2005, pp. 1-3, vol. 1 No. 12.
Basu et al., "Weed Genomics: New Tools to Understand Weed Biology", Trends in Plant Science, Jul. 17, 2004, pp. 391-398, vol. 9 No. 8.
Tenllado et al., "Double-Stranded RNA-Mediated Interference with Plant Virus Infection", Journal of Virology, Dec. 2001, pp. 12288-12297, vol. 75 No. 24.
Bart, "A Novel System for Gene Silencing Using siRNAs in Rice Leaf and Stem-Derived Protoplasts", Plant Methods, Jun. 29, 2006, pp. 13, No. 2.
Fraley et al., "Liposome-Mediated Delivery of Tobacco Mosaic Virus RNA into Tobacco Protoplasts: A Sensitive Assay for Monitoring Liposome-Protoplast Interactions", Proceedings of the National Academy of Sciences of the United States of America, Mar. 1982, pp. 1859-1863, vol. 79.
Tang et al., "Efficient Delivery of Small Interfering RNA to Plant Cells by a Nanosecond Pulsed Laser-Induced Stress Wave for Posttranscriptional Gene Silencing", Plant Science, May 15, 2006, pp. 375-381, vol. 171.
Waterhouse et al., "Exploring Plant Genomes by RNA-Induced Gene Silencing" Nature Reviews—Genetics, Jan. 2003, pp. 29-38, vol. 4.
Office Action for NZ Application 601784 dated Apr. 23, 2013.
YouTube video by General Electric Company "Silwet Surfactants," screen shot taken on Jan. 11, 2012 of video of www.youtube_com/watch?v=WBw7nXMoHk8 (uploaded Jul. 13, 2009).
Silwet L-77 Spray Adjuvant for agricultural applications, product description from Momentive Performance Materials, Inc.
European Cooperation in the field of Scientific and Technical Research—Memorandum of Understanding for Cost Action FA0806 (2008).
Devgen "The mini-Monsanto" KBC Securities (2006).
Eichmann et al., "BAX Inhibitor-1 Is Required for Full Susceptibility of Barley to Powdery Mildew", Molecular Plant-Microbe Interactions, 2010, pp. 1217-1227, vol. 23 No. 9.
Huckelhoven et al, "Overexpression of Barley BAX Inhibitor 1 Induces Breakdown of mlo-Mediated Penetration Resistance to Blumeria Graminis", Proceedings of the National Academy of Sciences, Apr. 29, 2003, pp. 5555-5560, vol. 100 No. 9.
Watanabe et al., "BAX Inhibitor-1, a Conserved Cell Death Suppressor, Is a Key Molecular Switch Downstream from a Variety of Biotic and Abiotic Stress Signals in Plants", International Journal of Molecular Sciences, Jul. 10, 2009, pp. 3149-3167, vol. 10.
Alakouras et al., "Induction of Silencing in Plants by High-Pressure Spraying of in vitro-Synthesized Small RNAs", Frontiers in Plant Science, Aug. 2016, pp. 1-5, vol. 7, No. 1327.
Hsieh et al., "A library of siRNA duplexes targeting the phosphoinositide 3-kinase pathway: determinants of gene silencing for usein cell-based screens," Nucleic Acids Res., 32(3):893-901 (2004).
Isaacs et al., "Engineered riboregulators enable post-transcriptional control of gene expression," Nature Biotechnology, ?2(7):841-847 (2004).
Kertbundit et al., "In vivo random β-glucuronidase gene fusions in *Arabidopsis thaliana*," Proc. Natl. Acad. Sci. U S A., 38:5212-5216 (1991).
Khachigian, "DNAzymes: Cutting a path to a new class of therapeutics," Cuff Opin Mol Ther 4(2):119-121 (2002).
Leopold et al., "Chapter 4: Moisture as a Regulator of Physiological Reaction in Seeds," Seed Moisture, CSSA Special Publication No. 14, pp. 51-69 (1989).
Lu et al., "OligoWalk: an online siRNA design tool utilizing hybridization thermodynamics," Nucleic Acids Research, 36:W104-W108 (2008).

(56) References Cited

OTHER PUBLICATIONS

Mackenzie et al., "Transgenic Nicotiana Debneyii Expressing Viral Coat Protein Are Resistant to Potato Virus S Infection," Journal of General Virology, 71:2167-2170 (1990).
Molina et al., "Inhibition of Protoporphyrinogen Oxidase Expression in Arabidopsis Causes a Lesion-Mimic Phenotype That Induces Systemic Acquired Resistance," The Plant Journal, 1 7(6):667-678 (1999).
Office Action dated Nov. 19, 2014, in Eurasian Patent Application No. 201201264128.
Bai et al., "Naturally Occurring Broad-Spectrum Powdery Mildew Resistance in a Central American Tomato Accession Is Caused by Loss of Mb Function," MPMI, 2I(1):30-39 (2008).
Banerjee et al., "Efficient production of transgenic potato (S. tuberosum L. ssp. andigena) plants via Agrobacterium tumefaciens-mediated transformation," Plant Sci., 170:732 738 (2006).
Bayer et al., "Programmable ligand-controlled riboregulators of eukaryotic gene expression," Nature Biotechnol, 23 (3):337-343 (2005).
Bhargava et al., "Long double-stranded RNA-mediated RNA interference as a tool to achieve site-specific silencing of hypothalamic neuropeptides," Brain Research Protocols, 13:115-125 (2004).
Brugière et al., "Glutamine Synthetase in the Phloem Plays a Major Role in Controlling Proline Production," The Plant Cell, 11:1995-2011(1999).
Chabbouh et al., "Cucumber mosaic virus in artichoke," FAO Plant Protection Bulletin, 38:52-53 (1990).
Colbourne et al., "The Ecoresponsive Genome of Daphnia pulex," Science, 331(6017):555-561 (2011).
Communication pursuant to Article 94(3) EPC dated Jun. 26, 2015, as received in European Patent Application No. 11 753 916.3.
Dalmay et al., "An RNA-Dependent RNA Polymerase Gene in Arabidopsis Is Required for Posttranscriptional Gene Silencing Mediated by a Transgene but Not by a Virus," Cell, 101:543-553 (2000).
Preston et al., "Multiple effects of a naturally occurring proline to threonine substitution within acetolactate synthase in two herbicide-resistant populations of Lactuca serriola," Pesticide Biochem. Physiol., 84(3):227-235 (2006).
Rose et al., "Functional Polarity Is Introduced by Dicer Processing of Short Substrate RNAs," Nucleic Acids Research, 33(13):4140-4156 (2005).
Sathasivan et al., "Nucleotide sequence of a mutant acetolactate synthase gene from an imidazolinone-resistant Arabidopsis thaliana var. Columbia," Nucleic Acids Research, 18(8):2188-2193 (1990).
Supplementary European Search Report for EP 12831567.8 dated Jan. 29, 2015.
Ui-Tei et al., "Guidelines for the selection of highly effective siRNA sequences for mammalian and chick RNA interference," Nucleic Acids Res, 32(3): 936-948 (2004).
Van de Wetering et al., "Specific inhibition of gene expression using a stably integrated, inducible small-interfering-RNA vector," EMBO Rep, 4(6):609-615 (2003).
Vermeulen et al., "The Contributions of dsRNA Structure to Dicer Specificity and Efficiency," RNA, 11 (5):674-682 (2005).
Waterhouse et al., "Virus resistance and gene silencing in plants can be induced by simultaneous expression of sense and antisense RNA," Proc Natl Acad Sci USA, 95:13959-13964 (1998).
Welch et al., "Expression of ribozymes in gene transfer systems to modulate target RNA levels," Curr Opin Biotechnol. 3(5):486-496 (1998).
Sun et al., "A Highly efficient Transformation Protocol for Micro-Tom, a Model Cultivar for Tomato Functional Genomics," Plant Cell Physiol., 47(3):426-431 (2006).
Sun et al., "Down-Regulation of Arabidopsis DND1 Orthologs in Potato and Tomato Leads to Broad-Spectrum Resistance to Late Blight and Powdery Mildew", Transgenic Research, 2016, pp. 123-138, vol. 25.
Supplementary European Search Report for EP 1283156T8 dated Jan. 29, 2015.
Supplementary European Search Report for EP 12832415.9 dated Jan. 21, 2015.
Sutton et al., "Activity of Mesotrione on Resistant Weeds in Maize," Pest Manag. Sci., 58:981-984 (2002).
Takasaki et al., "An Effective Method for Selecting siRNA Target Sequences in Mammalian Cells," Cell Cycle, 3:790-795 (2004).
Tank Mixing Chemicals Applied to Peanut Crops: Are the Chemicals. Compatible?, College of Agriculture & Life Sciences, NC State University, AGW-653, pp. 1-11 (2004).
Taylor, "Seed Storage, Germination and Quality," The Physiology of Vegetable Crops, pp. 1-36 (1997).
Templeton et al., "Improved DNA: liposome complexes for increased systemic delivery and gene expression," Nature Biotechnology, 15:647-652 (1997).
Tepfer, "Risk assessment of virus resistant transgenic plants," Annual Review of Phytopathology, 40:467-491 (2002).
The Seed Biology Place, Website Gerhard Leubner Lab Royal Holloway, University of London, http://www.seedbiology.de/seedtechnology.asp, last updated May 2, 2012.
Thompson, et al., "CLUSTAL W: improving the sensitivity of progressive multiple sequence alignment through sequence weighting, position-specific gap penalties and weight matrix choice," Nucl. Acids Res., 22(22):4673-4680 (1994).
Timmons et al., "Specific interference by ingested dsRNA," Nature, 395:854 (1998).
Toriyama et al., "Transgenic Rice Plants After Direct Gene Transfer Into Protoplasts", Biotechnology, 1988, pp. 1072-1074, vol. 6.
Tran et al., "Control of specific gene expression in mammalian cells by co-expression of long complementary RNAs," FEBS Lett.;573(1-3):127-134 (2004).
Tranel et al., "Resistance of Weeds to ALS-Inhibiting Herbicides: What Have We Learned?," Weed Science, 50:700-712 (2002).
Tuschl, "Expanding small RNA interference," Nature Biotechnol., 20: 446-448 (2002).
Tuschl, "RNA Interference and Small Interfering RNAs," ChemBiochem. 2(4):239-245 (2001).
Töpfer et al., "Uptake and Transient Expression of Chimeric Genes in Seed-Derived Embryos," Plant Cell, 1:133-139 (1989).
Ui-Tei et al., "Guidelines for the selection of highly effective siRNA sequences for mammalian and chick RNA interference," Nucleic Acids Res., 32(3): 936-948 (2004).
Urayama et al., "Knock-down of OsDCL2 in Rice Negatively Affects Maintenance of the Endogenous dsRNA Virus, Oryza sativa Endomavirus," Plant and Cell Physiology, 51(1):58-67 (2010).
Van de Wetering et al., "Specific inhibition of gene expression using a stably integrated, inducible small-interfering-RNA vector," EMBO Rep., 4(6):609-615 (2003).
Vasil et al., "Herbicide Resistant Fertile Transgenic Wheat Plants Obtained by Microprojectile Bombardment of Regenerable Embryogenic Callus," Bio/Technology,10:667-674 (1992).
Vencill et al., "Resistance of Weeds to Herbicides," Herbicides and Environment, 29:585-594 (2011).
Verma et al., "Modified oligonucleotides: synthesis and strategy for users," Annu. Rev. Biochem., 67:99-134 (1998).
Vermeulen et al, "The Contributions of dsRNA Structure to Dicer Specificity and Efficiency," RNA, 11 (5):674-682 (2005).
Vert et al., "An accurate and interpretable model for siRNA efficacy prediction," BMC Bioinformatics, 7:520 (2006).
Wakelin et al., "A target-site mutation is present in a glyphosate-resistant Lolium rigidum population," Weed Res. (Oxford), 46(5):432-440 (2006).
Walton et al., "Prediction of antisense oligonucleotide binding affinity to a structured RNA target," Biotechnol Bioeng 65 (1):1-9 (1999).
Wan et al., "Generation of Large Numbers of Independently Transformed Fertile Barley Plants," Plant Physiol., 104:37-48 (1994).
Wang et al., "A Web-Based Design Center for Vector-Based siRNA and siRNA Cassette", BioInformatic Applications Note, 2004, pp. 1818-1820, vol. 20 No. 11.
Warnasooriya et al., "Using transgenic modulation of protein synthesis and accumulation to probe protein signaling networks in Arabidopsis thaliana" Plant Signaling & Behavior, 6(9):1312-1321 (2011).

(56) References Cited

OTHER PUBLICATIONS

Waterhouse et al., "Virus resistance and gene silencing in plants can be induced by simultaneous expression of sense and antisense RNA," Proc Natl Arad Sci USA, 95:13959-13964 (1998).
Welch et al., "Expression of ribozymes in gene transfer systems to modulate target RNA levels," Curr Opin Biotechnol. 9(5):486-496 (1998).
Written Opinion dated May 8, 2014, in International Application No. PCT/IL2013/050447.
Written Opinion dated Sep. 4, 2014, in Singapore Patent Application No. 201206152-9.
Yan et al, "Sprout Vacuum-Infiltration: A Simple and Efficient Agroinoculation Method for Viru-Induced Gene Silencingin Diverse Solanaceous Species", Plant Cell Reports, Sep. 2012, pp. 1713-1722, vol. 31 Issue 9.
Yu et al., "Gene-for-gene Disease Resistance Without the Hypersensitive Response in *Arabidopsis* dnd1 Mutant", Proceedings of the National Academy of Sciences of the United States of America, Jun. 23, 1998, pp. 7819-7824, vol. 95 No. 13.
Yuan et al., "A High Throughput Barley Strip Mosaic Virus Vector for Virus Induced Gene Silencing in Monocots and Dicots", PLOS One, Oct. 21, 2011, pp. 1-16, vol. 6 Issue 10 e26468.
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," PNAS, 98(12):6617-6622 (2001).
Zhai et al., "Establishing RNA Interference as a Reverse-Genetic Approach for Gene Functional Analysis in Protoplasts" Plant Physiology, 149:642-652 (2009).
Zhang et al., "A novel rice gene, NRR responds to macronutrient deficiency and regulates root growth," Mol Plant, 5 (1):63-72 (2012).
Zhang et al., "DEG: a database of essential genes," Nucleic Acids Res., 32:D271-D272 (2004).
Zhang et al., "Transgenic rice plants produced by electroporation-mediated plasmid uptake into protoplasts," The Plant Cell Rep., 7:379-384 (1988).
Della-Cioppa et al., "Import of a precursor protein into chloroplasts is inhibited by the herbicide glyphosate," The EMBO Journal, 7(5):1299-1305 (1988).
Diallo et al., "Long Endogenous dsRNAs Can Induce Complete Gene Silencing in Mammalian Cells and Primary Cultures," Oligonucleotides, 13:381-392 (2003).
Ellington et al., "In vitro selection of RNA molecules that bind specific ligands," Nature, 346:818-822 (1990).
Emery et al., "Radial Patterning of Arabidopsis Shoots by Class III HD-ZIP and KANADI Genes," Current Biology, 13:1768-1774 (2003).
Eurasian Office Action dated Feb. 24, 2014, in Application No. 201201264.
European Supplemental Search Report dated Oct. 8, 2013 in Application No. 11753916.3.
Extended European Search Report dated Jun. 29, 2015, in European Patent Application No. 12831494.5.
Farooq et al., "Rice seed priming," IPRN, 30(2):45-48 (2005).
Final Office Action dated Nov. 7, 2013, in U.S. Appl. No. 13/042,856.
Fire et al., "Potent and specific genetic interference by double-stranded RNA in Caenorhabditis elegans," Nature, 391:806-811 (1998).
First Examination Report issued for New Zealand Application No. 601784 dated Apr. 23, 2013.
First Examination Report dated Jul. 28, 2014, in New Zealand Patent Application No. 627060.
First Office Action dated May 27, 2015, in Chinese Patent Application No. 201280054179.8.
Fukuhara et al., "Enigmatic Double-Stranded RNA in Japonica Rice," Plant Molecular Biology, 21:1121-1130 (1993).
Fukuhara et al., "The Unusual Structure of a Novel RNA Replicon in Rice," The Journal of Biological Chemistry, 270 (30):18147-18149 (1995).
Fukuhara et al., "The wide distribution of endomaviruses, large double-stranded RNA replicons with plasmid-like properties," Archives of Virology, 151:995-1002 (2006).
Further Examination Report issued in New Zealand Patent Application No. 601784 dated May 16, 2014.
Ge et al., "Rapid vacuolar sequestration: the horseweed glyphosate resistance mechanism," Pest Management Sci., 66:345-348 (2010).
Gelvin, "Agrobacterium-Mediated Plant Transformation: The Biology Behind the "Gene-Jockeying" Tool", Microbiology and Molecular Biology Reviews, Mar. 2003, p. 16-37, vol. 67 No. 1.
GenBank Accession No. AY545657.1, published 2004.
GenBank Accession No. DY640489, PU2_plate27_F03 PU2 Prunus persica cDNA similar to expressed mRNA inferred from Prunus persica hypothetical domain/motif containing IPR011005:Dihydropteroate synthase-like, MRNA sequence (2006) [Retrieved on Feb. 4, 2013]. Retrieved from the internet <URL: http://www.ncbi.nlm.nih.gov/nucest/DY640489>.
GenBank Accession No. EU24568—"Amaranthus hypochondriacus acetolactate synthase (ALS) gene," (2007).
GenBank Accession No. FJ972198, Solanum lycopersicum cultivar Ailsa Craig dihydropterin pyrophosphokinase-dihydropteroate synthase (HPPK-DHPS) gene, complete cds (2010) [Retrieved on Nov. 26, 2012]. Retrieved from the internet ,URL: http://www.ncbi.nlm.nih.gov/nuccore/FJ972198>.
GenBank accession No. GI:186478573, published Jan. 22, 2014.
GenEmbl FJ861243, published Feb. 3, 2010.
Gressel et al., "A Strategy to Provide Long-Term Control of Weedy Rice While Mitigating Herbicide Resistance Transgene Flow, and Its Potential Use for Other Crops with Related Weeds", Pest Management Science, 2009, pp. 123-731, vol. 65.
Gutensohn et al., "Functional analysis of the two *Arabidopsis* homologues of Toc34, a component of the chloroplast protein import apparatus," The Plant Journal, 23(6):771-783 (2000).
Haigh, "The Priming of Seeds: Investigation into a method of priming large quantities of seeds using salt solutions," Thesis submitted to Macquarie University (1983).
Han et al., "Molecular Basis for the Recognition of Primary microRNAs by the Drosha-DGCR8 Complex," Cell, 125 (5):887-901 (2006).
Hardegree, "Drying and storage effects on germination of primed grass seeds," Journal of Range Management, 47 (3):196-199 (1994).
Herman et al., "A three-component dicamba O-demethylase from Pseudomonas maltophilia, strain DI-6: gene isolation, characterization, and heterologous expression," J. Biol. Chem., 280: 24759-24767 (2005).
Hidayat et al., "Enhanced Metabolism of Fluazifop Acid in a Biotype of Digitaria sanguinalis Resistant to the Herbicide Fluazifop-P-Butyl," Pesticide Biochem. Physiol., 57:137-146 (1997).
Hirschberg et al., "Molecular Basis of Herbicide Resistance in Amaranthus hybridus," Science, 222:1346-1349 (1983).
Hoekema et al., "A binary plant vector strategy based on separation of vir- and T-region of the Agrobacterium tumefaciens Ti-plasmid," Nature, 303:179-180 (1983).
Hofgen et al., "Repression of Acetolactate Synthase Activity through Antisense Inhibition: Molecular and Biochemical Analysis of Transgenic Potato (*Solanum tuberosum* L cv Desiree) Plants," Plant Physiol., 107(2):469-477 (1995).
Hsieh et al., "A library of siRNA duplexes targeting the phosphoinositide 3-kinase pathway: determinants of gene silencing for use in cell-based screens," Nucleic Acids Res., 32(3):893-901 (2004).
Huesken et al., "Design of a genome-wide siRNA library using an artificial neural network," Nature Biotechnology, 23 (8): 995-1001 (2005).

(56) References Cited

OTHER PUBLICATIONS

Ichihara et al., "Thermodynamic instability of siRNA duplex is a prerequisite for dependable prediction of siRNA activities," Nucleic Acids Res., 35(18):e123 (2007).
International Preliminary Report on Patentability (Chapter II) dated Jul. 24, 2015, in International Application No. PCT/US2014/047204.
International Preliminary Report on Patentability dated Sep. 11, 2014, in International Application No. PCT/IL13/50447.
International Search Report and the Written Opinion dated Feb. 25, 2013, in International Application No. PCT/US12/54883.
International Search Report and the Written Opinion dated Feb. 27, 2013, in International Application No. PCT/US12/54814.
International Search Report and the Written Opinion dated Feb. 27, 2013, in International Application No. PCT/US12/54842.
International Search Report and the Written Opinion dated Feb. 27, 2013, in International Application No. PCT/US12/54862.
International Search Report and the Written Opinion dated Feb. 27, 2013, in International Application No. PCT/US12/54894.
International Search Report and the Written Opinion dated Feb. 27, 2013, in International Application No. PCT/US12/54974.
International Search Report and the Written Opinion dated Feb. 27, 2013, in International Application No. PCT/US12/54980.
International Search Report and the Written Opinion dated Jul. 15 2014, in International Application No. PCT/US2014/025305.
International Search Report and the Written Opinion dated Jul. 22 2014, in International Application No. PCT/IL2013/051083.
International Search Report and the Written Opinion dated Jul. 22 2014, in International Application No. PCT/IL2013/051085.
International Search Report and the Written Opinion dated Jul. 24 2014, in International Application No. PCT/US2014/026036.
International Search Report and the Written Opinion dated Oct. 1 2013, in International Application No. PCT/IL2013/050447.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion issued in PCT/US13/61475, dated Apr. 8, 2014.
International Search Report and Written Opinion dated Jul. 8 2015 in International Application No. PCT/US2015/011408.
International Search Report and Written Opinion dated Mar. 26, 2015, in International Application No. PCT/US2014/069353.
International Search Report dated Mar. 12, 2013 in International Application No. PCT/US 12/54789.
Isaacs et al., "Engineered riboregulators enable post-transcriptional control of gene expression," Nature Biotechnology, 22(7):841-847 (2004).
Ji et al., "Regulation of small RNA stability: methylation and beyond," Cell Research, 22:624-636 (2012).
Jofre-Garfias el al., "Agrobacerium-Mediated Transformation of Amaranthus Hypochondriacus: Light- and Tissue-Specific Expression of a Pea Chlorophyll A/B-Binding Protein Promoter," Plant Cell Reports, 16:847-852 (1997).
Josse et al., "A DELLA in Disguise: SPATULA Restrains the Growth of the Developing *Arabidopsis* Seedling," Plant Cell, 23:1337-1351 (2011).
Kam et al., "Nanotube Molecular Transporters:? Internalization of Carbon Nanotube?Protein Conjugates into Mammalian Cells," J. Am. Chem. Soc., 126(22):6850-6851 (2004).
Kaplan et al., "Cyclic Nucleotide-Gated Channels in Plants", Federation of European Biochemical Societies (FEBS) Letters, 2007, pp. 2237-2246, vol. 581.
Katoh et al., "Specific residues at every third position of siRNA shape its efficient RNAi activity," Nucleic Acids Res., 35 (4): e27 (2007).
Kertbundit et al., "In vivo random β-glucuronidase gene fusions in *Arabidopsis thaliana*," Proc. Natl. Acad. Sci. U S A., 88:5212-5216 (1991).

Khachigian, "DNAzymes: Cutting a path to a new class of therapeutics," Curr Opin Mol Ther 4(2):119-121 (2002).
Khan et al., "Matriconditioning of Vegetable Seeds to Improve Stand Establishment in Early Field Plantings," .1 Amer. Soc. Hon. Sci., 1 17(1):41-47 (1992).
Khodakovskaya et al., "Carbon Nanotubes Are Able to Penetrate Plant Seed Coat and Dramatically Affect Seed Germination and Plant Growth," ACS Nano, 3(10):3221-3227 (2009).
Kim et al., "Synthetic dsRNA Dicer substrates enhance RNAi potency and efficacy," Nature Biotechnology, 23 (2):222-226 (2005).
Kozomara et al., "miRBase: Annotating High Confidence MicroRNAs Using Deep Sequencing Data", Nucleic Acids Research, 2014, p. D68-D73, vol. 42.
Kronenwett et al., "Oligodeoxyribonucleotide Uptake in Primary Human Hematopoietic Cells Is Enhanced by Cationic Lipids and Depends on the Hematopoietic Cell Subset," Blood, 91(3):852-862 (1998).
Lavigne et al., "Enhanced antisense inhibition of human immunodeficiency virus type 1 in cell cultures by DLS delivery system," Biochem Biophys Res Commun, 237:566-571 (1997).
Lee et al., "Aptamer Database," Nucleic Acids Research, 32:D95-D100 (2004).
Leopold et al., "Chapter 4: Moisture as a Regulator of Physiological Reaction in Seeds," Seed Moisture, CSSA Special—Publication No. 14, pp. 51-69 (1989).
Li et al., "Establishment of a highly efficient transformation system for pepper (*Capsicum annuum* L.)," Plant Cell Reports, 21: 785-788 (2003).
Liu et al., "Carbon Nanotubes as Molecular Transporters for Walled Plant Cells," Nano Letters, 9(3):1007-1010 (2009).
Liu et al., "DNAzyme-mediated recovery of small recombinant RNAs from a 5S rRNA-derived chimera expressed in *Escherichia coli*," BMC Biotechnology, 10:85 (2010).
Llave et al., "Endogenous and Silencing-Associated Small RNAs in Plants," The Plant Cell, 14:1605-1619 (2002).
Lu et al., "Novel and Mechanical Stress-Responsive MicroRNAs in Populus Trichocarpa That Are Absent from *Arabidopsis*", The Plant Cell, Aug. 2005, pp. 2186-2203, vol. 17.
Lu et al., "OligoWalk: an online siRNA design tool utilizing hybridization thermodynamics," Nucleic Acids Research, 36: W104-W108 (2008).
Lu et al., "RNA silencing in plants by the expression of siRNA duplexes," Nucleic Acids Res., 32(21):e171 (2004).
Luft, "Making sense out of antisense oligodeoxynucleotide delivery: getting there is half the fun," J Mol Med, 76:75-76 (1998).
Mackenzie et al, "Transgenic Nicotiana Debneyii Expressing Viral Coat Protein Are Resistant to Potato Virus S Infection," Journal of General Virology, 71:2167-2170 (1990).
Maher III et al., "Inhibition of DNA binding proteins by oligonucleotide-directed triple helix formation," Science, 245 (4919):725-730 (1989).
Mallory et al, "MicroRNA Control of PHABULOSA in Leaf Development: Importance of Pairing to the MicroRNA 5' Region", The EMBO Journal, 2004, pp. 3356-3364, vol. 23 No. 16.
Mandal et al., "Adenine riboswitches and gene activation by disruption of a transcription terminator," Nature Struct. Mol. Biol., 11(1):29-35 (2004).
Mandal et al., "Gene Regulation by Riboswitches," Nature Reviews I Molecular Cell Biology, 5:451-463 (2004).
Manoharan, "Oligonucleotide Conjugates as Potential Antisense Drugs with Improved Uptake, Biodistribution, Targeted Delivery, and Mechanism of Action," Antisense & Nucleic Acid Drug Development, 12:103-128 (2002).
Mansoor et al., "Engineering Novel Traits in Plants Through RNA Interference", Trends in Plant Science, 2006, pp. 559-565, vol. 11, No. 11.
Masoud et al., "Constitutive expression of an inducible β-1,3-glucanase in alfalfa reduces disease severity caused by the oomycete pathogen *Phytophthora megasperma* f. sp *medicaginis*, but does not reduce disease severity of chitincontaining fungi," Transgenic Research, 5:313-323 (1996).

(56) References Cited

OTHER PUBLICATIONS

Matveeva et al., "Prediction of antisense oligonucleotide efficacy by in vitro methods," Nature Biotechnology, 16:1374-1375 (1998).
Meinke, et al., "Identifying essential genes in *Arabidopsis thaliana*," Trends Plant Sci., 13(9):483-491 (2008).
Misawa et al., "Expression of an Erwinia phytoene desaturase gene not only confers multiple resistance to herbicides interfering with carotenoid biosynthesis but also alters xanthophyll metabolism in transgenic plants," The Plant Journal, 6(4):481-489 (1994).
Misawa et al., "Functional expression of the Erwinia uredovora carotenoid biosynthesis gene crtl in transgenic plants showing an increase of ?-carotene biosynthesis activity and resistance to the bleaching herbicide norflurazon," The Plant Journal, 4(5):833-840 (1993).
Miura et al., "The Balance between Protein Synthesis and Degradation in Chloroplasts Determined Leaf Variegation in *Arabidopsis* yellow variegated Mutants," The Plant Cell, 19:1313-1328 (2007).
Molina et al, "Inhibition of Protoporphyrinogen Oxidase Expression in *Arabidopsis* Causes a Lesion-Mimic Phenotype That Induces Systemic Acquired Resistance," The Plant Journal, 1 7(6):667-678 (1999).
Molnar et al., "Plant Virus-Derived Small Interfering RNAs Originate Predominantly from Highly Structured Single-Stranded Viral RNAs," Journal of Virology, 79(12):7812-7818 (2005).
Momentive Performance Materials Inc. Marketing Bulleting for Silwet L77* Ag spray adjuvant DA Performance Additives, 2011, pp. 1-4.
Moriyama et al., "Double-stranded RNA in rice: a novel RNA replicon in plants," Molecular & General Genetics, 248 (3):364-369 (1995).
AccuStandard, Inc., "Pesticide Standards Reference Guide", 2010, 116 pages.
Agrios, Plant Pathology (Second Edition), 2:466-470 (1978).
Alarcón-Reverte et al., "Resistance to ACCase-inhibiting herbicides in the weed Lolium multiflorum," Comm. Appl. Biol. Sci., 73(4):899-902 (2008).
Amarzguioui et al., "An algorithm for selection of functional siRNA sequences," Biochemical and Biophysical Research Communications, 316:1050-1058 (2004).
Ambrus et al., "The Diverse Roles of RNA Helicases in RNAi," Cell Cycle, 8(21):3500-3505 (2009).
Anonymous, "A handbook for high-level expression and purification of 6xHis-tagged proteins," The QIAexpressionist, (2003).
Anonymous, "Do Monsanto Have the Next Big Thing?" Australian Herbicide Resistance Initiative (AHRI), retreived on Jan. 19, 2015, XP007922963.
Aoki et al., "In Vivo Transfer Efficiency of Antisense Oligonucleotides into the Myocardium Using HVJ-Liposome Method," Biochem Biophys Res Commun, 231:540-545 (1997).
Arpaia et al., "Production of transgenic eggplant (*Solanum melongena* L) resistant to Colorado Potato Beetle (*Leptinotarsa decemlineata* Say)," (1997) Theor. Appl. Genet., 95:329-334 (1997).
Austrailian Government, Grains Research & Development Corporation, "Adjuvants: Oils, Surfactants and other Additives for Farm Chemicals", 2012, 52 pages.
Australian Patent Examination report No. 1 dated Nov. 11, 2013, in Australian Application No. 2011224570.
Axtell et al., "A Two-Hit Trigger for siRNA Biogenesis in Plants," Cell, 127:565?577 (2006).
Baerson et al., "Glyphosate-Resistant Goosegrass. Identification of a Mutation in the Target Enzyme 5-Enolpyruvylshikimate-3-Phosphate Synthase," Plant Physiol., 129(3):1265-1275 (2002).
Bai et al., "Naturally Occurring Broad-Spectrum Powdery Mildew Resistance in a Central American Tomato Accession Is Caused by Loss of Mb Function," MPMI, 21(1):30-39 (2008).
Balcombe et al., "RNA Silencing and Heritable Epigenetic Effects in Tomato and *Arabidopsis*", Abstract 13th Annual Fall Symposium, Plant Genomes to Phenomes, Donal Danforth Plant Science, Sep. 28-30, 2011.
Banerjee et al., "Efficient production of transgenic potato (*S. tuberosum* L ssp. *andigena*) plants via Agrobacterium tumefaciens-mediated transformation," Plant Sci., 170:732 738 (2006).
Bayer et al., "Programmable ligand-controlled riboregulators of eukaryotic gene expression," Nature Biotechnol., 23 (3):337-343 (2005).
Beal, et al., "Second Structural Motif for Recognition of DNA by Oligonucleotide-Directed Triple-Helix Formation," Science, 251:1360-1363 (1992).
Becker et al., "Fertile transgenic wheat from microprojectile bombardment of scutellar tissue," The Plant Journal, 5 (2):299-307 (1994).
Bhargava et al., "Long double-stranded RNA-mediated RNA interference as a tool to achieve site-specific silencing of hpothalamic neuropeptides," Brain Research Protocols, 13:115-125 (2004).
Boletta et al., "High Efficient Non-Viral Gene Delivery to the Rat Kidney by Novel Polycationic Vectors," J. Am Soc. Nephrol., 7:1728 (1996).
Bolognesi et al., "Characterizing the Mechanism of Action of Double-Stranded RNA Activity against Western Corn Rootworm(Diabrotica virgifera virgifera LeConte)," PLoS One 7(10):e47534 (2012).
Bolter et al., "A chloroplastic inner envelope membrane protease is essential for plant development," FEBS Letters, 580:789-794 (2006).
Bourgeois et al., "Field and Producer Survey of Accase Resistant Wild Oat in Manitoba," Canadian Journal of Plant Science, 709-7 15 (1997).
Breaker et al., "A DNA enzyme with Mg2+-dependent RNA phosphoesterase activity," Chemistry and Biology, 2:655-660 (1995).
Brugière et al, "Glutamine Synthetase in the Phloem Plays a Major Role in Controlling Praline Production," The Plant Cell, 11:1995-2011(1999).
Busi et al., "Gene Flow Increases the Initial Frequency of Herbicide Resistance Alleles in Unselected Lolium Rigidum Populations", Agriculture, Ecosystems and Environments, 2011, pp. 403-409, vol. 142.
Butler et al., "Priming and re-drying improve the survival of mature seeds of Digitalis purpurea during storage," Annals of Botany, 103:1261-1270 (2009).
Bytebier et al., "T-DNA organization in tumor cultures and transgenic plants of the monocotyledon Asparagus officinalis," Proc. Natl. Acad. Sci. U.S.A., 84:5345-5349 (1987).
Chabbouh et al. "Cucumber mosaic virus in artichoke," FAO Plant Protection Bulletin, 38:52-53 (1990).
Chakravarty et al., "Genetic Transformation in Potato: Approaches and Strategies," Amer J Potato Res, 84:301 311 (2007).
Chan et al., "A Cyclic Nucleotide-Gated Ion Channel, CNGC2, Is Crucial for Plant Development and Adaption to Calcium Stress1" , 2003 Scientific Correspondence, p. 728-731, vol. 132.
Chang et al., "Cellular Internalization of Fluorescent Proteins via Arginine-Rich Intracellular Delivery Peptide in Plant Cells", Plant Cell Physiology, 2005, pp. 482-488, vol. 46.
Chee et al., "Transformation of Soybean (Glycine max) by Infecting Germinating Seeds with Agrobacterium tumefaciens," Plant Physiol., 91:1212-1218 (1989).
Chen et al., "In Vivo Analysis of the Role of atTic20 in Protein Import into Chloroplasts," The Plant Cell, 14:641-654 (2002).
Cheng et al., "Production of fertile transgenic peanut (*Arachis hypogaea* L.) plants using Agrobacterium tumefaciens," Plant Cell Reports, 15:653-657 (1996).
Chi et al., "The Function of RH22, a DEAD RNA Helicase, in the Biogenesis of the 50S Ribosomal Subunits of *Arabidopsis* Chloroplasts," Plant Physiology, 158:693-707 (2012).
Chinese Office Action dated Aug. 28, 2013 in Chinese Application No. 201180012795.2.
Chupp et al., "Chapter 8: White Rust," Vegetable Diseases and Their Control, The Ronald Press Company, New York, pp. 267-269 (1960).
Clough et al., "The *Arabidopsis* dnd1 "Defense, No Death" Gene Encodes a Mutated Cyclic Nucleotide-gated Ion Channel", Proceed-

(56) References Cited

OTHER PUBLICATIONS ings of the National Academy of Sciences of the United States of America, Aug. 2000, pp. 9323-9328, vol. 97 No. 16.
Colbourne et al., "The Ecoresponsive Genome of Daphnia pulex," Science, 331(6017):555-561 (2011).
Colombian Office Action dated Aug. 2, 2013 in Application No. 12 152898.
Colombian Office Action dated Feb. 21, 2014 in Application No. 12 152898.
Communication pursuant to Article 94(3) EPC dated Jun. 26, 2015, as received in European Patent Application No. 11 753 9163.
Consonni et al., "Conserved Requirement for a Plant Host Cell Protein in Powdery Mildew Pathogenesis", Nature Genetics, 2006, pp. 716-720, vol. 38, No. 6.
Dalmay et al., "An RNA-Depenedent RNA Polymerase Gene in *Arabidopsis* Is Required for Posttranscriptional Gene Silencing Mediated by a Transgene but Not by a Virus," Cell, 101:543-553 (2000).
Datebase EMBL CBIB Daphnia—XP-002732239 (2011).
Davidson et al., "Engineering regulatory RNAs," TRENDS in Biotechnology, 23(3):109-112 (2005).
De Block, et al. "Engineering herbicide resistance in plants by expression of a detoxifying enzyme," EMBO J. 6 (9):2513-2519 (1987).
De Framond, "MINI-Ti: A New Vector Strategy for Plant Genetic Engineering," Nature Biotechnology, 1:262-269 (1983).
Moriyama et al., "Stringently and developmentally regulated levels of a cytoplasmic double-stranded RNA and its high-efficiency transmission via egg and pollen in rice," Plant Molecular Biology, 31:713-719 (1996).
Morrissey et al., "Potent and persistent in vivo anti-HBV activity of chemically modified siRNAs," Nat Biotechnol. 23 (8):1002-1007 (2005).
Moser et al., "Sequence-Specific Cleavage of Double Helical DNA by Triple Helix Formation," Science, 238:645-646 (1987).
Non-Final Office Action dated Apr. 11, 2013, in U.S. Appl. No. 13/042,856.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated May 15, 2015, in U.S. Appl. No. 14/608,951.
Non-Final Office Action dated May 22, 2015, in U.S. Appl. No. 13/612,985.
Office Action dated Feb. 17, 2014, in Mexican Patent Application No. MX/a/2012/010479.
Office Action for UA Application No. 201211548 dated Jul. 23, 2015.
Office Action dated Jan. 6, 2015, in Japanese Patent Application No. 2012-557165.
Office Action dated Nov. 19, 2014, in Eurasian Patent Application No. 201201264/28.
Office Action dated Nov. 3, 2014, in Chinese Patent Application No. 201180012795.2.
Office Action dated Oct. 8, 2014, in Mexican Patent Application MX/a/2012/010479.
Paddison et al., "Stable suppression of gene expression by RNAi in mammalian cells," Proc. Natl Acad. Sci. USA, 99 (3):1443-1448 (2002).
Palauqui et al., "Activation of systemic acquired silencing by localised introduction of DNA," Current Biology, 9:59-66 (1999).
Parera et al., "Dehydration Rate after Solid Matrix Priming Alters Seed Performance of Shrunken-2 Corn," J. Amer. Soc. Hort. Sci., 119(3):629-635 (1994).
Peretz et al., "A Universal Expression/Silencing Vector in Plants," Plant Physiology, 145:1251-1263 (2007).
Pomprom et al., "Glutamine synthetase mutation conferring target-site-based resistance to glufosinate in soybean cell selections," Pest Manag Sci, 2009; 65(2):216-222 (2009).
Pratt et al., "Amaranthus Rudis and A. Tuberculatus, One Species or Two?," Journal of the Torrey Botanical Society, 128(3):282-296 (2001).
Preston et al., "Multiple effects of a naturally occurring praline to threonine substitution within acetolactate synthase in two herbicide-resistant populations of Lactuca serriola," Pesticide Biochem. Physiol., 84(3):227-235 (2006).
Qiwei,"Progress in DNA interference," Progress in Veterinary Medicine, 30(1):71-75 (2009).
Rajur et al., "Covalent Protein-Oligonucleotide Conjugates for Efficient Delivery of Antisense Molecules," Bioconjug Chem., 8:935-940 (1997).
Reddy et al., "Aminomethylphosphonic Acid Accumulation in Plant Species Treated with Glyphosate," J. Agric. Food Chem., 56(6):2125-2130 (2008).
Reither et al., "Specificity of DNA triple helix formation analyzed by a FRET assay," BMC Biochemistry, 3:27 (2002).
Riggins et al., "Characterization of De Nova Transcriptome for Waterhemp (*Amaranthus Tuberculalus*) Using Gs-Flx 454 Pyrosequeneing and Its Application for Studies of Herbicide Target-Site Genes," Pest Manag. Sci., 66:1042-1052 (2010).
Rose et al, "Functional Polarity Is Introduced by Dicer Processing of Short Substrate RNAs," Nucleic Acids Research, 33(13):4140-4156 (2005).
Santoro et al., "A general purpose RNA-cleaving DNA enzyme," Proc. Natl. Acad. Sci. USA, 94:4262-4266 (1997).
Sathasivan et al., "Nucleotide sequence of a mutant acetolactate synthase gene from an imidazolinone-resistant *Arabidapsis thaliana* var. Columbia," Nucleic Acids Research, 18(8):2188-2193 (1990).
Schwab et al., "RNA silencing amplification in plants: Size matters," PNAS, 107(34):14945-14946 (2010).
Schwember et al., "Drying Rates following Priming Affect Temperature Sensitivity of Germination and Longevity of Lettuce Seeds," HortScience, 40(3):778-781 (2005).
Second Chinese Office Action issued in Chinese Patent Application No. 201180012795.2, dated Jun. 10, 2014.
Seidman et al., "The potential for gene repair via triple helix formation," J Clin Invest., 112(4):487-494 (2003).
Selvarani et al., "Evaluation of seed priming methods to improve seed vigour of onion (*Allium cepa* cv. Aggregatum) and carrot (*Daucus carota*)," Journal of Agricultural Technology, 7(3):857-867 (2011).
Senthil-Kumar et al., "A Systematic Study to Determine the Extent of Gene Silencing in Nicotiana Benthamiana and Other Solanaccac Species When Heterologous Gene Sequences Are Used for Virus-Induced Gene Silencing", New Phylogist, 176:782-791 (2007).
Senthil-Kumar et al., "RNAi in Plants: Recent Developments and Applications in Agriculture", Gene Silencing: Theory, Techniques and Applications, Oct. 1, 2010, p. 185, Retrieved from the Internet: URL: https://www.researchgate.net/profile/Senthil-Kumar_Muthappa/publication/
216017213_RNAi_in_Plants_Recent_Developments_and_Applicationsin_Agriculture/links/097fe5ffe6c103ae5cc028f6.pdf, Retrieved on Feb. 14, 2017.
Sharma et al., "A simple and efficient Agrobacterium-mediated procedure for transformation of tomato," J. Biosci., 34 (3):423 433 (2009).
Sijen et al., "On the Role of RNA Amplification in dsRNA-Triggered Gene Silencing," Cell, 107:465-476 (2001).
Singh et al., "Absorption and translocation of glyphosate with conventional and organosilicone adjuvants," Weed Biology and Management, 8:104-111 (2008).

(56) References Cited

OTHER PUBLICATIONS

Snead et al., "Molecular Basis for Improved Gene Silencing by Dicer Substrate Interfering RNA Compared With Other siRNA Variants," Nucleic Acids Research, 41(12):6209-6221 (2013).
Solano et al., "Isolation and Characterization of Strain MMB-1 (CECT 4803), a Novel Melanogenic Marine Bacterium," Appl. Environ. Microbial., 1997, pp. 3499, vol. 63 No. 9.
Somerville et al., "Plant Functional Genomics" Science, 285:380-383 (1999).
Steeves et al., "Transgenic soybeans expressing siRNAs specific to a major sperm protein gene suppress Heterodera glycines reproduction," Funct. Plant Biol., 33:991-999 (2006).
Strat et al., "Specific and nontoxic silencing in mammalian cells with expressed long dsRNAs," Nucleic Acids Research, 34(13):3803-3810 (2006).
Street, "Why is DNA (and not RNA) a Stable Storage Form for Genetic Information?," Biochemistry Revisited, pp. 1-4 (2008).
Sudarsan et al., "Metabolite-binding Rna domains are present in the genes of eukaryotes," RNA, 9:644-647 (2003).
Hu et al, "High Efficiency Transport of Quantum Dots into Plant Roots with the Aid of Silwet L-77", Plant Physiology and Biochemistry, Aug. 2010, pp. 703-709, vol. 48, Issue 8.

\* cited by examiner

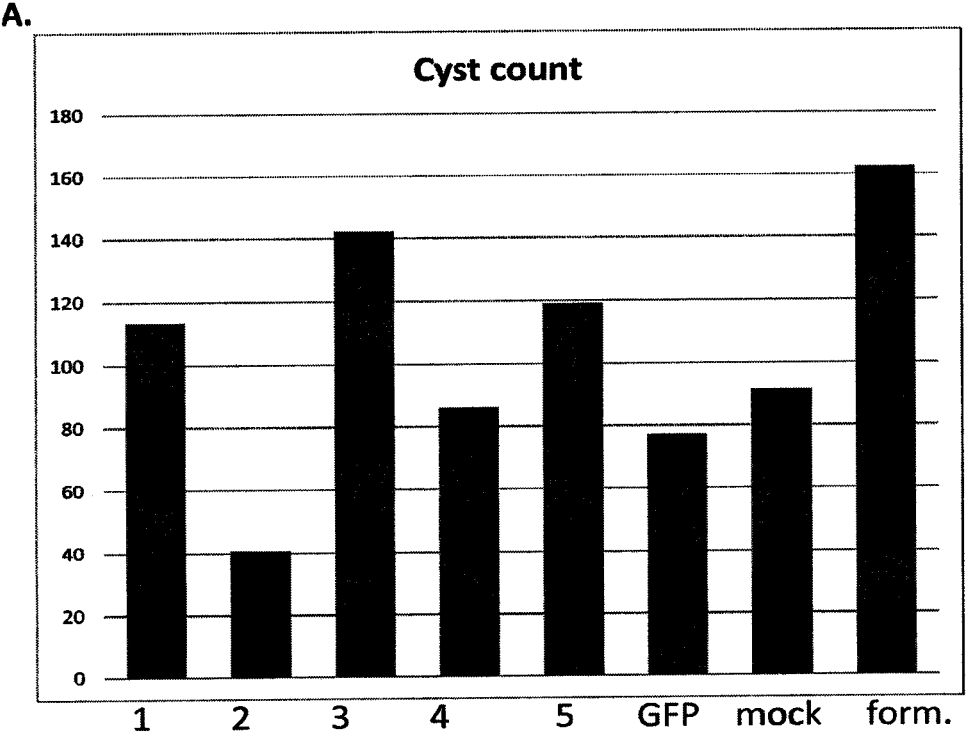
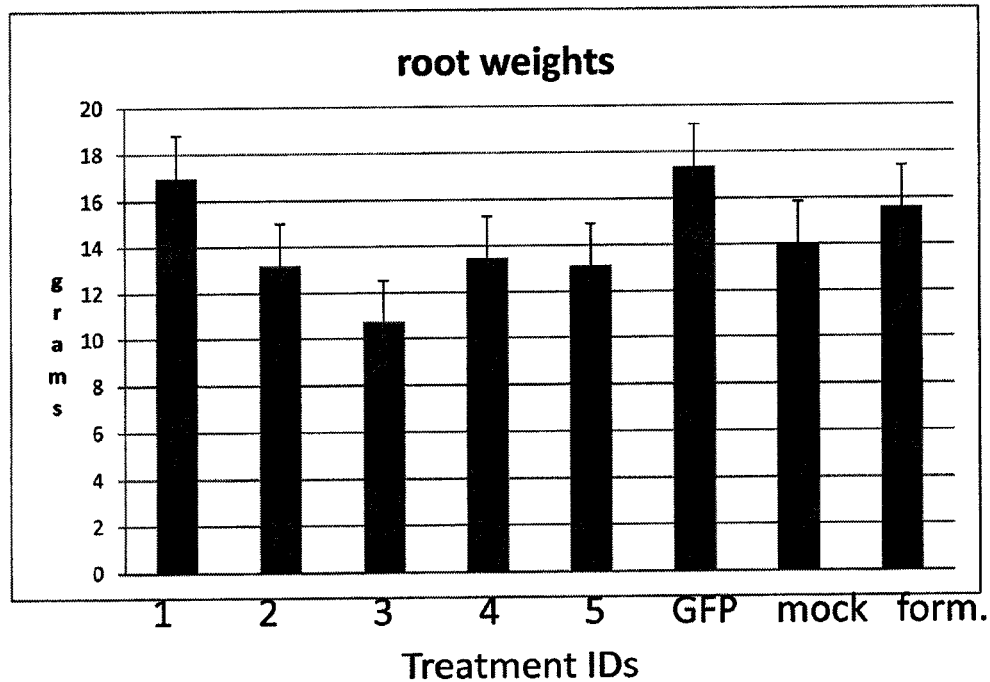
FIGURE 1A, B

SEQUENCE LISTING

<160> NUMBER OF SEQ ID NOS: 147

<210> SEQ ID NO 1
<211> LENGTH: 247
<212> TYPE: PRT
<213> ORGANISM: Arabidopsis thaliana

<400> SEQUENCE: 1

```
Met Asp Ala Phe Ser Ser Phe Phe Asp Ser Gln Pro Gly Ser Arg Ser
 1               5                  10                  15

Trp Ser Tyr Asp Ser Leu Lys Asn Phe Arg Gln Ile Ser Pro Ala Val
             20                  25                  30

Gln Asn His Leu Lys Arg Val Tyr Leu Thr Leu Cys Cys Ala Leu Val
         35                  40                  45

Ala Ser Ala Phe Gly Ala Tyr Leu His Val Leu Trp Asn Ile Gly Gly
     50                  55                  60

Ile Leu Thr Thr Ile Gly Cys Ile Gly Thr Met Ile Trp Leu Leu Ser
 65                  70                  75                  80

Cys Pro Pro Tyr Glu His Gln Lys Arg Leu Ser Leu Leu Phe Val Ser
                 85                  90                  95

Ala Val Leu Glu Gly Ala Ser Val Gly Pro Leu Ile Lys Val Ala Ile
            100                 105                 110

Asp Val Asp Pro Ser Ile Leu Ile Thr Ala Phe Val Gly Thr Ala Ile
            115                 120                 125

Ala Phe Val Cys Phe Ser Ala Ala Met Leu Ala Arg Arg Arg Glu
        130                 135                 140

Tyr Leu Tyr Leu Gly Gly Leu Leu Ser Ser Gly Leu Ser Met Leu Met
145                 150                 155                 160

Trp Leu Gln Phe Ala Ser Ser Ile Phe Gly Gly Ser Ala Ser Ile Phe
                165                 170                 175

Lys Phe Glu Leu Tyr Phe Gly Leu Leu Ile Phe Val Gly Tyr Met Val
            180                 185                 190

Val Asp Thr Gln Glu Ile Ile Glu Lys Ala His Leu Gly Asp Met Asp
            195                 200                 205

Tyr Val Lys His Ser Leu Thr Leu Phe Thr Asp Phe Val Ala Val Phe
        210                 215                 220

Val Arg Ile Leu Ile Ile Met Leu Lys Asn Ser Ala Asp Lys Glu Glu
225                 230                 235                 240

Lys Lys Lys Lys Arg Arg Asn
                245
```

<210> SEQ ID NO 2
<211> LENGTH: 1149
<212> TYPE: DNA
<213> ORGANISM: Arabidopsis thaliana

<400> SEQUENCE: 2

```
aatattttca ttaatcgatt ctcaaagtca agcaaaaaaa acgaaacaat ggatgcgttc      60
tcttccttct tcgattctca acctggtagc agaagctgga gctatgattc tcttaaaaac     120
ttccgtcaga tttctccagc cgttcagaat catcttaaac gggtttattt gaccttatgt     180
tgtgctcttg tggcgtctgc ctttggagct tacctccatg tgctctggaa tatcggcggt     240
attcttacaa cgattggatg tattggaact atgatttggc tcctttcatg tcctccttat     300
gaacaccaaa aaaggctttc tcttctgttt gtgtctgctg ttcttgaagg tgcttctgtt     360
ggccccttga tcaaagtggc aattgatgtt gacccaagca tccttatcac tgcatttgtt     420
ggaactgcga tagcgtttgt ctgtttctca gcagcagcaa tgttagcaag acgcagggag     480
tatctctacc ttggaggact gctttcatct ggcttgtcta tgctaatgtg gctccagttt     540
gcctcttcaa tctttggtgg ctctgcatct atctttaagt ttgagttgta ctttggactt     600
ttgatctttg tgggatacat ggtggtggac acacaagaga ttatagaaaa ggcacacctc     660
ggtgacatgg actatgtaaa acattcgttg acccttttca ctgactttgt agctgtgttt     720
gttcggattc tcatcataat gttgaagaac tcagcagata agaagagaa gaagaagaa      780
aggagaaact gaggggatgt aaagtaaatt taactttatg gttgttatcg tgtgtggcca     840
cttttgaagat attacttgtt agcactctct attggtgacc agacatgttt ccactaaaaa     900
ggatctgctt gtttcacttc tgcacaagta ccatcttcag attgtaaatg actcgagtgt     960
tgttcttctt ttcataaact tttgttcttt aagagtttgg ttctactgat tgcatcttac    1020
caagctaaga ataatgtagg aaaatgataa tcctgtttaa attttctaaa atgtgtgcat    1080
ttcagattct cacagttgca acatttgcta ttgcttggaa gttgtaatcg aaaaataact    1140
tgcaatttc                                                           1149
```

<210> SEQ ID NO 3
<211> LENGTH: 250
<212> TYPE: PRT
<213> ORGANISM: Lactuca sativa

<400> SEQUENCE: 3

```
Met Glu Ser Phe Ser Ser Phe Phe Asp Ser Gln Ser Arg Ser Ala Ser
1               5                   10                  15
Pro Asn Ser Trp Thr Tyr Asp Ser Leu Lys Asn Phe Arg Gln Ile Ser
            20                  25                  30
Pro Leu Val Gln Thr His Leu Lys Gln Val Tyr Leu Ser Leu Cys Cys
        35                  40                  45
Ala Leu Met Ala Ser Ala Val Gly Ala Tyr Leu His Ile Leu Trp Asn
    50                  55                  60
Ile Gly Gly Leu Leu Thr Thr Phe Gly Thr Leu Gly Cys Met Phe Trp
65                  70                  75                  80
Leu Leu Ala Thr Pro Gln Tyr Gln Glu Gln Lys Arg Val Ser Leu Leu
                85                  90                  95
Met Ala Ser Ser Leu Leu Gln Gly Ala Ser Ile Gly Pro Leu Ile Asp
            100                 105                 110
Leu Ala Ile Glu Phe Asp Pro Ser Ile Leu Val Ser Ala Phe Met Gly
        115                 120                 125
```

```
Thr Ala Ile Ala Phe Ala Cys Phe Ser Gly Ala Ala Met Leu Ala Arg
    130                 135                 140

Arg Arg Glu Tyr Leu Tyr Leu Gly Gly Leu Leu Ser Ser Gly Val Ser
145                 150                 155                 160

Ile Leu Phe Trp Leu His Phe Ala Ser Ser Ile Phe Gly Gly Ser Val
                165                 170                 175

Ala Leu Phe Lys Phe Glu Leu Tyr Phe Gly Leu Leu Val Phe Val Gly
            180                 185                 190

Tyr Met Val Val Asp Thr Gln Asp Ile Ile Glu Lys Ala His Leu Gly
        195                 200                 205

Asp Leu Asp Tyr Val Lys His Ala Leu Thr Leu Phe Thr Asp Phe Ile
    210                 215                 220

Ala Val Phe Val Arg Ile Leu Ile Ile Met Leu Lys Asn Ser Ala Glu
225                 230                 235                 240

Arg Glu Glu Lys Lys Lys Arg Arg Asp
                245                 250
```

<210> SEQ ID NO 4
<211> LENGTH: 1251
<212> TYPE: DNA
<213> ORGANISM: Lactuca sativa

<400> SEQUENCE: 4

```
ggcgacttcg cgaaactacc ggattactta actatgtctg caaacgtgta ctataaatat      60
cgcatatttt cttcccccaa aagtcatcgg ttcaatacca aaatttcata gttctttgtt     120
ttcttcaact accatggaat cattctcatc gttcttcgat tcacaatcgc gatcggcttc     180
tccaaacagc tggacctacg attctctcaa gaatttccgt caaatctctc ccttagttca     240
gactcatctc aaacaggttt acctctcact atgttgtgct ctcatggcat ctgcagttgg     300
ggcttacctt cacatcctat ggaacatcgg tggccttcta accacttcg gaacgttggg      360
ctgcatgttt tggctactcg ccactccaca atatcaagag caaaaagag tctctctatt      420
aatggcatct tctcttctcc aaggagcctc catcggtcct ctaatcgact tagccataga     480
atttgaccca agcatcttgg tgagcgcgtt catgggaact gcaatcgcat ttgcttgttt     540
ctcaggagct gccatgttag caagacgcag agagtatctt tatcttggag gtcttctttc     600
ttctggtgtt tcaatccttt tctggttaca ttttgcctca tcaatctttg gtggctctgt     660
tgccctttc aaatttgagt tgtactttgg gctgttggtg tttgttgggt acatggtggt      720
tgacacccaa gatatcattg aaaaggctca tcttggagat ttggattatg tgaaacatgc     780
tcttacgctt tcactgatt tcattgctgt ttttgttcgc attcttatca tcatgttgaa      840
gaattcggct gaaagagaag agaagaagaa gagaggagg gattagggtg tttgtgaatg     900
agaaaaatgt gaagctttct gactacaaat aaaatgcgat gtagttgtta cttttgtgta     960
gtacattgtt ttttttaaca tgagtgacgt atatgtccta tgtcaatttg agattatgt     1020
attaaaccct tataaaccca acaatctatc tcaatgtggg gttatttaaa ttatcccatg    1080
tactcgatcc aagtgtttaa aagctcatta cattacatta tcttcgaata ctaataattt    1140
atcgtattca catgcgtatg gggtttccta ctttactagt acattacccc agattttaa     1200
gaccaagttg aattgcattt ttaagtactc ctaattttgt gcaaaccacg t              1251
```

<210> SEQ ID NO 5
<211> LENGTH: 248
<212> TYPE: PRT

<213> ORGANISM: Solanum lycopersicum

<400> SEQUENCE: 5

Met Glu Gly Phe Thr Ser Phe Phe Asp Ser Gln Ser Ala Ser Arg Asn
1               5                   10                  15

Arg Trp Ser Tyr Asp Ser Leu Lys Asn Phe Arg Gln Ile Ser Pro Leu
            20                  25                  30

Val Gln Thr His Leu Lys Gln Val Tyr Leu Thr Leu Cys Cys Ala Leu
        35                  40                  45

Val Ala Ser Ala Ala Gly Ala Tyr Leu His Ile Leu Trp Asn Ile Gly
    50                  55                  60

Gly Leu Leu Thr Thr Met Ala Cys Met Gly Ser Met Val Trp Leu Leu
65                  70                  75                  80

Ser Ala Pro Pro Tyr Gln Glu Gln Lys Arg Val Ala Leu Leu Met Ala
                85                  90                  95

Ala Ala Leu Phe Glu Gly Ala Ser Ile Gly Pro Leu Ile Glu Leu Gly
            100                 105                 110

Ile Asn Phe Asp Pro Ser Ile Val Phe Gly Ala Phe Val Gly Cys Ala
        115                 120                 125

Val Val Phe Gly Cys Phe Ser Ala Ala Ala Met Leu Ala Arg Arg Arg
    130                 135                 140

Glu Tyr Leu Tyr Leu Gly Gly Leu Leu Ser Ser Gly Val Ser Leu Leu
145                 150                 155                 160

Phe Trp Leu His Phe Ala Ser Ser Ile Phe Gly Gly Ser Met Ala Val
                165                 170                 175

Phe Lys Phe Glu Leu Tyr Phe Gly Leu Leu Val Phe Val Gly Tyr Ile
            180                 185                 190

Val Phe Asp Thr Gln Glu Ile Ile Glu Lys Ala His Leu Gly Asp Met
        195                 200                 205

Asp Tyr Val Lys His Ala Leu Thr Leu Phe Thr Asp Phe Val Ala Val
    210                 215                 220

Phe Val Arg Ile Leu Ile Ile Met Leu Lys Asn Ala Ser Glu Lys Glu
225                 230                 235                 240

Glu Lys Lys Lys Lys Arg Arg Asn
                245

<210> SEQ ID NO 6
<211> LENGTH: 1127
<212> TYPE: DNA
<213> ORGANISM: Solanum lycopersicum

<400> SEQUENCE: 6
caacgcctta caggcagacg actttcgcat atcggtatag caaacataac attgtctacg      60
ttcagataaa tatcctttgc tcatttcagt tccaaaaact cgaagaagaa gaagaagaga     120
acaatggaag gtttcacatc gttcttcgac tcgcaatctg cctctcgcaa ccgctggagt     180
tatgattctc tcaaaaactt ccgccagatc tcacctctcg ttcaaactca tctcaagcag     240
gtgtacctta cgctatgctg tgctttagtg gcatcggctg ctgggcttta ccttcacatt     300
ctatggaata tcggtggcct cctcacaaca atggcttgca tgggaagcat ggtgtggctt     360
ctctcagctc ctccttatca agagcaaaaa agggtggctc ttctgatggc agctgcactt     420
tttgaaggcg cctctattgg tcctctgatt gagctgggca ttaacttcga tccaagcatt     480
gtgtttggcg cttttgtagg ttgtgctgtg gttttggtt gcttctcagc tgctgccatg     540
ttggcaaggc gcagggagta cttgtacctc gggggccttc tttcatctgg cgtctccctt     600

```
ctcttctggt tgcactttgc atcctccatt tttggtggtt ccatggctgt tttcaagttt    660
gagttgtatt ttggactctt ggtgtttgtg ggctacatcg tctttgacac ccaagaaatt    720
attgagaagg ctcacttggg tgatatggat tacgttaagc atgcattgac ccttttcaca    780
gattttgtcg ctgtttttgt gcggattctg atcatcatgt taaagaatgc atctgagaag    840
gaagagaaga agaagaagag gagaaactag atttgcttct caacttgtgg tttccataac    900
tccttgtgtt cacctgaaac aagcatgtta atagtttgat acttgcttca ctttagcata    960
ggctgtgatg taatgtcgtg tgacatgcca ttatggctgt gtgattgagc atctagcctt   1020
tttatcttct aaagcttttt tcttaacatt gataaggaaa gttccttgtg ataacattta   1080
agaccatttt aatttctcct ttctcattca aaaaaaaaaa aaaaaaa                  1127

<210> SEQ ID NO 7
<211> LENGTH: 248
<212> TYPE: PRT
<213> ORGANISM: Vitis vinifera

<400> SEQUENCE: 7

Met Glu Ala Phe Ser Ala Phe Phe Asp Ser Gln Ser Ser Ser Arg Ser
1               5                   10                  15

Gly Trp Thr Tyr Asp Ser Leu Lys Asn Phe Arg Gln Ile Ser Pro Ala
            20                  25                  30

Val Gln Thr His Leu Lys Gln Val Tyr Leu Ser Leu Cys Cys Ala Leu
        35                  40                  45

Ile Ala Ser Ala Ala Gly Ala Tyr Leu His Leu Leu Trp Asn Ile Gly
    50                  55                  60

Gly Leu Leu Thr Thr Phe Ala Cys Phe Gly Ser Ile Ile Trp Leu Leu
65                  70                  75                  80

Ser Ala Pro Ser Tyr Glu Glu Lys Lys Arg Val Ser Leu Leu Met Ala
                85                  90                  95

Val Ala Leu Phe Gln Gly Ala Ser Ile Gly Pro Leu Ile Asp Leu Ala
            100                 105                 110

Ile Glu Ile Asp Pro Ser Ile Leu Val Ser Ala Phe Val Gly Thr Ala
        115                 120                 125

Val Ala Phe Gly Cys Phe Ser Ala Ala Ala Met Leu Ala Arg Arg Arg
    130                 135                 140

Glu Tyr Leu Tyr Leu Gly Gly Val Leu Ser Ser Gly Leu Ser Ile Leu
145                 150                 155                 160

Phe Trp Leu His Phe Ala Ser Ser Leu Phe Gly Gly Ser Thr Ala Ile
                165                 170                 175

Phe Lys Phe Glu Leu Tyr Phe Gly Leu Leu Val Phe Gly Tyr Met
            180                 185                 190

Val Val Asp Thr Gln Asp Ile Ile Glu Lys Ala His Leu Gly Asp Arg
        195                 200                 205

Asp Tyr Val Lys His Ser Leu Leu Leu Phe Thr Asp Phe Ala Ala Val
    210                 215                 220

Phe Val Arg Ile Leu Ile Ile Met Leu Lys Asn Ser Ala Glu Lys Ser
225                 230                 235                 240

Glu Lys Lys Lys Lys Arg Arg Asn
                245

<210> SEQ ID NO 8
<211> LENGTH: 1097
<212> TYPE: DNA
```

<213> ORGANISM: Vitis vinifera

<400> SEQUENCE: 8

```
aaagaggatt gttggaatta ggttttcaat ggaggcgttc tctgcgtttt tcgattcaca      60
atcgagctca aggagcggtt ggacctacga ttcactcaag aatttccgcc agatttctcc     120
tgccgttcaa actcatctca agcaggttta tctctccctg tgctgtgcct tgattgcatc     180
tgctgcagga gcttacctgc atcttctctg gaatattggt ggccttctta ctacttttgc     240
atgctttgga agcatcatat ggctactctc tgcaccttca tatgaagaga aaagagggt     300
ttcactattg atggctgtgg ccctttttca aggagcctct atcggtcctt tgattgactt     360
ggctattgaa attgacccaa gcattcttgt tagtgctttt gtgggaactg cagtggcctt     420
tggctgtttc tctgcggctg caatgttggc aaggcgcaga gagtacctgt acttgggagg     480
ggttctttcg tctggcctct ccatcctttt ctggttgcac tttgcctcct cgttgtttgg     540
gggatccact gccatcttta agtttgagtt gtattttgga ctgttggtgt ttgtgggcta     600
catggtagta gacacccagg acataataga aaagcccat ctcggggatc gggactatgt      660
gaaacattct ctcctccttt tcactgattt tgctgcagtt tttgttcgaa tcctgattat     720
catgttgaag aactcggctg aaaagagtga agaagaagaa aaaggagaa attgaatgat      780
gggagactaa tgagcttaac ttgaactctg gttgaacaaa acaagagatt gtgtatgaac     840
ttgatgcttg tttctttctt tcccctaagt gagattatga tttttgaaac atgtgatacg     900
ctgggcgcta tggcagtgta catacgaatt gctcggttat gacattctgc atgtttaat      960
atatggggtt ggttttaaat aagaggacac tcgaatttgt tataatttga gaaacagttt    1020
gtatttcaaa atagaaacgg ttttctgtta aaaattcta atattgcaag gaaaattgaa     1080
tgtgatatat ttttttt                                                   1097
```

<210> SEQ ID NO 9
<211> LENGTH: 248
<212> TYPE: PRT
<213> ORGANISM: Capsicum annuum

<400> SEQUENCE: 9

```
Met Glu Gly Phe Thr Ser Phe Phe Glu Ser Gln Ser Ala Ser Arg Ser
1               5                   10                  15
Arg Trp Asn Tyr Asp Ala Leu Lys Asn Phe His Gln Ile Ser Pro Arg
            20                  25                  30
Val Gln Thr His Leu Lys Gln Val Tyr Leu Thr Leu Cys Cys Ala Leu
        35                  40                  45
Val Ala Ser Ala Ala Gly Ala Tyr Leu His Ile Leu Trp Asn Ile Gly
    50                  55                  60
Gly Phe Leu Thr Thr Leu Ala Cys Ile Gly Met Val Trp Leu Leu
65                  70                  75                  80
Ala Thr Pro Pro Tyr Gln Glu Gln Lys Arg Val Ala Leu Leu Met Ala
                85                  90                  95
Ala Ala Leu Phe Glu Gly Ala Ser Ile Gly Pro Leu Ile Glu Leu Gly
            100                 105                 110
Ile Asn Phe Asp Pro Ser Ile Val Leu Gly Ala Phe Val Gly Cys Gly
        115                 120                 125
Val Val Phe Gly Cys Phe Ser Ala Ala Met Leu Ala Arg Arg Arg
    130                 135                 140
Glu Tyr Leu Tyr Leu Gly Gly Leu Leu Ser Ser Gly Val Ser Leu Leu
145                 150                 155                 160
```

```
Met Trp Leu His Phe Ala Ser Ser Ile Phe Gly Gly Ala Met Ala Leu
            165                 170                 175

Phe Lys Phe Glu Val Tyr Phe Gly Phe Leu Val Phe Val Gly Tyr Ile
        180                 185                 190

Val Phe Asp Thr Gln Glu Ile Ile Glu Lys Ala His Leu Gly Asp Met
    195                 200                 205

Asp Tyr Val Lys His Ala Leu Thr Leu Phe Thr Asp Phe Val Ala Val
    210                 215                 220

Phe Val Arg Ile Leu Ile Ile Met Leu Lys Asn Ala Phe Glu Lys Glu
225                 230                 235                 240

Glu Lys Lys Lys Lys Arg Arg Asn
                245

<210> SEQ ID NO 10
<211> LENGTH: 747
<212> TYPE: DNA
<213> ORGANISM: Capsicum annuum

<400> SEQUENCE: 10
atggagggtt tcacgtcgtt cttcgaatcg caatcggctt ctcgcagtcg ctggaattat       60
gatgctctca aaacttcca tcagatctct cctcgtgttc aaactcatct caaacaggtc      120
tacctcacac tatgctgtgc tttagtcgca tcagctgctg ggcttacct tcacattctt      180 tggaacatcg gtggcttcct cacaacactg gcttgcattg aagcatggt gtggcttctg      240 gcaactcctc cttatcaaga gcaaaaaagg gtggcacttc tgatggcagc tgcactcttt      300
gaaggcgctt caattggtcc tctgattgaa ctgggcatca acttcgaccc aagcattgtg      360
cttggtgctt tgtaggttg tggtgtggtt tttggttgct tctcagctgc tgccatgttg      420
gcaaggcgca gggagtactt gtaccttgga ggccttcttt catctggtgt ctccctcctc      480
atgtggttgc actttgcatc ctccattttt ggtggtgcca tggccctttt caagtttgag      540
gtgtattttg gtttcttggt gtttgtgggc tacatagttt ttgacaccca agaaatcatt      600
gagaaggctc acttgggtga tatggattac gtcaagcatg cactcaccct cttcacagat      660
tttgttgcag tctttgtgcg gattttgatc atcatgttga gaatgcatt tgagaaggaa      720 gagaagaaga agaaggagag aaactag                                          747

<210> SEQ ID NO 11
<211> LENGTH: 244
<212> TYPE: PRT
<213> ORGANISM: Glycine max

<400> SEQUENCE: 11

Met Asp Ser Phe Asn Ser Phe Phe Asp Ser Thr Asn Arg Trp Asn Tyr
1               5                   10                  15

Asp Thr Leu Lys Asn Phe Arg Gln Ile Ser Pro Val Val Gln Asn His
            20                  25                  30

Leu Lys Gln Val Tyr Phe Thr Leu Cys Phe Ala Val Ala Ala Ala
        35                  40                  45

Val Gly Ala Tyr Leu His Val Leu Leu Asn Ile Gly Gly Phe Leu Thr
    50                  55                  60

Thr Val Ala Cys Val Gly Ser Ser Val Trp Leu Leu Ser Thr Pro Pro
65                  70                  75                  80

Phe Glu Glu Arg Lys Arg Val Thr Leu Leu Met Ala Ala Ser Leu Phe
                85                  90                  95
```

-continued

Gln Gly Ala Ser Ile Gly Pro Leu Ile Asp Leu Ala Ile Gln Ile Asp
                100                 105                 110

Pro Ser Leu Ile Phe Ser Ala Phe Val Gly Thr Ser Leu Ala Phe Ala
        115                 120                 125

Cys Phe Ser Gly Ala Ala Leu Val Ala Arg Arg Glu Tyr Leu Tyr
    130                 135                 140

Leu Gly Gly Leu Val Ser Ser Gly Leu Ser Ile Leu Leu Trp Leu His
145                 150                 155                 160

Phe Ala Ser Ser Ile Phe Gly Gly Ser Thr Ala Leu Phe Lys Phe Glu
                165                 170                 175

Leu Tyr Phe Gly Leu Leu Val Phe Val Gly Tyr Ile Val Val Asp Thr
            180                 185                 190

Gln Glu Ile Val Glu Arg Ala His Leu Gly Asp Leu Asp Tyr Val Lys
        195                 200                 205

His Ala Leu Thr Leu Phe Thr Asp Leu Val Ala Val Phe Val Arg Ile
    210                 215                 220

Leu Val Ile Met Leu Lys Asn Ser Ala Glu Arg Asn Glu Lys Lys Lys
225                 230                 235                 240

Lys Arg Arg Asp

<210> SEQ ID NO 12
<211> LENGTH: 1077
<212> TYPE: DNA
<213> ORGANISM: Glycine max

<400> SEQUENCE: 12
tttttttttt ttttttttaa cgtaaaaatt tatcttatta gagaactcaa aacatgtcaa      60
catgtactag tgtactactg atataaagca aacaaacgac taaactgcac agttggagca     120
agcttaacaa gtgaacaaca ctgtatagac agctgtttta agtattacag tccaagggag     180
ttgaagtgtt aactgagcag attggtaaga aaatcaatct ctcctcttct ttttcttctc     240
attcctctca gccgaattct tcaacataat aacaagaatc cggacaaaaa ctgcaaccaa     300
atcggtaaac aaggtcaagg catgctttac atagtccaga tcgcccaagt gtgccctctc     360
aactatttct tgggtgtcta ctacaatgta acctacaaac accaaaagcc caaagtacaa     420
ctcaaactta agagagctg ttgaacctcc aaagatggaa gaagcaaagt gcaaccagag     480
aaggatggac aatccagaag aaaccaagcc accaaggtac aggtactccc tacgcctagc     540
aaccaaagct gctcctgaga agcatgcaaa ggccaaggat gttcccacaa atgcactaaa     600
gataaggctt ggatcgattt gaatagccaa atctatcaag ggtccaatag aggcaccctg     660
aaacagtgat gcggccatca acaaagtcac tcttttcctc tcttcaaaag gaggtgtcga     720
gagtaaccaa acactgcttc ccacgcatgc cactgtagta agaaaacccc caatgttcaa     780
gaggacatga aggtaagccc caacagccgc agcaaccacg gcgaaacaca gagtaaaata     840
aacctgcttg aggtgattct gaacgaccgg agaaatttga cggaagtttt tgagagtatc     900
gtaattccat cggtttgttg aatcgaagaa ggaattgaag gagtccattg cttgcaatcg     960
gagaaacaca aatttggtta atgacggata tggctttgaa tttcaacacc cctaatttat    1020
acttcaatca agggaccaac gaaggctaat ttcgcagaag gttccactta agattcc      1077

<210> SEQ ID NO 13
<211> LENGTH: 258
<212> TYPE: PRT
<213> ORGANISM: Sorghum bicolor

<400> SEQUENCE: 13

```
Met Asp Ala Phe Tyr Ser Thr Ser Ser Ser Ser Ser Ser Gly Pro
1               5                   10                  15

Tyr Gly Ala Ala Ala Tyr Gly Gly Ser Gly Trp Gly Tyr Asp Ser Leu
            20                  25                  30

Lys Asn Phe Arg Gln Ile Ser Pro Ala Val Gln Thr His Leu Lys Leu
            35                  40                  45

Val Tyr Leu Thr Leu Cys Val Ala Leu Ala Ser Ser Ala Leu Gly Ala
        50                  55                  60

Tyr Leu His Val Val Trp Asn Ile Gly Gly Met Leu Thr Met Leu Gly
65                  70                  75                  80

Cys Val Gly Ser Ile Ala Trp Leu Phe Ser Val Pro Val Tyr Glu Glu
                85                  90                  95

Arg Lys Arg Tyr Gly Leu Leu Met Ala Ala Leu Leu Glu Gly Ala
                100                 105                 110

Ser Val Gly Pro Leu Ile Lys Leu Ala Val Glu Phe Asp Pro Ser Ile
            115                 120                 125

Leu Val Thr Ala Phe Val Gly Thr Ala Ile Ala Phe Ala Cys Phe Ser
        130                 135                 140

Cys Ala Ala Val Val Ala Lys Arg Arg Glu Tyr Leu Tyr Leu Gly Gly
145                 150                 155                 160

Leu Leu Ser Ser Gly Leu Ser Ile Leu Leu Trp Leu Gln Phe Ala Ala
                165                 170                 175

Ser Ile Phe Gly His Ser Thr Ser Thr Phe Met Phe Glu Val Tyr Phe
            180                 185                 190

Gly Leu Leu Ile Phe Leu Gly Tyr Met Val Tyr Asp Thr Gln Glu Ile
            195                 200                 205

Ile Glu Arg Ala His His Gly Asp Met Asp Tyr Ile Lys His Ala Leu
            210                 215                 220

Thr Leu Phe Thr Asp Phe Val Ala Val Leu Val Arg Ile Leu Val Ile
225                 230                 235                 240

Met Leu Lys Asn Ala Ala Asp Lys Ser Glu Asp Lys Lys Arg Lys Lys
                245                 250                 255

Arg Ser
```

<210> SEQ ID NO 14
<211> LENGTH: 1326
<212> TYPE: DNA
<213> ORGANISM: Sorghum bicolor

<400> SEQUENCE: 14

```
agatcaaatc aaatccacga gacgagaaca aaacctggtt ccgacccagc acgagacacg    60
actcctccat tccaaatcca atccatcca  ttcccccttt gcgtgtggtg cgaggcccac   120
cgatcccatc cgatccgatc catttcgcgt cgcgtctacc agagggatca cgacacaccc   180
gccgccggag ccggaagaga gagagagaga gatggacgcg ttctactcga cctcctcgtc   240
gtcgtcgtcc tcggggccgt acggcgcggc ggcgtacggc ggcagcggct ggggctacga   300
ctcgctcaag aacttccgcc agatcagccc cgccgtccag acccacctca agctcgttta   360
cctgaccctc tgcgtggcgc tggcctcgtc ggcgctgggc gcttacctgc acgtcgtctg   420
gaacatcggc gggatgctga ccatgctcgg ctgcgtcggc agtatcgcct ggctcttctc   480
ggtgcccgtc tacgaggaga ggaagaggta cggactgctg atggcggctg ccctcctgga   540
aggggcttcg gttggacccc tcatcaagct ggccgtggaa tttgacccaa gcatcctggt   600
```

```
gacagcgttt gtgggaactg ccattgcgtt cgcgtgcttc tcttgcgcgg ccgtggttgc    660
caagcgcagg gagtacctct acctgggcgg gctgctctct tcggggctct ccatcctgct    720
ctggctgcag ttcgccgcct ccatctttgg ccactccact agcaccttca tgtttgaggt    780
ttactttggg ctgcttatct tcctgggata catggtgtac gacacgcagg agatcatcga    840
gagggcgcac cacggcgaca tggactacat caagcacgcc ctcaccctct tcaccgactt    900
cgtggctgtc cttgtccgca tcctcgtcat catgctcaag aacgcggctg acaagtcgga    960
ggacaagaag aggaagaaga ggtcgtgagc ggtctcacct gtgcgtaagt gcaacactga   1020
aggaaggaaa ggcacggcgg gctgcctgct gctactagta gtacaatata tatgaatatg   1080
aatcgaagct cctgcatatt atatataggg ggagtaactg ggtgcttgtg atggaactga   1140
aagaaagtgt ttcttcgttt tcttgctctc ttattagtct gttagttgtc ctgtaaattg   1200
agtctggtaa ggttttgttg cataaacgat acgagcgctg caacaaattg gatctgcttg   1260
ccggtgtttt ccggcctgaa aactctgaag atggatggaa tgcgattaag aatgttgcct   1320
ttgcac                                                              1326
```

<210> SEQ ID NO 15
<211> LENGTH: 252
<212> TYPE: PRT
<213> ORGANISM: Zea mays

<400> SEQUENCE: 15

```
Met Asp Ala Phe Phe Ser Ala Ser Ser Ala Ser Ala Pro Tyr Gly Tyr
1               5                   10                  15

Gly Ala Gly Gly Trp Ser Tyr Asp Ser Leu Lys Asn Phe Arg Gln Ile
            20                  25                  30

Thr Pro Ala Val Gln Thr His Leu Lys Leu Val Tyr Leu Thr Leu Cys
        35                  40                  45

Ala Ala Leu Ala Ser Ser Ala Val Gly Ala Tyr Leu His Val Val Trp
    50                  55                  60

Asn Ile Gly Gly Thr Leu Thr Met Leu Gly Cys Val Gly Ser Ile Ala
65                  70                  75                  80

Trp Leu Phe Ser Val Pro Val Tyr Glu Glu Arg Lys Arg Tyr Gly Leu
                85                  90                  95

Leu Met Ala Ala Ala Leu Leu Glu Gly Ala Ser Val Gly Pro Leu Val
            100                 105                 110

Lys Leu Ala Val Glu Phe Asp Pro Ser Ile Leu Val Thr Ala Phe Val
        115                 120                 125

Gly Thr Ala Ile Ala Phe Ala Cys Phe Thr Gly Ala Ala Met Val Ala
    130                 135                 140

Arg Arg Arg Glu Tyr Leu Tyr Leu Gly Gly Leu Leu Ser Ser Gly Leu
145                 150                 155                 160

Ser Ile Leu Leu Trp Leu Gln Leu Ala Gly Ser Ile Phe Gly His Ser
                165                 170                 175

Ala Thr Ser Phe Met Phe Glu Val Tyr Phe Gly Leu Leu Ile Phe Leu
            180                 185                 190

Gly Tyr Val Val Tyr Asp Thr Gln Glu Ile Ile Glu Arg Ala His Arg
        195                 200                 205

Gly Asp Met Asp His Val Lys His Ala Leu Thr Leu Phe Thr Asp Phe
    210                 215                 220

Val Ala Val Leu Val Arg Val Leu Val Ile Met Leu Lys Asn Gly Ala
225                 230                 235                 240
```

Asp Lys Ser Glu Asp Lys Lys Arg Lys Lys Arg Ser
                245                 250

<210> SEQ ID NO 16
<211> LENGTH: 1173
<212> TYPE: DNA
<213> ORGANISM: Zea mays

<400> SEQUENCE: 16
tcgtccttct ccttcccacc gccacgccac gccacgccac gccggctcgg tacatatact      60
agcctgcctc gatcggcctc cctcgcattc cccctcgatc ggcctccctc ccccaagatc     120
ctccactcga tcccaaacaa accaacaaat ccatccatcg cacatggacg cgttcttctc     180
ggcctcctcc gcgtcggcgc cctacggcta cggcgccggc ggatggagct acgactcgct     240
caagaacttc cgccagatca cccccgccgt ccagacccac ctcaagctcg tctacctcac     300
cctgtgcgcg gcgctggcct cgtcggcggt gggcgcttac ctgcacgtgg tctggaacat     360
cggcggtacg ctgacaatgc tcggttgcgt cggcagcatc gcctggctct ctcggtgcc      420
cgtctacgag gagaggaaga ggtatgggct gctgatggcg gctgccctcc tggaaggcgc     480
ttcggtcgga cccctcgtca agctcgccgt ggaatttgac ccaagcatcc tggtgacggc     540
gttcgtgggg actgccatcg cgttcgcgtg cttcaccggc gcggccatgg tggccaggcg     600
cagggagtac ctctacctgg gtgggctgct ctcgtcgggg ctctccatcc tgctctggct     660
gcagctagcc ggctccatct tcggccactc cgcaaccagc ttcatgttcg aggtctactt     720
cgggctgctc atcttcctgg gctacgtggt gtacgacacg caggagatca tcgagagggc     780
gcaccgcggc gacatggacc acgtcaagca cgccctcacc ctcttcacag acttcgtggc     840
cgtcctcgtc cgcgtcctcg tcatcatgct caagaacggg gccgacaagt cggaggacaa     900
gaagaggaag aagaggtcgt gagcgcgtcg agaagggaag ctcttccact ccacatatg      960
cataggagta actgctgggg ttccttcctg gggtggaagt gtggaactga gctgagtgtt    1020
cagaagtgtt cctttgttcg gcacctttgt tctcttcctc tcttgatgag tctgtaaata    1080
gctatgtcaa tctggttaag cttggtttgg ttgcctgtgc ctgtgttcgc tggcctttgg    1140
atagaatgca aattaaagat gttgctattg cac                                 1173

<210> SEQ ID NO 17
<211> LENGTH: 247
<212> TYPE: PRT
<213> ORGANISM: Triticum aestivum

<400> SEQUENCE: 17

Met Asp Ala Phe Tyr Ser Thr Ser Ala Ala Ala Ser Gly Trp Gly
1               5                   10                  15

Tyr Asp Ser Leu Lys Asn Phe Arg Glu Ile Ser Pro Ala Val Gln Ser
                20                  25                  30

His Leu Lys Leu Val Tyr Leu Thr Leu Cys Phe Ala Leu Ala Ser Ser
            35                  40                  45

Ala Val Gly Ala Tyr Leu His Ile Ala Leu Asn Ile Gly Gly Met Leu
        50                  55                  60

Thr Met Leu Ala Cys Ile Gly Thr Ile Ala Trp Met Phe Ser Val Pro
65                  70                  75                  80

Val Tyr Glu Glu Arg Lys Arg Phe Gly Leu Leu Met Gly Ala Ala Leu
                85                  90                  95

Leu Glu Gly Ala Ser Val Gly Pro Leu Ile Glu Leu Ala Ile Asp Phe

Asp Pro Ser Ile Leu Val Thr Gly Phe Val Gly Thr Ala Ile Ala Phe
                100                 105                 110

Gly Cys Phe Ser Gly Ala Ala Ile Ala Lys Arg Arg Glu Tyr Leu
        115                 120                 125

Tyr Leu Gly Gly Leu Leu Ser Ser Gly Leu Ser Ile Leu Leu Trp Leu
130                 135                 140

145                 150                 155                 160

Gln Phe Ala Thr Ser Ile Phe Gly His Ser Gly Ser Phe Met Phe
                165                 170                 175

Glu Val Tyr Phe Gly Leu Leu Ile Phe Leu Gly Tyr Met Val Tyr Asp
                180                 185                 190

Thr Gln Glu Ile Ile Glu Arg Ala His His Gly Asp Met Asp Tyr Ile
                195                 200                 205

Lys His Ala Leu Thr Leu Phe Thr Asp Phe Val Ala Val Leu Val Arg
        210                 215                 220

Ile Leu Ile Ile Met Leu Lys Asn Ala Gly Asp Lys Ser Glu Asp Lys
225                 230                 235                 240

Lys Lys Arg Lys Arg Arg Ser
                245

<210> SEQ ID NO 18
<211> LENGTH: 744
<212> TYPE: DNA
<213> ORGANISM: Triticum aestivum

<400> SEQUENCE: 18
atggacgcct tctactcgac ctcgtcggcg gcggccagcg gatggggcta cgactccctc        60
aagaacttcc gcgagatctc ccccgccgtg cagtcccacc tcaagctcgt ttacctgacc      120
ctatgctttg ccctggcctc atctgccgtg ggtgcttacc tgcacattgc cctgaacatt      180
ggcgggatgc tgacaatgct cgcgtgtatc ggaaccatcg cctggatgtt ctcggtgcca      240
gtctatgagg agaggaagag gtttgggctg ctgatgggtg cagccctcct ggaaggggct      300
tcagttggac ctctgattga gcttgccata gactttgacc caagcatcct cgtgacaggg      360
tttgtcggaa ccgccatcgc cttcgggtgc ttctctggcg ccgccatcat cgccaagcgc      420
agggagtacc tgtacctcgg cggcctgctc tcctctggcc tgtcgatcct gctctggctg      480
cagtttgcca cgtccatctt tggccactcc tctggcagct tcatgtttga ggtctacttt      540
ggcctgttga tcttcctggg gtacatggtg tacgacacgc aggagatcat cgagagggcg      600
caccacggtg acatggacta catcaagcac gcgctcaccc tcttcaccga cttcgtcgcc      660
gtcctcgtcc gcatcctcat catcatgctc aagaacgcag gcgacaagtc ggaggacaag      720
aagaagagga gaggaggtc ctga                                              744

<210> SEQ ID NO 19
<211> LENGTH: 247
<212> TYPE: PRT
<213> ORGANISM: Triticum aestivum

<400> SEQUENCE: 19

Met Asp Ala Phe Tyr Ser Thr Ser Ala Ala Ala Ser Gly Trp Gly
1               5                   10                  15

Tyr Asp Ser Leu Lys Asn Phe Arg Glu Ile Ser Pro Ala Val Gln Ser
                20                  25                  30

His Leu Lys Leu Val Tyr Leu Thr Leu Cys Phe Ala Leu Ala Ser Ser
        35                  40                  45

Ala Val Gly Ala Tyr Leu His Ile Ala Leu Asn Ile Gly Gly Met Leu
    50                  55                  60

Thr Met Leu Ala Cys Val Gly Thr Ile Ala Trp Met Phe Ser Val Pro
65                  70                  75                  80

Val Tyr Glu Glu Arg Lys Arg Phe Gly Leu Leu Met Gly Ala Ala Leu
                85                  90                  95

Leu Glu Gly Ala Ser Val Gly Pro Leu Ile Glu Leu Ala Ile Asp Phe
            100                 105                 110

Asp Pro Ser Ile Leu Val Thr Gly Phe Val Gly Thr Ala Ile Ala Phe
            115                 120                 125

Gly Cys Phe Ser Gly Ala Ala Ile Ile Ala Lys Arg Arg Glu Tyr Leu
        130                 135                 140

Tyr Leu Gly Gly Leu Leu Ser Ser Gly Leu Ser Ile Leu Leu Trp Leu
145                 150                 155                 160

Gln Phe Ala Thr Ser Ile Phe Gly His Ser Ser Gly Ser Phe Met Phe
                165                 170                 175

Glu Val Tyr Phe Gly Leu Leu Ile Phe Leu Gly Tyr Met Val Tyr Asp
            180                 185                 190

Thr Gln Glu Ile Ile Glu Arg Ala His His Gly Asp Met Asp Tyr Ile
            195                 200                 205

Lys His Ala Leu Thr Leu Phe Thr Asp Phe Val Ala Val Leu Val Arg
        210                 215                 220

Ile Leu Ile Ile Met Leu Lys Asn Ala Gly Asp Lys Ser Glu Asp Lys
225                 230                 235                 240

Lys Lys Arg Lys Arg Arg Ser
                245

<210> SEQ ID NO 20
<211> LENGTH: 744
<212> TYPE: DNA
<213> ORGANISM: Triticum aestivum

<400> SEQUENCE: 20
atggacgcct tctactcgac ctcgtcggcg gcggcgagcg gctggggcta cgactccctc     60
aagaacttcc gcgagatctc ccccgccgtg cagtcccacc tcaagctcgt ttacctgacc    120
ctatgctttg ccctggcctc atctgccgtg ggtgcttacc tgcacattgc cctgaacatc    180
ggtgggatgc tgacaatgct cgcgtgtgtt ggaaccatcg cctggatgtt ctctgtgcca    240
gtctatgagg agaggaagag gtttgggctg ctgatgggtg cagccctcct ggaaggggct    300
tcggttggac tctgattga gcttgccata gactttgacc caagtatcct cgtgacaggg    360
tttgtcggaa ccgccatcgc cttcgggtgc ttctctggcg ccgccatcat cgccaagcgc    420
agggagtacc tgtacctcgg tggcctgctc tcctccggcc tgtcgatcct gctctggctg    480
cagtttgcca cgtccatctt tggccactcc tctggcagct tcatgtttga ggtttacttt    540
ggcctgttga tctttctggg atacatggtg tacgacacgc aggagatcat cgagagggcg    600
caccacggcg acatggacta catcaagcac gcgctcaccc tcttcaccga ctttgtcgcc    660
gtcctcgtcc ggatcctcat catcatgctc aagaacgcag gcgacaagtc ggaggacaag    720
aagaagagga gaggaggtc ctga                                             744

<210> SEQ ID NO 21
<211> LENGTH: 246
<212> TYPE: PRT
<213> ORGANISM: Glycine max

<400> SEQUENCE: 21

Met Asp Thr Phe Phe Lys Ser Pro Ser Ser Ser Ser Arg Ser Ser
1               5                   10                  15

Trp Ser Tyr Asp Thr Leu Lys Asn Phe Arg Glu Ile Ser Pro Leu Val
            20                  25                  30

Gln Asn His Ile Lys Leu Val Tyr Phe Thr Leu Cys Cys Ala Val Val
        35                  40                  45

Ala Ala Ala Val Gly Ala Phe Leu His Val Leu Trp Asn Ile Gly Gly
    50                  55                  60

Phe Leu Thr Thr Val Ala Ser Ile Gly Ser Met Phe Trp Leu Leu Ser
65              70                  75                  80

Thr Pro Pro Phe Glu Glu Gln Lys Arg Leu Ser Leu Leu Met Ala Ser
                85                  90                  95

Ala Leu Phe Gln Gly Ala Ser Ile Gly Pro Leu Ile Gly Leu Ala Phe
            100                 105                 110

Ala Ile Asp Pro Gly Leu Ile Ile Gly Ala Phe Val Ala Thr Ser Leu
        115                 120                 125

Ala Phe Ala Cys Phe Ser Ala Val Ala Leu Val Ala Arg Arg Arg Glu
    130                 135                 140

Tyr Pro Tyr Leu Gly Gly Leu Leu Ser Ser Trp Leu Ser Ile Leu Met
145                 150                 155                 160

Trp Leu His Ser Asp Ser Ser Leu Phe Gly Gly Ser Ile Ala Leu Phe
                165                 170                 175

Lys Phe Glu Leu Tyr Phe Gly Leu Leu Val Phe Val Gly Tyr Val Ile
            180                 185                 190

Val Asp Thr Gln Val Ile Ile Glu Arg Ala His Phe Gly Asp Leu Asp
        195                 200                 205

Tyr Val Lys His Ala Leu Thr Leu Phe Thr Asp Leu Ala Ala Ile Phe
    210                 215                 220

Val Arg Ile Leu Asn Ile Met Leu Asn Asn Ser Ser Lys Arg Asn Glu
225                 230                 235                 240

Lys Lys Arg Arg Arg Asp
                245

<210> SEQ ID NO 22
<211> LENGTH: 1051
<212> TYPE: DNA
<213> ORGANISM: Glycine max

<400> SEQUENCE: 22
tttttttttt tttttgaaa caaaggcagt aaataatcat ttggaagaac ctgtccgcaa       60
gtttatacta tatattatga ttattagcaa atacatatga aaatgtttaa aagaaatcct     120
gacatttacc attacagcaa acacatagct aactactaac tacacaaggg gaccaacaac     180
ttctaaacag ctaattatgt attctctaca aaccaaatta ctctacacat agcaatcggt     240
caacctatta atctctcctc ctcttcttct catttctctt agatgaatta ttcaacatta     300
tattaagaat tcgcacaaag attgcagcca aatcagtgaa cagtgtcaat gcatgcttaa     360
cataatccag gtcaccaaag tgagccctct caatgattac ttgagtgtct actataacgt     420
agcccacaaa caccaaaagc ccaaagtaca actcaaattt gaatagagct atagagcccc     480
caaagagaga ggaatcagag tgcaaccaca taagaatgga aagccaagaa gaaagcaaac     540
caccaaggta ggggtactcc cttcgccttg caactaaggc tactgcagaa aagcaagcaa     600

```
aagccaaaga agttgccaca aatgcgccaa tgataaggcc aggatcaatg gcaaaagcca      660
aaccaatcag aggtccaatg gaagcaccct gaaacagggc cgaagccatc aacagagaca      720
acctcttctg ctcttcaaaa gggggtgtag atagcaacca aaacatgctc ccaatggaag      780
ccaccgtggt gagaaaaccg ccaatgttcc acagaacatg aaggaaggct ccaacagcag      840
cagccaccac agcgcaacat aacgtaaaat aaaccagttt gatgtgattc tgaacgagcg      900
gagagatctc gcggaaattc ttgagagtat cgtaactcca gctgcttcta aagaagaag       960 acgatgggga cttgaagaaa gtgtccatcg aaaacaagga atcaaatcgt atcgttttcg     1020
tgatgtgatt attacaagca caattggttc c                                    1051

<210> SEQ ID NO 23
<211> LENGTH: 247
<212> TYPE: PRT
<213> ORGANISM: Hordeum vulgare

<400> SEQUENCE: 23

Met Asp Ala Phe Tyr Ser Thr Ser Ser Ala Ala Ala Ser Gly Trp Gly
1               5                   10                  15

His Asp Ser Leu Lys Asn Phe Arg Gln Ile Ser Pro Ala Val Gln Ser
            20                  25                  30

His Leu Lys Leu Val Tyr Leu Thr Leu Cys Phe Ala Leu Ala Ser Ser
        35                  40                  45

Ala Val Gly Ala Tyr Leu His Ile Ala Leu Asn Ile Gly Gly Met Leu
    50                  55                  60

Thr Met Leu Ala Cys Val Gly Thr Ile Ala Trp Met Phe Ser Val Pro
65                  70                  75                  80

Val Tyr Glu Glu Arg Lys Arg Phe Gly Leu Leu Met Gly Ala Leu
                85                  90                  95

Leu Glu Gly Ala Ser Val Gly Pro Leu Ile Glu Leu Ala Ile Asp Phe
            100                 105                 110

Asp Pro Ser Ile Leu Val Thr Gly Phe Val Gly Thr Ala Ile Ala Phe
        115                 120                 125

Gly Cys Phe Ser Gly Ala Ala Ile Ile Ala Lys Arg Arg Glu Tyr Leu
    130                 135                 140

Tyr Leu Gly Gly Leu Leu Ser Ser Gly Leu Ser Ile Leu Leu Trp Leu
145                 150                 155                 160

Gln Phe Ala Thr Ser Ile Phe Gly His Ser Ser Gly Ser Phe Met Phe
                165                 170                 175

Glu Val Tyr Phe Gly Leu Leu Ile Phe Leu Gly Tyr Met Val Tyr Asp
            180                 185                 190

Thr Gln Glu Ile Ile Glu Arg Ala His His Gly Asp Met Asp Tyr Ile
        195                 200                 205

Lys His Ala Leu Thr Leu Phe Thr Asp Phe Val Ala Val Leu Val Arg
    210                 215                 220

Val Leu Ile Ile Met Leu Lys Asn Ala Gly Asp Lys Ser Glu Asp Lys
225                 230                 235                 240

Lys Lys Arg Lys Arg Arg Ser
                245

<210> SEQ ID NO 24
<211> LENGTH: 1177
<212> TYPE: DNA
<213> ORGANISM: Hordeum vulgare

<400> SEQUENCE: 24
```

-continued

```
gagcggagaa ggcgaaaaac agaaggagaa aaatccaccc caaaacgcga gcgcaggaca      60
agcgaggaac cttgcgtgcg aggcgaggcc gccccgctcc gattcgattc gacgcgcagg     120
cgcaggcgca gggatggacg ccttctactc gacctcgtcg gcggcggcga gcggctgggg     180
ccacgactcc ctcaagaact tccgccagat ctcccccgcc gtgcagtccc acctcaagct     240
cgtttacctg actctatgct ttgcactggc ctcatctgcc gtgggtgctt acctacacat     300
tgccctgaac atcggcggga tgctgacaat gctcgcttgt gtcggaacta tcgcctggat     360
gttctcggtg ccagtctatg aggagaggaa gaggtttggg ctgctgatgg gtgcagccct     420
cctggaaggg gcttcggttg gacctctgat tgagcttgcc atagactttg acccaagcat     480
cctcgtgaca gggtttgtcg gaaccgccat cgcctttggg tgcttctctg cgccgccat      540
catcgccaag cgcagggagt acctgtacct cggtggcctg ctctcgtctg gcctgtcgat     600
cctgctctgg ctgcagtttg ccacgtccat ctttggccac tcctctggca gcttcatgtt     660
tgaggtttac tttggcctgt tgatcttcct ggggtacatg gtgtacgaca cgcaggagat     720
catcgagagg gcgcaccatg gcgacatgga ctacatcaag cacgccctca ccctcttcac     780
cgactttgtt gccgtcctcg tccgagtcct catcatcatg ctcaagaacg caggcgacaa     840
gtcggaggac aagaagaaga ggaagaggag gtcctgaacg ttttttcccgc acatgtagat    900
accgtcaccg ccgccgctac tggtaccccc cccccgcta agtacgtagt aggaattaag     960
ctggcgcagt aacttggcgc cgtgccatcc ttgttaattt gtgttcgtgt gaaccttgtg    1020
tgagtctgct gctgctgatg aagcttttgc agccgcccgt ctgcgttccg aatctcttgt    1080
gttgttgtta ctgtcaggat aatgaatcga acgaaacctg agacgatttg gttttggttt    1140
ggtttgcgaa gaacatggct acgcttgttt gtgaatg                             1177
```

<210> SEQ ID NO 25
<211> LENGTH: 249
<212> TYPE: PRT
<213> ORGANISM: Oryza sativa

<400> SEQUENCE: 25

```
Met Asp Ala Phe Tyr Ser Thr Ser Ser Ala Tyr Gly Ala Ala Ala Ser
1               5                   10                  15

Gly Trp Gly Tyr Asp Ser Leu Lys Asn Phe Arg Gln Ile Ser Pro Ala
            20                  25                  30

Val Gln Ser His Leu Lys Leu Val Tyr Leu Thr Leu Cys Val Ala Leu
        35                  40                  45

Ala Ala Ser Ala Val Gly Ala Tyr Leu His Val Ala Leu Asn Ile Gly
    50                  55                  60

Gly Met Leu Thr Met Leu Gly Cys Val Gly Ser Ile Ala Trp Leu Phe
65                  70                  75                  80

Ser Val Pro Val Phe Glu Glu Arg Lys Arg Phe Gly Ile Leu Leu Ala
                85                  90                  95

Ala Ala Leu Leu Glu Gly Ala Ser Val Gly Pro Leu Ile Lys Leu Ala
            100                 105                 110

Val Asp Phe Asp Ser Ser Ile Leu Val Thr Ala Phe Val Gly Thr Ala
        115                 120                 125

Ile Ala Phe Gly Cys Phe Thr Cys Ala Ala Ile Val Ala Lys Arg Arg
    130                 135                 140

Glu Tyr Leu Tyr Leu Gly Gly Leu Leu Ser Ser Gly Leu Ser Ile Leu
145                 150                 155                 160
```

```
Leu Trp Leu Gln Phe Ala Ala Ser Ile Phe Gly His Ser Thr Gly Ser
            165                 170                 175

Phe Met Phe Glu Val Tyr Phe Gly Leu Leu Ile Phe Leu Gly Tyr Met
            180                 185                 190

Val Tyr Asp Thr Gln Glu Ile Ile Glu Arg Ala His His Gly Asp Met
        195                 200                 205

Asp Tyr Ile Lys His Ala Leu Thr Leu Phe Thr Asp Phe Val Ala Val
    210                 215                 220

Leu Val Arg Ile Leu Val Ile Met Leu Lys Asn Ala Ser Asp Lys Ser
225                 230                 235                 240

Glu Glu Lys Lys Arg Lys Lys Arg Ser
                245

<210> SEQ ID NO 26
<211> LENGTH: 1191
<212> TYPE: DNA
<213> ORGANISM: Oryza sativa

<400> SEQUENCE: 26
ttccttttta tccgacgatt caaaaaattc gaagccatcc accaacgaag aaaaaaaaaa      60
gggagaaaaa aaaatccacg cacactttgc gtgcgaggcg aggcggttcg attcgagagg     120
agagagagag agagagagag agagagagat ggacgccttc tactcgacct cgtcggcgta     180
cggagcggcg gcgagcggct ggggctacga ctcgctgaag aacttccgcc agatctcccc     240
cgccgtccag tcccacctca agctcgttta cctgacacta tgcgtcgccc tggctgcgtc     300
ggcggtgggc gcatacctgc acgtcgcctt gaacatcggc gggatgttga ctatgctcgg     360
gtgcgtgggg agcatcgcct ggttgttctc ggtgcctgtc tttgaggaga ggaagaggtt     420
tgggattctc ttggccgctg ccctgctgga aggggcttca gttgggcctc tgatcaagct     480
tgctgtagac tttgactcaa gcattctcgt aacagcattt gttggaactg ccattgcatt     540
tgggtgcttc acttgcgctg ccatcgttgc aagcgtagg gagtacctct accttggtgg     600
tttgctctct tctggcctct ccatcctgct ctggctgcag tttgccgcat ccatctttgg     660
ccactccacc ggcagcttca tgtttgaggt ttactttggc ctgttgatct tcctgggta     720
catggtgtat gacacgcagg agatcatcga gagggctcac cacggtgaca tggactacat     780
caagcacgca ctcaccctct tcactgactt cgtggccgtc cttgtccgga tcctcgtcat     840
catgctcaag aacgcgtctg acaagtcgga ggagaagaag aggaagaaga ggtcttgaga     900
gcttctcttc ccgctttgca cataagaaaa aaccaccgcg gctattgcct ctacgtatta     960
tgacagagcc gcacttcaac tgggttttat ggtgaataca agttcttttg cattttgttg    1020
atacggtgtg aatcttctca ggtttgtcgt cgtagtagct ttgcaaatac tagcatgcta    1080
catgacacgg atctttctgt aatggtggtc gcgttgatcg aaacgtgaaa acacatcttc    1140
atttgcgact aatttgtttg ccttttggtg attgatgatg atcctttccc c             1191

<210> SEQ ID NO 27
<211> LENGTH: 250
<212> TYPE: PRT
<213> ORGANISM: Cucumis sativus

<400> SEQUENCE: 27

Met Asp Ala Phe Ser Ser Phe Phe Asp Ser Gln Ser Gly Ser Arg Thr
1               5                   10                  15

Arg Trp Ser His Glu Ser Leu Lys Asn Phe Arg Gln Ile Ser Pro Ala
            20                  25                  30
```

Val Gln Ser His Leu Gln Arg Val Tyr Leu Thr Leu Gly Cys Ala Leu
            35                  40                  45

Val Ala Ser Ala Ala Gly Ala Tyr Leu His Ile Leu Trp Asn Ile Gly
    50                  55                  60

Gly Phe Leu Thr Thr Leu Ala Thr Ile Gly Cys Ile Thr Trp Leu Met
65                  70                  75                  80

Ala Thr Pro Pro Tyr Glu Glu Lys Lys Arg Ala Ser Ile Leu Leu Gly
                85                  90                  95

Ala Ala Leu Leu Glu Gly Ala Ser Ile Gly Pro Leu Ile Ser Leu Ala
            100                 105                 110

Ile Asp Phe Asp Pro Ser Val Leu Val Ser Ala Phe Val Gly Thr Ala
            115                 120                 125

Val Ala Phe Cys Cys Phe Ser Gly Ala Ala Leu Leu Ala Arg Arg Arg
        130                 135                 140

Glu Phe Leu Tyr Leu Gly Gly Leu Leu Ser Ser Gly Val Ser Met Leu
145                 150                 155                 160

Leu Trp Leu His Phe Ala Ser Ser Leu Phe Gly Gly Ser Thr Ala Leu
                165                 170                 175

Phe Lys Phe Glu Leu Tyr Phe Gly Leu Leu Val Phe Val Gly Tyr Met
            180                 185                 190

Val Val Asp Thr Gln Glu Ile Ile Glu Met Ala His Met Gly Asp Met
        195                 200                 205

Asp Tyr Val Lys His Ala Leu Thr Leu Phe Thr Asp Phe Ile Ala Val
        210                 215                 220

Phe Val Arg Ile Leu Ile Ile Met Leu Lys Asn Ser Ala Glu Lys Asn
225                 230                 235                 240

Glu Arg Glu Arg Lys Lys Lys Arg Arg Asp
                245                 250

<210> SEQ ID NO 28
<211> LENGTH: 753
<212> TYPE: DNA
<213> ORGANISM: Cucumis sativus

<400> SEQUENCE: 28
atggacgcat tctcttcttt cttcgattct caatctggat ccagaacccg ctggagtcat      60
gaatctctca agaacttccg gcagatttcg cccgccgttc aatctcatct tcagcgggtt     120
tatctcactc ttggttgtgc tttggttgca tctgctgctg gagcttatct gcatatactt     180
tggaatattg gtggttttct tacaacactt gcaactatcg gatgtattac atggctaatg     240
gccactcctc cttatgaaga gaaaagaggg cctctatttt acttggggc tgctcttctc      300 gaagggctt ccattggtcc tttgatcagt ctggctattg attttgaccc aagtgttctg      360
gtgagcgctt tcgtgggaac tgcggttgcc ttttgttgtt tctcaggagc agccttgttg      420
gcaagacgta gagaattcct ttatctcggt ggcttacttt cttccggtgt atccatgtta      480
ctctggttac atttcgcctc ctctttattc ggtggttcta ctgcccttt caagtttgag      540 ttgtactttg gctgttggt ttttgttggc tacatggtag ttgatactca ggaataatt       600 gagatggcac atatgggtga tatggattat gtgaaacatg cattaactct cttcactgat     660
ttcattgcgg tgtttgtccg aattctcatt ataatgctaa agaactctgc tgagaagaac     720
gagagggaga ggaagaagaa gaggagggac tga                                  753

<210> SEQ ID NO 29

<211> LENGTH: 249
<212> TYPE: PRT
<213> ORGANISM: Cucumis sativus

<400> SEQUENCE: 29

Met Asp Ala Phe Ser Ser Phe Phe Asp Ser Gln Gln Pro Ser Thr Asn
1               5                   10                  15
Pro Trp Thr Tyr Asp Ser Leu Lys Asn Phe Arg Gln Ile Ser Pro Val
            20                  25                  30
Val Gln Ser His Leu His Gln Val Tyr Leu Thr Leu Gly Cys Ala Leu
        35                  40                  45
Val Ala Ser Ala Ala Gly Ala Tyr Leu His Ile Leu Trp Asn Ile Gly
    50                  55                  60
Gly Ile Leu Thr Ala Leu Ala Gly Ile Gly Cys Ile Thr Trp Leu Met
65                  70                  75                  80
Ala Thr Pro Pro Tyr Glu Glu Arg Lys Arg Leu Ser Met Leu Met Ala
                85                  90                  95
Ala Ala Leu Leu Glu Gly Ala Ser Ile Gly Pro Leu Ile Gly Leu Ala
            100                 105                 110
Ile Glu Ile Asp Pro Ser Val Leu Val Ser Ala Phe Val Gly Thr Ala
        115                 120                 125
Val Ala Phe Gly Cys Phe Ser Ala Ala Ala Met Leu Ala Arg Arg Arg
    130                 135                 140
Glu Phe Leu Tyr Leu Gly Gly Leu Leu Ser Ser Gly Ile Ser Met Leu
145                 150                 155                 160
Leu Trp Leu His Phe Ala Ser Ser Ile Phe Gly Gly Ser Thr Ala Leu
                165                 170                 175
Phe Lys Phe Glu Leu Tyr Phe Gly Leu Leu Leu Phe Val Gly Tyr Met
            180                 185                 190
Val Val Asp Thr Gln Glu Ile Ile Glu Arg Ala His Leu Gly Asp Met
        195                 200                 205
Asp Tyr Val Lys His Ala Leu Thr Leu Phe Thr Asp Phe Val Gly Val
    210                 215                 220
Phe Val Arg Leu Leu Ile Ile Met Val Arg Asn Ser Val Glu Lys Asn
225                 230                 235                 240
Glu Glu Lys Lys Lys Lys Arg Arg Asp
                245

<210> SEQ ID NO 30
<211> LENGTH: 750
<212> TYPE: DNA
<213> ORGANISM: Cucumis sativus

<400> SEQUENCE: 30
atggatgcct tttcatcttt cttcgattct caacaacctt ctacaaaccc ttggacctac    60
gattctctca agaatttccg gcagatttcc ccgtcgttc aatctcatct ccaccaggtt    120
taccttactc tgggttgtgc tttggttgca tctgctgctg gagcttatct ccatattctg    180
tggaacattg gcggaatcct cactgcactt gctggtattg gatgcatcac atggctaatg    240
gccactcctc cttatgaaga gagaaagagg ctttctatgt taatggcggc tgctcttctt    300
gaaggagcat caattggtcc tttgattggg ttggctatcg agattgatcc aagtgttctg    360
gtcagtgcct ttgtgggaac tgctgtggct tttggttgtt tctctgcagc agccatgttg    420
gcaagacgta gagaattcct ttacctgggt ggcttacttt cttctgggat atccatgtta    480
ctctggttgc atttcgcttc atctatattc ggtggttcta ctgctctttt caagtttgag    540

```
ttgtactttg ggctattgct gtttgtgggc tacatggtag ttgatactca agaaataatc      600
gagagggctc atcttggtga tatggactat gtgaagcatg ccctgactct tttcactgat      660
ttcgttggtg ttttcgtccg acttctcatt attatggtaa ggaactcggt agagaagaat      720
gaggagaaaa agaagaagag gagggactaa                                       750
```

<210> SEQ ID NO 31
<211> LENGTH: 247
<212> TYPE: PRT
<213> ORGANISM: Gossypium hirsutum

<400> SEQUENCE: 31

```
Met Gly Thr Phe Ser Ser Phe Phe Asp Ser Gln Ser Arg Ser Gln Trp
1               5                   10                  15

Asn Tyr Asn Thr Leu Lys Asn Phe Arg Gln Ile Ser Pro Ile Val Gln
            20                  25                  30

Thr His Leu Lys Lys Val Tyr Met Thr Leu Cys Cys Met Leu Val Ala
        35                  40                  45

Ser Ala Phe Gly Ala Tyr Leu His Ile Ile Trp Asn Ile Gly Gly Tyr
    50                  55                  60

Leu Thr Thr Phe Ala Cys Phe Gly Ala Ile Ile Trp Leu Arg Ser Thr
65                  70                  75                  80

Pro Pro Cys Gln Glu Gln Lys Arg Val Ser Leu Leu Met Ala Ser Ala
                85                  90                  95

Val Phe Glu Gly Ala Ser Ile Gly Pro Leu Ile Asp Leu Ala Ile Gln
            100                 105                 110

Ile Asp Pro Ser Val Leu Val Ala Ala Phe Val Gly Thr Ala Leu Ala
        115                 120                 125

Phe Ala Cys Phe Ser Arg Ala Ala Met Leu Ala Arg Arg Arg Glu Tyr
    130                 135                 140

Leu Tyr Leu Gly Gly Leu Leu Ser Ser Gly Val Ser Met Leu Leu Trp
145                 150                 155                 160

Leu His Phe Ala Ser Ser Ile Phe Gly Gly Ser Thr Ala Leu Phe Lys
                165                 170                 175

Met Glu Ile Tyr Leu Gly Leu Leu Val Phe Val Gly Tyr Met Val Val
            180                 185                 190

Asp Thr Gln Asp Ile Ile Glu Lys Ala His Leu Gly Asp Leu Asp Tyr
        195                 200                 205

Val Lys His Ala Leu Thr Leu Phe Thr Asp Phe Val Ala Val Phe Val
    210                 215                 220

Arg Ile Leu Ile Ile Met Leu Lys Asn Ser Ala Glu Lys Gly Glu Arg
225                 230                 235                 240

Gln Lys Lys Lys Arg Ser Asp
                245
```

<210> SEQ ID NO 32
<211> LENGTH: 934
<212> TYPE: DNA
<213> ORGANISM: Gossypium hirsutum

<400> SEQUENCE: 32

```
aacgaacgat gggcacgttc tcgtctttct tcgattctca atcgagaagc cagtggaatt      60
acaacactct caagaatttc cgtcagatct ctccgattgt tcaaacgcat ctcaaaaagg     120
tttatatgac cctatgttgt atgcttgttg cctctgcctt tggggcttat cttcatataa     180
```

```
tttggaacat tggggttac ctcacgacat tgcatgctt tggagccata atttggctcc      240
gttctacccc tccttgtcaa gagcaaaaga gggtttctct tctaatggca tcagcagttt      300
ttgaaggagc ttcaattggt cctctaattg acttggccat tcaaattgac ccaagtgttc      360
tggtagctgc attcgtggga acagcattgg cctttgcatg cttttcaaga gctgccatgt      420
tagcaaggcg gagagagtac ctctaccttg gtggcttgct ttcatctggt gtgtccatgc      480
ttctctggtt gcattttgct tcttctatct ttggtggttc tacagccctc tttaagatgg      540
agatctactt agggctcttg gtgtttgttg gctacatggt agtggacaca caagacataa      600
ttgagaaggc acactgggt gatctggatt atgtaaagca tgctttgaca ctttttactg       660
atttcgttgc cgtatttgtt cgcattctga taatcatgtt gaaaaattca gctgagaagg      720
gtgagagaca gaagaagaag aggagtgact aaatcataaa gcaccctatg aataggctt       780 ctcatctaat cctccgtgtt gaactctatt tttaatacaa gttttatttc ttgattccat      840
tgtgaataca tgtgttgata tacgggaagg ttaggtcttt actgttctg tttcttcggt       900 ggttttctg atatggaacc tttaaactaa tgac                                   934

<210> SEQ ID NO 33
<211> LENGTH: 1127
<212> TYPE: DNA
<213> ORGANISM: Lactuca sativa

<400> SEQUENCE: 33
caacgcctta caggcagacg actttcgcat atcggtatag caaacataac attgtctacg       60
ttcagataaa tatcctttgc tcatttcagt tccaaaaact cgaagaagaa gaagaagaga      120
acaatggaag gtttcacatc gttcttcgac tcgcaatctg cctctcgcaa ccgctggagt      180
tatgattctc tcaaaaactt ccgccagatc tcacctctcg ttcaaactca tctcaagcag      240 gtgtaccta cgctatgctg tgctttagtg gcatcggctg ctggggctta ccttcacatt       300
ctatggaata tcggtggcct cctcacaaca atggcttgca tggaagcat ggtgtggctt        360 ctctcagctc ctccttatca agagcaaaaa agggtggctc ttctgatggc agctgcactt      420
tttgaaggcg cctctattgg tcctctgatt gagctgggca ttaacttcga tccaagcatt      480
gtgtttggcg cttttgtagg ttgtgctgtg ttttttggtt gcttctcagc tgctgccatg      540
ttggcaaggc gcagggagta cttgtacctc ggggccttc tttcatctgg cgtctccctt        600
ctcttctggt tgcactttgc atcctccatt tttggtggtt ccatggctgt tttcaagttt      660
gagttgtatt ttggactctt ggtgtttgtg ggctacatcg tctttgacac ccaagaaatt      720
attgagaagg ctcacttggg tgatatggat tacgttaagc atgcattgac ccttttcaca      780
gattttgtcg ctgttttgtg gcggattctg atcatcatgt taagaatgc atctgagaag       840 gaagagaaga agaagaagag gagaaactag atttgcttct caacttgtgg tttccataac      900
tccttgtgtt cacctgaaac aagcatgtta atagtttgat acttgcttca ctttagcata      960
ggctgtgatg taatgtcgtg tgacatgcca ttatggctgt gtgattgagc atctagcctt     1020
tttatcttct aaagcttttt tcttaacatt gataaggaaa gttccttgtg ataacattta     1080
agaccatttt aatttctcct ttctcattca aaaaaaaaaa aaaaaaa                   1127

<210> SEQ ID NO 34
<211> LENGTH: 200
<212> TYPE: DNA
<213> ORGANISM: Lactuca sativa

<400> SEQUENCE: 34
```

```
ccaccgatgt tccataggat gtgaaggtaa gccccaactg cagatgccat gagagcacaa    60
catagtgaga ggtaaacctg tttgagatga gtctgaacta agggagagat ttgacggaaa   120
ttcttgagag aatcgtaggt ccagctgttt ggagaagccg atcgcgattg tgaatcgaag   180
aacgatgaga atgattccat                                              200
```

<210> SEQ ID NO 35
<211> LENGTH: 200
<212> TYPE: DNA
<213> ORGANISM: Lactuca sativa

<400> SEQUENCE: 35

```
ttgggctgtt ggtgtttgtt gggtacatgg tggttgacac ccaagatatc attgaaaagg    60
ctcatcttgg agatttggat tatgtgaaac atgctcttac gcttttcact gatttcattg   120 ctgttttgt tcgcattctt atcatcatgt tgaagaattc ggctgaaaga aagagaaga   180 agaagaagag gagggattag                                              200
```

<210> SEQ ID NO 36
<211> LENGTH: 200
<212> TYPE: DNA
<213> ORGANISM: Lactuca sativa

<400> SEQUENCE: 36

```
ctaatccctc ctcttcttct tcttctcttc tctttcagcc gaattcttca acatgatgat    60
aagaatgcga acaaaaacag caatgaaatc agtgaaaagc gtaagagcat gtttcacata   120
atccaaatct ccaagatgag cctttttcaat gatatcttgg gtgtcaacca ccatgtaccc   180
aacaaacacc aacagcccaa                                              200
```

<210> SEQ ID NO 37
<211> LENGTH: 200
<212> TYPE: DNA
<213> ORGANISM: Solanum lycopersicum

<400> SEQUENCE: 37

```
atggaaggtt tcacatcgtt cttcgactcg caatctgcct ctcgcaaccg ctggagttat    60
gattctctca aaaacttccg ccagatctca cctctcgttc aaactcatct caagcaggtg   120
taccttacgc tatgctgtgc tttagtggca tcggctgctg gggcttacct tcacattcta   180
tggaatatcg gtggcctcct                                              200
```

<210> SEQ ID NO 38
<211> LENGTH: 200
<212> TYPE: DNA
<213> ORGANISM: Solanum lycopersicum

<400> SEQUENCE: 38

```
aggaggccac cgatattcca tagaatgtga aggtaagccc cagcagccga tgccactaaa    60
gcacagcata gcgtaaggta cacctgcttg agatgagttt gaacgagagg tgagatctgg   120
cggaagtttt tgagagaatc ataactccag cggttgcgag aggcagattg cgagtcgaag   180
aacgatgtga aaccttccat                                              200
```

<210> SEQ ID NO 39
<211> LENGTH: 200
<212> TYPE: DNA
<213> ORGANISM: Solanum lycopersicum

<400> SEQUENCE: 39
ttggactctt ggtgtttgtg ggctacatcg tctttgacac ccaagaaatt attgagaagg    60
ctcacttggg tgatatggat tacgttaagc atgcattgac ccttttcaca gattttgtcg   120
ctgtttttgt gcggattctg atcatcatgt taaagaatgc atctgagaag gaagagaaga   180
agaagaagag gagaaactag                                               200

<210> SEQ ID NO 40
<211> LENGTH: 200
<212> TYPE: DNA
<213> ORGANISM: Solanum lycopersicum

<400> SEQUENCE: 40
ctagtttctc ctcttcttct tcttctcttc cttctcagat gcattcttta acatgatgat    60
cagaatccgc acaaaaacag cgacaaaatc tgtgaaaagg gtcaatgcat gcttaacgta   120
atccatatca cccaagtgag ccttctcaat aatttcttgg gtgtcaaaga cgatgtagcc   180
cacaaacacc aagagtccaa                                               200

<210> SEQ ID NO 41
<211> LENGTH: 200
<212> TYPE: DNA
<213> ORGANISM: Vitis vinifera

<400> SEQUENCE: 41
atggaggcgt tctctgcgtt tttcgattca caatcgagct caaggagcgg ttggacctac    60
gattcactca agaatttccg ccagatttct cctgccgttc aaactcatct caagcaggtt   120
tatctctccc tgtgctgtgc cttgattgca tctgctgcag gagcttacct gcatcttctc   180
tggaatattg gtggccttct                                               200

<210> SEQ ID NO 42
<211> LENGTH: 200
<212> TYPE: DNA
<213> ORGANISM: Vitis vinifera

<400> SEQUENCE: 42
agaaggccac caatattcca gagaagatgc aggtaagctc ctgcagcaga tgcaatcaag    60
gcacagcaca gggagagata aacctgcttg agatgagttt gaacggcagg agaaatctgg   120
cggaaattct tgagtgaatc gtaggtccaa ccgctccttg agctcgattg tgaatcgaaa   180
aacgcagaga acgcctccat                                               200

<210> SEQ ID NO 43
<211> LENGTH: 200
<212> TYPE: DNA
<213> ORGANISM: Vitis vinifera

<400> SEQUENCE: 43
ttggactgtt ggtgtttgtg ggctacatgg tagtagacac ccaggacata atagagaaag    60
cccatctcgg ggatcgggac tatgtgaaac attctctcct cctttttcact gattttgctg   120 cagtttttgt tcgaatcctg attatcatgt tgaagaactc ggctgaaaag agtgagaaga   180
agaagaaaag gagaaattga                                               200

<210> SEQ ID NO 44
<211> LENGTH: 200
<212> TYPE: DNA
<213> ORGANISM: Vitis vinifera

<400> SEQUENCE: 44

```
tcaatttctc cttttcttct tcttctcact cttttcagcc gagttcttca acatgataat    60
caggattcga acaaaaactg cagcaaaatc agtgaaaagg aggagagaat gtttcacata   120
gtcccgatcc ccgagatggg cttctctat tatgtcctgg gtgtctacta ccatgtagcc    180
cacaaacacc aacagtccaa                                                200
```

<210> SEQ ID NO 45
<211> LENGTH: 200
<212> TYPE: DNA
<213> ORGANISM: Capsicum annuum

<400> SEQUENCE: 45

```
atggagggtt tcacgtcgtt cttcgaatcg caatcggctt ctcgcagtcg ctggaattat    60
gatgctctca aaaacttcca tcagatctct cctcgtgttc aaactcatct caaacaggtc   120
tacctcacac tatgctgtgc tttagtcgca tcagctgctg gggcttacct tcacattctt   180
tggaacatcg gtggcttcct                                                200
```

<210> SEQ ID NO 46
<211> LENGTH: 200
<212> TYPE: DNA
<213> ORGANISM: Capsicum annuum

<400> SEQUENCE: 46

```
aggaagccac cgatgttcca agaatgtga aggtaagccc cagcagctga tgcgactaaa     60
gcacagcata gtgtgaggta gacctgtttg agatgagttt gaacacgagg agagatctga   120
tggaagtttt tgagagcatc ataattccag cgactgcgag aagccgattg cgattcgaag   180
aacgacgtga aaccctccat                                                200
```

<210> SEQ ID NO 47
<211> LENGTH: 200
<212> TYPE: DNA
<213> ORGANISM: Capsicum annuum

<400> SEQUENCE: 47

```
ttggtttctt ggtgtttgtg ggctacatag tttttgacac ccaagaaatc attgagaagg    60
ctcacttggg tgatatggat tacgtcaagc atgcactcac cctcttcaca gatttttgttg   120 cagtctttgt gcggatttg atcatcatgt tgaagaatgc atttgagaag gaagagaaga   180
agaagaagag gagaaactag                                                200
```

<210> SEQ ID NO 48
<211> LENGTH: 200
<212> TYPE: DNA
<213> ORGANISM: Capsicum annuum

<400> SEQUENCE: 48

```
ctagtttctc ctcttcttct tcttctcttc cttctcaaat gcattcttca acatgatgat    60
caaaatccgc acaaagactg caacaaaatc tgtgaagagg gtgagtgcat gcttgacgta   120
atccatatca cccaagtgag ccttctcaat gatttcttgg gtgtcaaaaa ctatgtagcc   180
cacaaacacc aagaaaccaa                                                200
```

<210> SEQ ID NO 49
<211> LENGTH: 200
<212> TYPE: DNA

<213> ORGANISM: Glycine max

<400> SEQUENCE: 49

```
atggactcct tcaattcctt cttcgattca acaaaccgat ggaattacga tactctcaaa    60
aacttccgtc aaatttctcc ggtcgttcag aatcacctca agcaggttta ttttactctg   120
tgtttcgccg tggttgctgc ggctgttggg gcttaccttc atgtcctctt gaacattggg   180
ggttttctta ctacagtggc                                               200
```

<210> SEQ ID NO 50
<211> LENGTH: 200
<212> TYPE: DNA
<213> ORGANISM: Glycine max

<400> SEQUENCE: 50

```
gccactgtag taagaaaacc cccaatgttc aagaggacat gaaggtaagc cccaacagcc    60
gcagcaacca cggcgaaaca cagagtaaaa taaacctgct tgaggtgatt ctgaacgacc   120
ggagaaattt gacggaagtt tttgagagta tcgtaattcc atcggtttgt tgaatcgaag   180
aaggaattga aggagtccat                                               200
```

<210> SEQ ID NO 51
<211> LENGTH: 200
<212> TYPE: DNA
<213> ORGANISM: Glycine max

<400> SEQUENCE: 51

```
ttgggctttt ggtgtttgta ggttacattg tagtagacac ccaagaaata gttgagaggg    60
cacacttggg cgatctggac tatgtaaagc atgccttgac cttgtttacc gatttggttg   120
cagttttgt ccggattctt gttattatgt tgaagaattc ggctgagagg aatgagaaga   180
aaagaagag gagagattga                                                200
```

<210> SEQ ID NO 52
<211> LENGTH: 200
<212> TYPE: DNA
<213> ORGANISM: Glycine max

<400> SEQUENCE: 52

```
tcaatctctc ctcttctttt tcttctcatt cctctcagcc gaattcttca acataataac    60
aagaatccgg acaaaaactg caaccaaatc ggtaaacaag gtcaaggcat gctttacata   120
gtccagatcg cccaagtgtg ccctctcaac tatttcttgg gtgtctacta caatgtaacc   180
tacaaacacc aaaagcccaa                                               200
```

<210> SEQ ID NO 53
<211> LENGTH: 200
<212> TYPE: DNA
<213> ORGANISM: Sorghum bicolor

<400> SEQUENCE: 53

```
atggacgcgt tctactcgac ctcctcgtcg tcgtcgtcct cggggccgta cggcgcggcg    60
gcgtacggcg gcagcggctg gggctacgac tcgctcaaga acttccgcca gatcagcccc   120
gccgtccaga cccacctcaa gctcgtttac ctgaccctct gcgtggcgct ggcctcgtcg   180
gcgctgggcg cttacctgca                                               200
```

<210> SEQ ID NO 54
<211> LENGTH: 200

```
<212> TYPE: DNA
<213> ORGANISM: Sorghum bicolor

<400> SEQUENCE: 54
tgcaggtaag cgcccagcgc cgacgaggcc agcgccacgc agagggtcag gtaaacgagc    60
ttgaggtggg tctggacggc ggggctgatc tggcggaagt tcttgagcga gtcgtagccc   120
cagccgctgc cgccgtacgc cgccgcgccg tacgccccg aggacgacga cgacgaggag    180
gtcgagtaga acgcgtccat                                                200

<210> SEQ ID NO 55
<211> LENGTH: 200
<212> TYPE: DNA
<213> ORGANISM: Sorghum bicolor

<400> SEQUENCE: 55
ggctgcttat cttcctggga tacatggtgt acgacacgca ggagatcatc gagagggcgc    60
accacggcga catggactac atcaagcacg ccctcaccct cttcaccgac ttcgtggctg   120
tccttgtccg catcctcgtc atcatgctca agaacgcggc tgacaagtcg gaggacaaga   180
agaggaagaa gaggtcgtga                                                200

<210> SEQ ID NO 56
<211> LENGTH: 200
<212> TYPE: DNA
<213> ORGANISM: Sorghum bicolor

<400> SEQUENCE: 56
tcacgacctc ttcttcctct tcttgtcctc cgacttgtca gccgcgttct tgagcatgat    60
gacgaggatg cggacaagga cagccacgaa gtcggtgaag agggtgaggg cgtgcttgat   120
gtagtccatg tcgccgtggt gcgccctctc gatgatctcc tgcgtgtcgt acaccatgta   180
tcccaggaag ataagcagcc                                                200

<210> SEQ ID NO 57
<211> LENGTH: 200
<212> TYPE: DNA
<213> ORGANISM: Zea mays

<400> SEQUENCE: 57
atggacgcgt tcttctcggc ctcctccgcg tcggcgccct acggctacgg cgccggcgga    60
tggagctacg actcgctcaa gaacttccgc cagatcaccc ccgccgtcca gacccacctc   120
aagctcgtct acctcaccct gtgcgcgcg ctggcctcgt cggcggtggg cgcttacctg    180
cacgtggtct ggaacatcgg                                                200

<210> SEQ ID NO 58
<211> LENGTH: 200
<212> TYPE: DNA
<213> ORGANISM: Zea mays

<400> SEQUENCE: 58
ccgatgttcc agaccacgtg caggtaagcg cccaccgccg acgaggccag cgccgcgcac    60
agggtgaggt agacgagctt gaggtgggtc tggacgcgg gggtgatctg gcggaagttc   120
ttgagcgagt cgtagctcca tccgccggcg ccgtagccgt agggcgccga cgcggaggag   180
gccgagaaga acgcgtccat                                                200

<210> SEQ ID NO 59
```

```
<211> LENGTH: 200
<212> TYPE: DNA
<213> ORGANISM: Zea mays

<400> SEQUENCE: 59
ggctgctcat cttcctgggc tacgtggtgt acgacacgca ggagatcatc gagagggcgc      60
accgcggcga catggaccac gtcaagcacg ccctcaccct cttcacagac ttcgtggccg     120
tcctcgtccg cgtcctcgtc atcatgctca agaacggggc cgacaagtcg gaggacaaga     180
agaggaagaa gaggtcgtga                                                 200

<210> SEQ ID NO 60
<211> LENGTH: 200
<212> TYPE: DNA
<213> ORGANISM: Zea mays

<400> SEQUENCE: 60
tcacgacctc ttcttcctct tcttgtcctc cgacttgtcg gccccgttct tgagcatgat      60
gacgaggacg cggacgagga cggccacgaa gtctgtgaag agggtgaggg cgtgcttgac     120
gtggtccatg tcgccgcggt gcgccctctc gatgatctcc tgcgtgtcgt acaccacgta     180
gcccaggaag atgagcagcc                                                 200

<210> SEQ ID NO 61
<211> LENGTH: 200
<212> TYPE: DNA
<213> ORGANISM: Triticum aestivum

<400> SEQUENCE: 61
atggacgcct tctactcgac ctcgtcggcg gcggccagcg gatggggcta cgactccctc      60
aagaacttcc gcgagatctc ccccgccgtg cagtcccacc tcaagctcgt ttacctgacc     120
ctatgctttg ccctggcctc atctgccgtg ggtgcttacc tgcacattgc cctgaacatt     180
ggcgggatgc tgacaatgct                                                 200

<210> SEQ ID NO 62
<211> LENGTH: 200
<212> TYPE: DNA
<213> ORGANISM: Triticum aestivum

<400> SEQUENCE: 62
agcattgtca gcatcccgcc aatgttcagg gcaatgtgca ggtaagcacc cacggcagat      60
gaggccaggg caaagcatag ggtcaggtaa acgagcttga ggtgggactg cacggcgggg     120
gagatctcgc ggaagttctt gagggagtcg tagccccatc cgctggccgc cgccgacgag     180
gtcgagtaga aggcgtccat                                                 200

<210> SEQ ID NO 63
<211> LENGTH: 200
<212> TYPE: DNA
<213> ORGANISM: Triticum aestivum

<400> SEQUENCE: 63
tgttgatctt cctggggtac atggtgtacg acacgcagga gatcatcgag agggcgcacc      60
acggtgacat ggactacatc aagcacgcgc tcaccctctt caccgacttc gtcgccgtcc     120
tcgtccgcat cctcatcatc atgctcaaga acgcaggcga caagtcggag gacaagaaga     180
agaggaagag gaggtcctga                                                 200
```

```
<210> SEQ ID NO 64
<211> LENGTH: 200
<212> TYPE: DNA
<213> ORGANISM: TRiticum aestivum

<400> SEQUENCE: 64
tcaggacctc ctcttcctct tcttcttgtc ctccgacttg tcgcctgcgt tcttgagcat      60
gatgatgagg atgcggacga ggacggcgac gaagtcggtg aagagggtga gcgcgtgctt     120
gatgtagtcc atgtcaccgt ggtgcgccct ctcgatgatc tcctgcgtgt cgtacaccat     180 gtacccagg aagatcaaca                                                  200

<210> SEQ ID NO 65
<211> LENGTH: 200
<212> TYPE: DNA
<213> ORGANISM: Triticum aestivum

<400> SEQUENCE: 65
atggacgcct tctactcgac ctcgtcggcg gcggcgagcg gctggggcta cgactccctc      60
aagaacttcc gcgagatctc ccccgccgtg cagtcccacc tcaagctcgt ttacctgacc     120
ctatgctttg ccctggcctc atctgccgtg ggtgcttacc tgcacattgc cctgaacatc     180
ggtgggatgc tgacaatgct                                                 200

<210> SEQ ID NO 66
<211> LENGTH: 200
<212> TYPE: DNA
<213> ORGANISM: Triticum aestivum

<400> SEQUENCE: 66
agcattgtca gcatcccacc gatgttcagg gcaatgtgca ggtaagcacc cacggcagat      60
gaggccaggg caaagcatag ggtcaggtaa acgagcttga ggtgggactg cacggcgggg     120
gagatctcgc ggaagttctt gagggagtcg tagccccagc cgctcgccgc cgccgacgag     180
gtcgagtaga aggcgtccat                                                 200

<210> SEQ ID NO 67
<211> LENGTH: 200
<212> TYPE: DNA
<213> ORGANISM: Triticum aestivum

<400> SEQUENCE: 67
tgttgatctt tctgggatac atggtgtacg acacgcagga gatcatcgag agggcgcacc      60
acggcgacat ggactacatc aagcacgcgc tcaccctctt caccgacttt gtcgccgtcc     120
tcgtccggat cctcatcatc atgctcaaga acgcaggcga caagtcggag gacaagaaga     180
agaggaagag gaggtcctga                                                 200

<210> SEQ ID NO 68
<211> LENGTH: 200
<212> TYPE: DNA
<213> ORGANISM: Triticum aestivum

<400> SEQUENCE: 68
tcaggacctc ctcttcctct tcttcttgtc ctccgacttg tcgcctgcgt tcttgagcat      60
gatgatgagg atccggacga ggacggcgac aaagtcggtg aagagggtga gcgcgtgctt     120
gatgtagtcc atgtcgccgt ggtgcgccct ctcgatgatc tcctgcgtgt cgtacaccat     180
gtatcccaga aagatcaaca                                                 200
```

<210> SEQ ID NO 69
<211> LENGTH: 200
<212> TYPE: DNA
<213> ORGANISM: Glycine max

<400> SEQUENCE: 69

| atggacactt tcttcaagtc cccatcgtct tcttcttcta gaagcagctg gagttacgat | 60 |
| actctcaaga atttccgcga gatctctccg ctcgttcaga atcacatcaa actggtttat | 120 |
| tttacgttat gttgcgctgt ggtggctgct gctgttggag ccttccttca tgttctgtgg | 180 |
| aacattggcg gttttctcac | 200 |

<210> SEQ ID NO 70
<211> LENGTH: 200
<212> TYPE: DNA
<213> ORGANISM: Glycine max

<400> SEQUENCE: 70

| gtgagaaaac cgccaatgtt ccacagaaca tgaaggaagg ctccaacagc agcagccacc | 60 |
| acagcgcaac ataacgtaaa ataaaccagt ttgatgtgat tctgaacgag cggagagatc | 120 |
| tcgcggaaat tcttgagagt atcgtaactc cagctgcttc tagaagaaga agacgatggg | 180 |
| gacttgaaga aagtgtccat | 200 |

<210> SEQ ID NO 71
<211> LENGTH: 200
<212> TYPE: DNA
<213> ORGANISM: Glycine max

<400> SEQUENCE: 71

| actttgggct tttggtgttt gtgggctacg ttatagtaga cactcaagta atcattgaga | 60 |
| gggctcactt tggtgacctg gattatgtta agcatgcatt gacactgttc actgatttgg | 120 |
| ctgcaatctt tgtgcgaatt cttaatataa tgttgaataa ttcatctaag agaaatgaga | 180 |
| agaagaggag gagagattaa | 200 |

<210> SEQ ID NO 72
<211> LENGTH: 200
<212> TYPE: DNA
<213> ORGANISM: Glycine max

<400> SEQUENCE: 72

| ttaatctctc ctcctcttct tctcatttct cttagatgaa ttattcaaca ttatattaag | 60 |
| aattcgcaca aagattgcag ccaaatcagt gaacagtgtc aatgcatgct taacataatc | 120 |
| caggtcacca aagtgagccc tctcaatgat tacttgagtg tctactataa cgtagcccac | 180 |
| aaacaccaaa agcccaaagt | 200 |

<210> SEQ ID NO 73
<211> LENGTH: 200
<212> TYPE: DNA
<213> ORGANISM: Hordeum vulgare

<400> SEQUENCE: 73

| atggacgcct tctactcgac ctcgtcggcg gcggcgagcg gctggggcca cgactccctc | 60 |
| aagaacttcc gccagatctc ccccgccgtg cagtcccacc tcaagctcgt ttacctgact | 120 |
| ctatgctttg cactgcctc atctgccgtg ggtgcttacc tacacattgc cctgaacatc | 180 |
| ggcgggatgc tgacaatgct | 200 |

<210> SEQ ID NO 74
<211> LENGTH: 200
<212> TYPE: DNA
<213> ORGANISM: Hordeum vulgare

<400> SEQUENCE: 74

```
agcattgtca gcatcccgcc gatgttcagg gcaatgtgta ggtaagcacc cacggcagat      60
gaggccagtg caaagcatag agtcaggtaa acgagcttga ggtgggactg cacggcgggg     120
gagatctggc ggaagttctt gagggagtcg tggccccagc cgctcgccgc cgccgacgag     180
gtcgagtaga aggcgtccat                                                 200
```

<210> SEQ ID NO 75
<211> LENGTH: 200
<212> TYPE: DNA
<213> ORGANISM: Hordeum vulgare

<400> SEQUENCE: 75

```
tgttgatctt cctggggtac atggtgtacg acacgcagga gatcatcgag agggcgcacc      60
atggcgacat ggactacatc aagcacgccc tcaccctctt caccgacttt gttgccgtcc     120
tcgtccgagt cctcatcatc atgctcaaga acgcaggcga caagtcggag acaagaaga     180
agaggaagag gaggtcctga                                                 200
```

<210> SEQ ID NO 76
<211> LENGTH: 200
<212> TYPE: DNA
<213> ORGANISM: Hordeum vulgare

<400> SEQUENCE: 76

```
tcaggacctc ctcttcctct tcttcttgtc ctccgacttg tcgcctgcgt tcttgagcat      60
gatgatgagg actcggacga ggacggcaac aaagtcggtg aagagggtga gggcgtgctt     120
gatgtagtcc atgtcgccat ggtgcgccct ctcgatgatc tcctgcgtgt cgtacaccat     180
gtaccccagg aagatcaaca                                                 200
```

<210> SEQ ID NO 77
<211> LENGTH: 200
<212> TYPE: DNA
<213> ORGANISM: Oryza sativa

<400> SEQUENCE: 77

```
atggacgcct tctactcgac ctcgtcggcg tacggagcgg cggcgagcgg ctggggctac      60
gactcgctga agaacttccg ccagatctcc ccgccgtcc agtcccacct caagctcgtt     120
tacctgacac tatgcgtcgc cctggctgcg tcggcggtgg gcgcatacct gcacgtcgcc     180
ttgaacatcg gcgggatgtt                                                 200
```

<210> SEQ ID NO 78
<211> LENGTH: 200
<212> TYPE: DNA
<213> ORGANISM: Oryza sativa

<400> SEQUENCE: 78

```
aacatcccgc cgatgttcaa ggcgacgtgc aggtatgcgc ccaccgccga cgcagccagg      60
gcgacgcata gtgtcaggta acgagcttg aggtgggact ggacggcggg ggagatctgg     120
cggaagttct tcagcgagtc gtagccccag ccgctcgccg ccgctccgta cgccgacgag     180
```
gtcgagtaga aggcgtccat                                                  200

<210> SEQ ID NO 79
<211> LENGTH: 200
<212> TYPE: DNA
<213> ORGANISM: Oryza sativa

<400> SEQUENCE: 79
gcctgttgat cttcctgggg tacatggtgt atgacacgca ggagatcatc gagagggctc      60
accacggtga catggactac atcaagcacg cactcaccct cttcactgac ttcgtggccg     120
tccttgtccg gatcctcgtc atcatgctca agaacgcgtc tgacaagtcg gaggagaaga     180
agaggaagaa gaggtcttga                                                 200

<210> SEQ ID NO 80
<211> LENGTH: 200
<212> TYPE: DNA
<213> ORGANISM: Oryza sativa

<400> SEQUENCE: 80
tcaagacctc ttcttcctct tcttctcctc cgacttgtca gacgcgttct tgagcatgat      60
gacgaggatc cggacaagga cggccacgaa gtcagtgaag agggtgagtg cgtgcttgat     120
gtagtccatg tcaccgtggt gagccctctc gatgatctcc tgcgtgtcat acaccatgta     180
ccccaggaag atcaacaggc                                                 200

<210> SEQ ID NO 81
<211> LENGTH: 200
<212> TYPE: DNA
<213> ORGANISM: Cucumis sativus

<400> SEQUENCE: 81
atggacgcat tctcttcttt cttcgattct caatctggat ccagaacccg ctggagtcat      60
gaatctctca agaacttccg gcagatttcg cccgccgttc aatctcatct tcagcgggtt     120
tatctcactc ttggttgtgc tttggttgca tctgctgctg gagcttatct gcatatactt     180
tggaatattg gtggttttct                                                 200

<210> SEQ ID NO 82
<211> LENGTH: 200
<212> TYPE: DNA
<213> ORGANISM: Cucumis sativus

<400> SEQUENCE: 82
agaaaaccac caatattcca agtatatgc agataagctc cagcagcaga tgcaaccaaa       60
gcacaaccaa gagtgagata aacccgctga agatgagatt gaacggcggg cgaaatctgc     120
cggaagttct tgagagattc atgactccag cgggttctgg atccagattg agaatcgaag     180
aaagaagaga atgcgtccat                                                 200

<210> SEQ ID NO 83
<211> LENGTH: 200
<212> TYPE: DNA
<213> ORGANISM: Cucumis sativus

<400> SEQUENCE: 83
tgttggtttt tgttggctac atggtagttg atactcagga aataattgag atggcacata      60
tgggtgatat ggattatgtg aaacatgcat taactctctt cactgatttc attgcggtgt     120
ttgtccgaat tctcattata atgctaaaga actctgctga gaagaacgag agggagagga     180
agaagaagag gagggactga                                                      200

<210> SEQ ID NO 84
<211> LENGTH: 200
<212> TYPE: DNA
<213> ORGANISM: Cucumis sativus

<400> SEQUENCE: 84
tcagtccctc ctcttcttct tcctctccct ctcgttcttc tcagcagagt tctttagcat     60
tataatgaga attcggacaa acaccgcaat gaaatcagtg aagagagtta atgcatgttt    120
cacataatcc atatcaccca tatgtgccat ctcaattatt tcctgagtat caactaccat    180
gtagccaaca aaaaccaaca                                                 200

<210> SEQ ID NO 85
<211> LENGTH: 200
<212> TYPE: DNA
<213> ORGANISM: Cucumis sativus

<400> SEQUENCE: 85
atggatgcct tttcatcttt cttcgattct caacaacctt ctacaaaccc ttggacctac     60
gattctctca agaatttccg gcagatttcc cccgtcgttc aatctcatct ccaccaggtt    120
taccttactc tgggttgtgc tttggttgca tctgctgctg gagcttatct ccatattctg    180
tggaacattg gcggaatcct                                                 200

<210> SEQ ID NO 86
<211> LENGTH: 200
<212> TYPE: DNA
<213> ORGANISM: Cucumis sativus

<400> SEQUENCE: 86
aggattccgc caatgttcca cagaatatgg agataagctc cagcagcaga tgcaaccaaa     60
gcacaaccca gagtaaggta aacctggtgg agatgagatt gaacgacggg ggaaatctgc    120
cggaaattct tgagagaatc gtaggtccaa gggtttgtag aaggttgttg agaatcgaag    180
aaagatgaaa aggcatccat                                                 200

<210> SEQ ID NO 87
<211> LENGTH: 200
<212> TYPE: DNA
<213> ORGANISM: Cucumis sativus

<400> SEQUENCE: 87
ggctattgct gtttgtgggc tacatggtag ttgatactca agaaataatc gagagggctc     60
atcttggtga tatggactat gtgaagcatg ccctgactct tttcactgat ttcgttggtg    120
ttttcgtccg acttctcatt attatggtaa ggaactcggt agagaagaat gaggagaaaa    180
agaagaagag gagggactaa                                                 200

<210> SEQ ID NO 88
<211> LENGTH: 200
<212> TYPE: DNA
<213> ORGANISM: Cucumis sativus

<400> SEQUENCE: 88
ttagtccctc ctcttcttct ttttctcctc attcttctct accgagttcc ttaccataat     60
aatgagaagt cggacgaaaa caccaacgaa atcagtgaaa agagtcaggg catgcttcac    120

```
atagtccata tcaccaagat gagccctctc gattatttct tgagtatcaa ctaccatgta    180
gcccacaaac agcaatagcc                                                200

<210> SEQ ID NO 89
<211> LENGTH: 200
<212> TYPE: DNA
<213> ORGANISM: Gossypium hirsutum

<400> SEQUENCE: 89
atgggcacgt tctcgtctttt cttcgattct caatcgagaa gccagtggaa ttacaacact    60
ctcaagaatt tccgtcagat ctctccgatt gttcaaacgc atctcaaaaa ggtttatatg    120
accctatgtt gtatgcttgt tgcctctgcc tttggggctt atcttcatat aatttggaac    180 attggggtt acctcacgac                                                 200

<210> SEQ ID NO 90
<211> LENGTH: 200
<212> TYPE: DNA
<213> ORGANISM: Gossypium hirsutum

<400> SEQUENCE: 90
gtcgtgaggt aacccccaat gttccaaatt atatgaagat aagccccaaa ggcagaggca    60
acaagcatac aacatagggt catataaacc ttttgagat gcgtttgaac aatcggagag     120
atctgacgga aattcttgag agtgttgtaa ttccactggc ttctcgattg agaatcgaag    180
aaagacgaga acgtgcccat                                                200

<210> SEQ ID NO 91
<211> LENGTH: 200
<212> TYPE: DNA
<213> ORGANISM: Gossypium hirsutum

<400> SEQUENCE: 91
ggctcttggt gtttgttggc tacatggtag tggacacaca agacataatt gagaaggcac    60
acttgggtga tctggattat gtaaagcatg ctttgacact ttttactgat ttcgttgccg    120
tatttgttcg cattctgata atcatgttga aaaattcagc tgagaagggt gagagacaga    180
agaagaagag gagtgactaa                                                200

<210> SEQ ID NO 92
<211> LENGTH: 200
<212> TYPE: DNA
<213> ORGANISM: Gossypium hirsutum

<400> SEQUENCE: 92
ttagtcactc ctcttcttct tctgtctctc acccttctca gctgaatttt tcaacatgat    60
tatcagaatg cgaacaaata cggcaacgaa atcagtaaaa agtgtcaaag catgctttac    120
ataatccaga tcacccaagt gtgccttctc aattatgtct tgtgtgtcca ctaccatgta    180
gccaacaaac accaagagcc                                                200

<210> SEQ ID NO 93
<211> LENGTH: 25
<212> TYPE: DNA
<213> ORGANISM: Hordeum vulgare

<400> SEQUENCE: 93
tcagggcaat gtgtaggtaa gcacc                                          25
```

```
<210> SEQ ID NO 94
<211> LENGTH: 25
<212> TYPE: DNA
<213> ORGANISM: Hordeum vulgare

<400> SEQUENCE: 94
agcattgtca gcatcccgcc gatgt                                           25

<210> SEQ ID NO 95
<211> LENGTH: 25
<212> TYPE: DNA
<213> ORGANISM: Hordeum vulgare

<400> SEQUENCE: 95
caatcagagg tccaaccgaa gcccc                                           25

<210> SEQ ID NO 96
<211> LENGTH: 25
<212> TYPE: DNA
<213> ORGANISM: Hordeum vulgare

<400> SEQUENCE: 96
caatcagagg tccaaccgaa gcccc                                           25

<210> SEQ ID NO 97
<211> LENGTH: 25
<212> TYPE: DNA
<213> ORGANISM: Hordeum vulgare

<400> SEQUENCE: 97
cttgggtcaa agtctatggc aagct                                           25

<210> SEQ ID NO 98
<211> LENGTH: 25
<212> TYPE: DNA
<213> ORGANISM: Hordeum vulgare

<400> SEQUENCE: 98
tccgacaaac cctgtcacga ggatg                                           25

<210> SEQ ID NO 99
<211> LENGTH: 25
<212> TYPE: DNA
<213> ORGANISM: Hordeum vulgare

<400> SEQUENCE: 99
agaagcaccc aaaggcgatg gcggt                                           25

<210> SEQ ID NO 100
<211> LENGTH: 25
<212> TYPE: DNA
<213> ORGANISM: Hordeum vulgare

<400> SEQUENCE: 100
cgcttggcga tgatggcggc gccag                                           25

<210> SEQ ID NO 101
<211> LENGTH: 25
<212> TYPE: DNA
<213> ORGANISM: Hordeum vulgare

<400> SEQUENCE: 101
gccaccgagg tacaggtact ccctg                                           25
```

```
<210> SEQ ID NO 102
<211> LENGTH: 25
<212> TYPE: DNA
<213> ORGANISM: Hordeum vulgare

<400> SEQUENCE: 102
ggatcgacag gccagacgag agcag                                 25

<210> SEQ ID NO 103
<211> LENGTH: 25
<212> TYPE: DNA
<213> ORGANISM: Hordeum vulgare

<400> SEQUENCE: 103
gacgtgacaa actgcagcca gagca                                 25

<210> SEQ ID NO 104
<211> LENGTH: 25
<212> TYPE: DNA
<213> ORGANISM: Hordeum vulgare

<400> SEQUENCE: 104
gctgccagag gagtggccaa agatg                                 25

<210> SEQ ID NO 105
<211> LENGTH: 25
<212> TYPE: DNA
<213> ORGANISM: Hordeum vulgare

<400> SEQUENCE: 105
ggccaaagta aacctcaaac atgaa                                 25

<210> SEQ ID NO 106
<211> LENGTH: 25
<212> TYPE: DNA
<213> ORGANISM: Hordeum vulgare

<400> SEQUENCE: 106
accatgtacc ccaggaagat caaca                                 25

<210> SEQ ID NO 107
<211> LENGTH: 25
<212> TYPE: DNA
<213> ORGANISM: Hordeum vulgare

<400> SEQUENCE: 107
ctcgatgatc tcctgcgtgt cgtac                                 25

<210> SEQ ID NO 108
<211> LENGTH: 24
<212> TYPE: DNA
<213> ORGANISM: Hordeum vulgare

<400> SEQUENCE: 108
ccacctgggc ctctccagca cccc                                  24

<210> SEQ ID NO 109
<211> LENGTH: 24
<212> TYPE: DNA
<213> ORGANISM: Hordeum vulgare

<400> SEQUENCE: 109
ggggtgctgg agaggcccag gtgg                                  24
```

<210> SEQ ID NO 110
<211> LENGTH: 24
<212> TYPE: DNA
<213> ORGANISM: Hordeum vulgare

<400> SEQUENCE: 110 gacccctct tcctcttctt cttg                                             24

<210> SEQ ID NO 111
<211> LENGTH: 24
<212> TYPE: DNA
<213> ORGANISM: Hordeum vulgare

<400> SEQUENCE: 111
cgttcttgag catgatgatg agga                                            24

<210> SEQ ID NO 112
<211> LENGTH: 21
<212> TYPE: DNA
<213> ORGANISM: Hordeum vulgare

<400> SEQUENCE: 112
gcaacaaagt cggtgaagag g                                               21

<210> SEQ ID NO 113
<211> LENGTH: 23
<212> TYPE: DNA
<213> ORGANISM: Hordeum vulgare

<400> SEQUENCE: 113
gtcagcatcc cgccgatgtt cag                                             23

<210> SEQ ID NO 114
<211> LENGTH: 23
<212> TYPE: DNA
<213> ORGANISM: Hordeum vulgare

<400> SEQUENCE: 114
ccacggcaga tgaggccagt gca                                             23

<210> SEQ ID NO 115
<211> LENGTH: 23
<212> TYPE: DNA
<213> ORGANISM: Hordeum vulgare

<400> SEQUENCE: 115
taaacgagct tgaggtggga ctg                                             23

<210> SEQ ID NO 116
<211> LENGTH: 22
<212> TYPE: DNA
<213> ORGANISM: Hordeum vulgare

<400> SEQUENCE: 116
aactgcagcc agagcaggat cg                                              22

<210> SEQ ID NO 117
<211> LENGTH: 22
<212> TYPE: DNA
<213> ORGANISM: Hordeum vulgare

<400> SEQUENCE: 117

```
agcaggccac cgaggtacag gt                                              22

<210> SEQ ID NO 118
<211> LENGTH: 21
<212> TYPE: DNA
<213> ORGANISM: Hordeum vulgare

<400> SEQUENCE: 118
ggcggcgcca gagaagcacc c                                               21

<210> SEQ ID NO 119
<211> LENGTH: 150
<212> TYPE: RNA
<213> ORGANISM: Hordeum vulgare

<400> SEQUENCE: 119
auggacgccu ucuacucgac cucgucggcg gcggcgagcg gcuggggcca cgacucccuc    60
aagaacuucc gccagaucuc ccccgccgug cagucccacc ucaagcucgu uuaccugacu   120
cuaugcuuug cacuggccuc aucugccgug                                    150

<210> SEQ ID NO 120
<211> LENGTH: 150
<212> TYPE: RNA
<213> ORGANISM: Hordeum vulgare

<400> SEQUENCE: 120
agggcgcacc auggcgacau ggacuacauc aagcacgccc ucacccucuu caccgacuuu    60
guugccgucc ucguccgagu ccucaucauc augcucaaga acgcaggcga caagucggag   120
gacaagaaga agaggaagag ggguccuga                                     150

<210> SEQ ID NO 121
<211> LENGTH: 150
<212> TYPE: RNA
<213> ORGANISM: Hordeum vulgare

<400> SEQUENCE: 121
cgcuuguguc ggaacuaucg ccuggauguu cucggugcca gucuaugagg agaggaagag    60
guuugggcug cugaugggug cagcccuccu ggaaggggcu ucgguuggac cucugauuga   120
gcuugccaua gacuuugacc caagcauccu                                    150

<210> SEQ ID NO 122
<211> LENGTH: 31
<212> TYPE: DNA
<213> ORGANISM: Artificial sequence
<220> FEATURE:
<223> OTHER INFORMATION: Synthetic

<400> SEQUENCE: 122
ttgaatcgaa gaaggaattg aaggagtcca t                                    31

<210> SEQ ID NO 123
<211> LENGTH: 28
<212> TYPE: DNA
<213> ORGANISM: Artificial sequence
<220> FEATURE:
<223> OTHER INFORMATION: Synthetic

<400> SEQUENCE: 123
aggtaagccc caacagccgc agcaacca                                        28
```

<210> SEQ ID NO 124
<211> LENGTH: 29
<212> TYPE: DNA
<213> ORGANISM: Artificial sequence
<220> FEATURE:
<223> OTHER INFORMATION: Synthetic

<400> SEQUENCE: 124
ctcttttcct ctcttcaaaa ggaggtgtc                                29

<210> SEQ ID NO 125
<211> LENGTH: 27
<212> TYPE: DNA
<213> ORGANISM: Artificial sequence
<220> FEATURE:
<223> OTHER INFORMATION: Synthetic

<400> SEQUENCE: 125
tgcactaaag ataaggcttg gatcgat                                  27

<210> SEQ ID NO 126
<211> LENGTH: 27
<212> TYPE: DNA
<213> ORGANISM: Artificial sequence
<220> FEATURE:
<223> OTHER INFORMATION: Synthetic

<400> SEQUENCE: 126
atccagaaga aaccaagcca ccaaggt                                  27

<210> SEQ ID NO 127
<211> LENGTH: 27
<212> TYPE: DNA
<213> ORGANISM: Artificial sequence
<220> FEATURE:
<223> OTHER INFORMATION: Synthetic

<400> SEQUENCE: 127
cctacaaaca ccaaaagccc aaagtac                                  27

<210> SEQ ID NO 128
<211> LENGTH: 29
<212> TYPE: DNA
<213> ORGANISM: Artificial sequence
<220> FEATURE:
<223> OTHER INFORMATION: Synthetic

<400> SEQUENCE: 128
actgcaacca aatcggtaaa caaggtcaa                                29

<210> SEQ ID NO 129
<211> LENGTH: 25
<212> TYPE: DNA
<213> ORGANISM: Artificial sequence
<220> FEATURE:
<223> OTHER INFORMATION: Synthetic

<400> SEQUENCE: 129
tcaatctctc ctcttctttt tcttc                                    25

<210> SEQ ID NO 130
<211> LENGTH: 27
<212> TYPE: DNA
<213> ORGANISM: Artificial sequence
<220> FEATURE:
<223> OTHER INFORMATION: Synthetic

<400> SEQUENCE: 130
tcaagggacc aacgaaggct aatttcg                              27

<210> SEQ ID NO 131
<211> LENGTH: 26
<212> TYPE: DNA
<213> ORGANISM: Artificial sequence
<220> FEATURE:
<223> OTHER INFORMATION: Synthetic

<400> SEQUENCE: 131
ggctttgaat tcaacaccc ctaatt                                26

<210> SEQ ID NO 132
<211> LENGTH: 26
<212> TYPE: DNA
<213> ORGANISM: Artificial sequence
<220> FEATURE:
<223> OTHER INFORMATION: Synthetic

<400> SEQUENCE: 132
gcttgcaatc ggagaaacac aaattt                               26

<210> SEQ ID NO 133
<211> LENGTH: 25
<212> TYPE: DNA
<213> ORGANISM: Artificial sequence
<220> FEATURE:
<223> OTHER INFORMATION: Synthetic

<400> SEQUENCE: 133
atggggactt gaagaaagtg tccat                                25

<210> SEQ ID NO 134
<211> LENGTH: 28
<212> TYPE: DNA
<213> ORGANISM: Artificial sequence
<220> FEATURE:
<223> OTHER INFORMATION: Synthetic

<400> SEQUENCE: 134
taaaataaac cagtttgatg tgattctg                             28

<210> SEQ ID NO 135
<211> LENGTH: 27
<212> TYPE: DNA
<213> ORGANISM: Artificial sequence
<220> FEATURE:
<223> OTHER INFORMATION: Synthetic

<400> SEQUENCE: 135
tgctcccaat ggaagccacc gtggtga                              27

<210> SEQ ID NO 136
<211> LENGTH: 28
<212> TYPE: DNA
<213> ORGANISM: Artificial sequence
<220> FEATURE:
<223> OTHER INFORMATION: Synthetic

<400> SEQUENCE: 136
aatcagaggt ccaatggaag caccctga                             28

<210> SEQ ID NO 137
<211> LENGTH: 28

```
<212> TYPE: DNA
<213> ORGANISM: Artificial sequence
<220> FEATURE:
<223> OTHER INFORMATION: Synthetic

<400> SEQUENCE: 137
gccttgcaac taaggctact gcagaaaa                                          28

<210> SEQ ID NO 138
<211> LENGTH: 28
<212> TYPE: DNA
<213> ORGANISM: Artificial sequence
<220> FEATURE:
<223> OTHER INFORMATION: Synthetic

<400> SEQUENCE: 138
agagctatag agcccccaaa gagagagg                                          28

<210> SEQ ID NO 139
<211> LENGTH: 27
<212> TYPE: DNA
<213> ORGANISM: Artificial sequence
<220> FEATURE:
<223> OTHER INFORMATION: Synthetic

<400> SEQUENCE: 139
tccaggtcac caaagtgagc cctctca                                           27

<210> SEQ ID NO 140
<211> LENGTH: 27
<212> TYPE: DNA
<213> ORGANISM: Artificial sequence
<220> FEATURE:
<223> OTHER INFORMATION: Synthetic

<400> SEQUENCE: 140
cttctcattt ctcttagatg aattatt                                           27

<210> SEQ ID NO 141
<211> LENGTH: 25
<212> TYPE: DNA
<213> ORGANISM: Artificial sequence
<220> FEATURE:
<223> OTHER INFORMATION: Synthetic

<400> SEQUENCE: 141
gttgtagttg tactccatct tattg                                             25

<210> SEQ ID NO 142
<211> LENGTH: 200
<212> TYPE: RNA
<213> ORGANISM: Cucumber

<400> SEQUENCE: 142
acuaucggau guauuacaug gcuaauggcc acuccuccuu augaagagaa aaagagggcc       60
ucuauuuuac uuggggcugc ucuucucgaa ggggcuucca uugguccuuu gaucagucug      120
gcuauugauu uugacccaag uguucgggug agcgcuuucg ugggaacugc gguugccuuu      180
uguuguuucu caggagcagc                                                  200

<210> SEQ ID NO 143
<211> LENGTH: 200
<212> TYPE: RNA
<213> ORGANISM: Cucumber
```

```
<400> SEQUENCE: 143
cuuuaucucg guggcuuacu uucuuccggu guauccaugu uacucugguu acauuucgcc    60
uccucuuuau ucgguggguuc uacugcccuu uucaaguugu aguuguacuu ugggcuguug   120 guuuuguug gcuacauggu aguugauacu caggaaauaa uugagauggc acauaugggu    180
gauauggauu augugaaaca                                               200

<210> SEQ ID NO 144
<211> LENGTH: 200
<212> TYPE: RNA
<213> ORGANISM: Cucumber

<400> SEQUENCE: 144
auggaugccu uuucaucuuu cuucgauucu caacaaccuu cuacaaaccc uuggaccuac    60
gauucucuca agaauuuccg gcagauuucc cccgucguuc aaucucaucu ccaccagguu   120
uaccuuacuc ugggugugc uuugguugca ucugcugcug gagcuuaucu ccauauucg    180 uggaacauug gcggaauccu                                               200

<210> SEQ ID NO 145
<211> LENGTH: 200
<212> TYPE: RNA
<213> ORGANISM: Cucumber

<400> SEQUENCE: 145
auuggaugca ucacauggcu aauggccacu ccuccuuaug aagagagaaa gaggcuuucu    60
auguuaaugg cggcugcucu ucuugaagga gcaucaauug guccuuugau ugggguuggcu   120 aucgagauug auccaagugu ucggucagu gccuuugugg gaacugcugu ggcuuuuggu   180
uguuucucug cagcagccau                                               200

<210> SEQ ID NO 146
<211> LENGTH: 200
<212> TYPE: RNA
<213> ORGANISM: Cucumber

<400> SEQUENCE: 146
cuuuaccugg guggcuuacu uucuucuggg auauccaugu uacucugguu gcauuucgcu    60
ucaucuauau ucgguggguuc uacugcucuu uucaaguuug aguuguacuu ugggcuauug   120
cuguuugugg gcuacauggu aguugauacu caagaaauaa ucgagagggc ucaucuuggu   180
gauauggacu augugaagca                                               200

<210> SEQ ID NO 147
<211> LENGTH: 202
<212> TYPE: RNA
<213> ORGANISM: Aqueoria victoria

<400> SEQUENCE: 147
guucgagggc gauacccugg ugaaucgcau cgagcugacc ggcaccgauu ucaaggagga    60
uggcaacauc cugggcaaua agauggagua caacacaac gcccacaaug uguacaucau   120
gaccgacaag gccaagaaug gcaucaaggu gaacuucaag auccgccaca acaucgagga   180
uggcagcgug cagcuggccg ac                                            202
```

METHODS AND COMPOSITIONS FOR PLANT PEST CONTROL

CROSS REFERENCE TO RELATED APPLICATIONS

This U.S. Non-provisional patent application claims the benefit of U.S. Provisional Patent Application No. 61/757,291, which was filed Jan. 28, 2013 and is incorporated herein by reference in its entirety.

INCORPORATION OF SEQUENCE LISTING

A text file of the Sequence Listing contained in the file named "MON58632C_SEQ_LISTING.TXT" which is 94,742 bytes (measured in MS-Windows®) in size and which was created on Jan. 27, 2014, is electronically filed herewith and is incorporated herein by reference in its entirety. This Sequence Listing consists of SEQ ID NO:1-147.

BACKGROUND

Powdery mildews are fungal diseases that affect a wide range of plants including cereals, grasses, vegetables, ornamentals, weeds, shrubs, fruit trees, broad-leaved shade and forest trees, that is caused by different species of fungi in the order Erysiphales. The disease is characterized by spots or patches of white to grayish, talcum-powder-like growth that produce tiny, pinhead-sized, spherical fruiting structures (the cleistothecia or overwintering bodies of the fungus), that are first white, later yellow-brown and finally black. The fungi that cause powdery mildews are host specific and cannot survive without the proper host plant. They produce mycelium (fungal threads) that grow only on the surface of the plant and feed by sending haustoria, or root-like structures, into the epidermal cells of the plant. The fungi overwinter on plant debris as cleistothecia or mycelia. In the spring, the cleistothecia produce spores that are moved to susceptible hosts by rain, wind or insects.

Powdery mildew disease is particularly prevalent in temperate and humid climates, where they frequently cause significant yield losses and quality reductions in various agricultural settings including greenhouse and field farming. This affects key cereals (e.g. barley and wheat), horticultural crops (e.g. grapevine, pea and tomato) and economically important ornamentals (e.g. roses). Limited access to natural sources of resistance to powdery mildews, rapid changes in pathogen virulence and the time consuming introgression of suitable resistance genes into elite varieties has led to the widespread use of fungicides to control the disease. This has not surprisingly led to the evolution and spread of fungicide resistance, which is especially dramatic amongst the most economically important powdery mildews.

Downy mildew diseases are caused by oomycete microbes from the family Peronosporaceae that are parasites of plants. Peronosporaceae are obligate biotrophic plant pathogens and parasitize their host plants as an intercellular mycelium using haustoria to penetrate the host cells. The downy mildews reproduce asexually by forming sporangia on distinctive white sporangiophores usually formed on the lower surface of infected leaves. These constitute the "downy mildew" and the initial symptoms appear on leaves as light green to yellow spots. The sporangia are wind-dispersed to the surface of other leaves. Depending on the genus, the sporangia may germinate by forming zoospores or by germ-tube. In the latter case, the sporangia behave like fungal conidia and are often referred to as such. Sexual reproduction is via oospores.

Most Peronosporaceae are pathogens of herbaceous dicots. Some downy mildew genera have relatively restricted host ranges, e.g. *Basidiophora, Paraperonospora, Protobremia* and *Bremia* on Asteraceae; *Perofascia* and *Hyaloperonospora* almost exclusively on Brassicaceae; *Viennotia, Graminivora, Poakatesthia, Sclerospora* and *Peronosclerospora* on Poaceae, *Plasmoverna* on Ranunculaceae. However, the largest genera, *Peronospora* and *Plasmopara*, have very wide host ranges.

Rusts (Pucciniales, formerly Uredinales) are obligate biotrophic parasites of vascular plants. Rusts affect a variety of plants; leaves, stems, fruits and seeds and is most commonly seen as coloured powder, composed of tiny aeciospores which land on vegetation producing pustules, or uredia, that form on the lower surfaces. During late spring or early summer, yellow orange or brown, hairlike or ligulate structures called telia grow on the leaves or emerge from bark of woody hosts. These telia produce teliospores which will germinate into aerial basidiospores, spreading and causing further infection.

SUMMARY

The present embodiments provide for compositions comprising polynucleotide molecules and methods for treating a plant to alter or regulate gene or gene transcript expression in the plant, for example, by providing RNA or DNA for inhibition of expression. Various aspects provide compositions comprising polynucleotide molecules and related methods for topically applying such compositions to plants to regulate endogenous BAX inhibitor 1 (BI-1) genes in a plant cell. The polynucleotides, compositions, and methods disclosed herein are useful in decreasing levels of BI-1 transcript and improving fungal disease resistance of a plant. Provided herein are compositions and methods that increase plant resistance to powdery mildew, downy mildew, rust infection or other fungal pathogens by suppression of plant BAX inhibitor 1 (BI-1) genes.

In one aspect, polynucleotide molecules are provided in compositions that can permeate or be absorbed into living plant tissue to initiate localized, partially systemic, or systemic gene inhibition or regulation. In certain embodiments, the polynucleotide molecules ultimately provide to a plant, or allow the in planta production of, RNA that is capable of hybridizing under physiological conditions in a plant cell to RNA transcribed from a target endogenous gene or target transgene in the plant cell, thereby effecting regulation of the endogenous BI-1 target gene. In certain embodiments, regulation of the BI-1 target genes, such as by silencing or suppression of the target gene, leads to the upregulation of another gene that is itself affected or regulated by decreasing the BI-1 target gene's expression.

In certain aspects or embodiments, the topical application of a composition comprising an exogenous polynucleotide and a transfer agent to a plant or plant part according to the methods described herein does not necessarily result in nor require the exogenous polynucleotide's integration into a chromosome of the plant. In certain aspects or embodiments, the topical application of a composition comprising an exogenous polynucleotide and a transfer agent to a plant or plant part according to the methods described herein does not necessarily result in nor require transcription of the exogenous polynucleotide from DNA integrated into a chromosome of the plant. In certain embodiments, topical application of a composition comprising an exogenous polynucleotide and a transfer agent to a plant according to the methods described herein also does not necessarily require that the exogenous polynucleotide be physically bound to a particle, such as in biolistic mediated introduction of polynucleotides associated with a gold or tungsten particles into internal portions of a plant, plant part, or plant cell. An exogenous polynucleotide used in certain methods and compositions provided herein can optionally be associated with an operably linked promoter sequence in certain embodiments of the methods provided herein. However, in other embodiments, an exogenous polynucleotide used in certain methods and compositions provided herein is not associated with an operably linked promoter sequence. Also, in certain embodiments, an exogenous polynucleotide used in certain methods and compositions provided herein is not operably linked to a viral vector.

In certain embodiments, methods for improving fungal disease resistance in a plant comprising topically applying compositions comprising a polynucleotide and a transfer agent that suppress the target BI-1 gene are provided. In certain embodiments, methods for selectively suppressing the target BI-1 gene by topically applying the polynucleotide composition to a plant surface at one or more selected seed, vegetative, or reproductive stage(s) of plant growth are provided. Such methods can provide for gene suppression in a plant or plant part on an as needed or as desired basis. In certain embodiments, methods for selectively suppressing the target BI-1 gene by topically applying the polynucleotide composition to a plant surface at one or more pre-determined seed, vegetative, or reproductive stage(s) of plant growth are provided. Such methods can provide for BI-1 gene suppression in a plant or plant part that obviates any undesired or unnecessary effects of suppressing the genes expression at certain seed, vegetative, or reproductive stage(s) of plant development.

In certain embodiments, methods for selectively improving fungal disease resistance in a plant by topically applying the polynucleotide composition to the plant surface at one or more selected seed, vegetative, or reproductive stage(s) are provided. Such methods can provide for improved fungal disease resistance in a plant or plant part on an as needed or as desired basis. In certain embodiments, methods for selectively improving fungal disease resistance in a plant by topically applying the polynucleotide composition to the plant surface at one or more predetermined seed, vegetative, or reproductive stage(s) are provided. Such methods can provide for improving fungal disease resistance in a plant or plant part that obviates any undesired or unnecessary effects of suppressing BI-1 gene expression at certain seed, vegetative, or reproductive stage(s) of plant development.

Methods and compositions that provide for the topical application of certain polynucleotides in the presence of transfer agents can be used to suppress BAX inhibitor 1 (BI-1) gene expression in an optimal manner. Topically induced BI-1 gene suppression methods and compositions provided herein can control the timing and degree of BI-1 knockdown to achieve fungal control while minimizing deleterious pleotropic effects in the host plant. In certain embodiments, the compositions provided herein can be applied on an "as needed" basis upon scouting for the occurrence of fungal disease. In certain embodiments, the compositions can be applied in a manner that obviates any deleterious effects on yield or other characteristics that can be associated with suppression of BI-1 gene expression in a crop plant. The applied polynucleotides are complementary to the BI-1 target host gene in plants and their topical application leads to suppression of the BI-1 gene.

Provided herein are compositions and methods for controlling plant fungal diseases. Plant fungal diseases that can be controlled with the methods and compositions provided herein include, but are not limited to, obligate biotrophic powdery mildew, downy mildew, and rust fungal infestations in plants. Plant fungal diseases that can be controlled with the methods and compositions provided herein also include, but are not limited to, fungal pathogens such as those causing anthracnose stalk rot, *Diplodia* Stalk or Ear Rot, *Gibberella* Stalk or Ear Rot, and *Fusarium* Stalk Rot in corn, or causing Take-all in wheat, *Fusarium* head blight in barley and wheat, or causing rice blast. In certain embodiments, methods and compositions for reducing expression of one or more host plant BI-1 polynucleotide and/or protein molecules in one or more cells or tissues of the plant such that the plant is rendered less susceptible to fungal infections from the order Erysiphales, the family Peronosporaceae or the order Pucciniales, are provided. In certain embodiments, nucleotide and amino acid sequences of plant BAX inhibitor 1 (BI-1) genes which can be downregulated by methods and compositions provided herein to increase plant resistance to powdery mildew, downy mildew, rust infection, or fungal pathogens such as those causing anthracnose stalk rot, *Diplodia* Stalk or Ear Rot, *Gibberella* Stalk or Ear Rot, and *Fusarium* Stalk Rot in corn, or causing Take-all in wheat, *Fusarium* head blight in barley and wheat, or causing rice blast are disclosed. Examples of powdery mildew fungi of the order Erysiphales which are controlled by the compositions and methods provided herein include, but are not limited to, *Blumeria graminis* f. sp. *hordei, Blumeria graminis* forma specialis (f. sp.) *tritici, Golovinomyces orontii, Golovinomyces cichoracearum, Oidium neolycopersici, Oidium lycopersici, Erysiphe pisi, Erisyphe necator* and *Sphaerotheca fuliginea* among others. Examples of downy mildew of the family Peronosporaceae include *Pseudoperonospora humuli, Pseudoperonospora cubensis, Plasmopara viticola, Peronospora tabacina, Bremia lactucae*, and *Plasmopara halstedii*. Examples of rusts of the order Pucciniales which are controlled by the compositions and methods provided herein include, but are not limited to, *Phakopsora meibomiae, Phakopsora pachyrhizi, Puccinia graminis, Puccinia recondita, Uromyces phaseoli* and *Uromyces appendeculatus*. Other examples of fungal pathogens which are controlled by the compositions and methods provided herein include, but are not limited to, *Colletotrichum graminicola, Stenocarpella* (or *Diplodia*) *maydis, Gibberella zeae, Fusarium moniliforme, Gaeumannomyces graminis, Fusarium graminearum, Magnaporthe grisea* (also known as *Pyricularia grisea* or *Pyricularia oryzae*), *Septoria nodorum*, and *Septoria tritici*.

Examples of plants protected by the compositions and methods provided herein include, but are not limited to, barley, rye, wheat, rice, oats, corn, sorghum, switchgrass, and sugar cane.

Also provided are methods and compositions where topically induced reductions in BI-1 transcript or protein levels are used to achieve fungal disease control while minimizing deleterious pleotropic effects in the host plant. Such methods and compositions provide for optimized levels of BI-1 gene inhibition and/or optimized timing of BI-1 gene inhibition.

Polynucleotides that can be used to suppress a BI-1 include, but are not limited to, any of: i) polynucleotides comprising at least 18 contiguous nucleotides that are essentially identical or essentially complementary to a BI-1 gene or to a transcript of the gene of SEQ ID NO:2, 4, 6, 8, 10, 12, 14, 16, 18, 20, 22, 24, 26, 28, 30, or 32 or Example 5; or ii) polynucleotides comprising at least 18 contiguous nucleotides that are essentially identical or essentially complementary to a polynucleotide of SEQ ID NO:33-106, 109-140, or 142-146 as provided herein.

Certain embodiments are directed to a method for producing a plant exhibiting an improvement in fungal disease resistance comprising topically applying to a plant surface a composition that comprises:
a. at least one polynucleotide that comprises at least 18 contiguous nucleotides that are essentially identical or essentially complementary to a BAX inhibitor 1 (BI-1) gene or to a transcript of the gene; and
b. a transfer agent, wherein the plant exhibits an improvement in fungal disease resistance that results from suppression of the BAX inhibitor 1 (BI-1) gene. In certain embodiments of the methods, the polynucleotide molecule comprises sense ssDNA, sense ssRNA, dsRNA, dsDNA, a double stranded DNA/RNA hybrid, anti-sense ssDNA, or anti-sense ssRNA. In certain embodiments of the methods, the polynucleotide is selected from the group consisting of SEQ ID NO: 33-106, 109-140, and 142-146, or wherein the polynucleotide comprises at least 18 contiguous nucleotides that are essentially identical or essentially complementary to SEQ ID NO: 2, 4, 6, 8, 10, 12, 14, 16, 18, 20, 22, 24, 26, 28, 30, or 32. In certain embodiments of the methods: (a) the plant is a barley plant, the gene or the transcript is a barley BAX inhibitor 1 (BI-1) gene or transcript, and the polynucleotide molecule is selected from the group consisting of SEQ ID NO: 73-76, 93-106, 109-120, and 121, and 121, or the polynucleotide comprises at least 18 contiguous nucleotides that are essentially identical or essentially complementary to SEQ ID NO:24; (b) the plant is a rice plant, the gene or the transcript is a rice BAX inhibitor 1 (BI-1) gene or transcript, and the polynucleotide molecule is selected from the group consisting of SEQ ID NO: 77-79, and 80, or the polynucleotide comprises at least 18 contiguous nucleotides that are essentially identical or essentially complementary to SEQ ID NO: 26; (c) the plant is a wheat plant, the gene or the transcript is a wheat BAX inhibitor 1 (BI-1) gene or transcript, and the polynucleotide molecule is selected from the group consisting of SEQ ID NO:61-67, and 68, or the polynucleotide comprises at least 18 contiguous nucleotides that are essentially identical or essentially complementary to a wheat gene or transcript that encodes SEQ ID NO:18 or 20; (d) the plant is a soybean plant, the gene or the transcript is a soybean BAX inhibitor 1 (BI-1) gene or transcript, and the polynucleotide molecule is selected from the group consisting of SEQ ID NO: 49-52, 69-72, and 122-140, or the polynucleotide comprises at least 18 contiguous nucleotides that are essentially identical or essentially complementary to SEQ ID NO: 12 or 22; (e) the plant is a corn plant, the gene or the transcript is a corn BAX inhibitor 1 (BI-1) gene or transcript, and the polynucleotide molecule is selected from the group consisting of SEQ ID NO:57-59, and 60, or the polynucleotide comprises at least 18 contiguous nucleotides that are essentially identical or essentially complementary to SEQ ID NO: 16; (f) the plant is a sorghum plant, the gene or the transcript is a sorghum BAX inhibitor 1 (BI-1) gene or transcript, and the polynucleotide molecule is selected from the group consisting of SEQ ID NO: 53-55, and 56, or the polynucleotide comprises at least 18 contiguous nucleotides that are essentially identical or essentially complementary to SEQ ID NO: 14; (g) the plant is a pepper plant, the gene or the transcript is a pepper BAX inhibitor 1 (BI-1) gene or transcript, and the polynucleotide molecule is selected from the group consisting of SEQ ID NO: 45-47, and 48, or the polynucleotide comprises at least 18 contiguous nucleotides that are essentially identical or essentially complementary to SEQ ID NO: 10; (h) the plant is a grape plant, the gene or the transcript is a grape BAX inhibitor 1 (BI-1) gene or transcript, and the polynucleotide molecule is selected from the group consisting of SEQ ID NO:41-43, and 44, or the polynucleotide comprises at least 18 contiguous nucleotides that are essentially identical or essentially complementary to SEQ ID NO: 8; (i) the plant is a tomato plant, the gene or the transcript is a tomato BAX inhibitor 1 (BI-1) gene or transcript, and the polynucleotide molecule is selected from the group consisting of SEQ ID NO:37-39, and 40, or the polynucleotide comprises at least 18 contiguous nucleotides that are essentially identical or essentially complementary to SEQ ID NO: 6; (j) the plant is a lettuce plant, the gene or the transcript is a lettuce BAX inhibitor 1 (BI-1) gene or transcript, and the polynucleotide molecule is selected from the group consisting of SEQ ID NO:33-35, and 36, or the polynucleotide comprises at least 18 contiguous nucleotides that are essentially identical or essentially complementary to SEQ ID NO: 4; (k) the plant is a cucumber plant, the gene or the transcript is a cucumber BAX inhibitor 1 (BI-1) gene or transcript, and the polynucleotide molecule is selected from the group consisting of SEQ ID NO:81-88, and 142-146, or the polynucleotide comprises at least 18 contiguous nucleotides that are essentially identical or essentially complementary to SEQ ID NO: 28 or 30; or (l) the plant is a cotton plant, the gene or the transcript is a cotton BAX inhibitor 1 (BI-1) gene or transcript, and the polynucleotide molecule is selected from the group consisting of SEQ ID NO:89-91, and 92, or the polynucleotide comprises at least 18 contiguous nucleotides that are essentially identical or essentially complementary to SEQ ID NO: 32. In certain embodiments of the methods, the composition comprises any combination of two or more polynucleotide molecules. In certain embodiments of the methods, the polynucleotide is at least 18 to about 24, about 25 to about 50, about 51 to about 100, about 101 to about 300, about 301 to about 500, or at least about 500 or more residues in length. In certain embodiments of the methods, the composition further comprises a non-polynucleotide herbicidal molecule, a polynucleotide herbicidal molecule, a polynucleotide that suppresses an herbicide target gene, an insecticide, a fungicide, a nematocide, or a combination thereof. In certain embodiments of the methods, the composition further comprises a non-polynucleotide herbicidal molecule and the plant is resistant to the herbicidal molecule. In certain embodiments of the methods, the transfer agent comprises an organosilicone preparation. In certain embodiments of the methods, the polynucleotide is not operably linked to a viral vector. In certain embodiments of the methods, the polynucleotide is not integrated into the plant chromosome.

Further embodiments are directed to: a plant made according to the above-described methods; progeny of the plant that exhibit fungal disease resistance; seed of the plant, wherein seed from the plant exhibits fungal disease resistance; and a processed product of the plant, the progeny plant, or the seed, wherein the processed product exhibits fungal disease resistance. In certain embodiments, the processed product exhibits an improved attribute relative to a processed product of an untreated control plant and the improved attribute results from the improved fungal disease resistance. An improved attribute of a processed product can include, but is not limited to, decreased mycotoxin content, improved nutritional content, improved storage characteristics, improved flavor, improved consistency, and the like when compared to a processed product obtained from an untreated plant or plant part.

Additional embodiments are directed to compositions comprising a polynucleotide molecule that comprises at least 18 contiguous nucleotides that are essentially identical or essentially complementary to a BAX inhibitor 1 (BI-1) gene or transcript of the gene, wherein the polynucleotide is not operably linked to a promoter; and, b) a transfer agent. In certain embodiments of the composition, the polynucleotide is selected from the group consisting of wherein the polynucleotide is selected from the group consisting of SEQ ID NO: 33-106, 109-140, and 142-146, or wherein the polynucleotide comprises at least 18 contiguous nucleotides that are essentially identical or essentially complementary to SEQ ID NO: 2, 4, 6, 8, 10, 12, 14, 16, 18, 20, 22, 24, 26, 28, 30, or 32. In certain embodiments of the composition: (a) the gene or the transcript is a barley BAX inhibitor 1 (BI-1) gene or transcript, and the polynucleotide molecule is selected from the group consisting of SEQ ID NO: 73-76, 93-106, 109-120, and 121, and 121, or the polynucleotide comprises at least 18 contiguous nucleotides that are essentially identical or essentially complementary to SEQ ID NO:24; (b) the gene or the transcript is a rice BAX inhibitor 1 (BI-1) gene or transcript, and the polynucleotide molecule is selected from the group consisting of SEQ ID NO: 77-79, and 80, or the polynucleotide comprises at least 18 contiguous nucleotides that are essentially identical or essentially complementary to SEQ ID NO: 26; (c) the gene or the transcript is a wheat BAX inhibitor 1 (BI-1) gene or transcript, and the polynucleotide molecule is selected from the group consisting of SEQ ID NO:61-67, and 68, or the polynucleotide comprises at least 18 contiguous nucleotides that are essentially identical or essentially complementary to a wheat gene or transcript that encodes SEQ ID NO:18 or 20; (d) the gene or the transcript is a soybean BAX inhibitor 1 (BI-1) gene or transcript, and the polynucleotide molecule is selected from the group consisting of SEQ ID NO: 49-52, 69-72, and 122-140, or the polynucleotide comprises at least 18 contiguous nucleotides that are essentially identical or essentially complementary to SEQ ID NO: 12 or 22; (e) the gene or the transcript is a corn BAX inhibitor 1 (BI-1) gene or transcript, and the polynucleotide molecule is selected from the group consisting of SEQ ID NO:57-59, and 60, or the polynucleotide comprises at least 18 contiguous nucleotides that are essentially identical or essentially complementary to SEQ ID NO: 16; (f) the gene or the transcript is a sorghum BAX inhibitor 1 (BI-1) gene or transcript, and the polynucleotide molecule is selected from the group consisting of SEQ ID NO: 53-55, and 56, or the polynucleotide comprises at least 18 contiguous nucleotides that are essentially identical or essentially complementary to SEQ ID NO: 14; (g) the gene or the transcript is a pepper BAX inhibitor 1 (BI-1) gene or transcript, and the polynucleotide molecule is selected from the group consisting of SEQ ID NO: 45-47, and 48, or the polynucleotide comprises at least 18 contiguous nucleotides that are essentially identical or essentially complementary to SEQ ID NO: 10; (h) the gene or the transcript is a grape BAX inhibitor 1 (BI-1) gene or transcript, and the polynucleotide molecule is selected from the group consisting of SEQ ID NO:41-43, and 44, or the polynucleotide comprises at least 18 contiguous nucleotides that are essentially identical or essentially complementary to SEQ ID NO: 8; (i) the gene or the transcript is a tomato BAX inhibitor 1 (BI-1) gene or transcript, and the polynucleotide molecule is selected from the group consisting of SEQ ID NO:37-39, and 40, or the polynucleotide comprises at least 18 contiguous nucleotides that are essentially identical or essentially complementary to SEQ ID NO: 6; (j) the gene or the transcript is a lettuce BAX inhibitor 1 (BI-1) gene or transcript, and the polynucleotide molecule is selected from the group consisting of SEQ ID NO:33-35, and 36, or the polynucleotide comprises at least 18 contiguous nucleotides that are essentially identical or essentially complementary to SEQ ID NO: 4; (k) the gene or the transcript is a cucumber BAX inhibitor 1 (BI-1) gene or transcript, and the polynucleotide molecule is selected from the group consisting of SEQ ID NO:81-88, and 142-146, or the polynucleotide comprises at least 18 contiguous nucleotides that are essentially identical or essentially complementary to SEQ ID NO: 28 or 30; or (l) the gene or the transcript is a cotton BAX inhibitor 1 (BI-1) gene or transcript, and the polynucleotide molecule is selected from the group consisting of SEQ ID NO:89-91, and 92, or the polynucleotide comprises at least 18 contiguous nucleotides that are essentially identical or essentially complementary to SEQ ID NO: 32. In certain embodiments of the composition, the polynucleotide is at least 18 to about 24, about 25 to about 50, about 51 to about 100, about 101 to about 300, about 301 to about 500, or at least about 500 or more residues in length. In certain embodiments of the composition, the composition further comprises a non-polynucleotide herbicidal molecule, a polynucleotide herbicidal molecule, a polynucleotide that suppresses an herbicide target gene, an insecticide, a fungicide, a nematocide, or a combination thereof. In certain embodiments of the composition, the transfer agent is an organosilicone preparation. In certain embodiments of the composition, the polynucleotide is not physically bound to a biolistic particle.

Other embodiments are directed to a method of making a composition comprising the step of combining at least: a) a polynucleotide molecule comprising at least 18 contiguous nucleotides that are essentially identical or essentially complementary to a BAX inhibitor 1 (BI-1) gene or transcript of a plant, wherein the polynucleotide is not operably linked to a promoter or a viral vector; and, b) a transfer agent. In certain embodiments of the methods, the polynucleotide is obtained by in vivo biosynthesis, in vitro enzymatic synthesis, or chemical synthesis. In certain embodiments, the methods further comprises combining with the polynucleotide and the transfer agent at least one of a non-polynucleotide herbicidal molecule, a polynucleotide herbicidal molecule, an insecticide, a fungicide, and/or a nematocide. In certain embodiments of the methods, the transfer agent is an organosilicone preparation.

Yet another embodiment is directed to a method of identifying a polynucleotide for improving fungal disease resistance in a plant comprising; a) selecting a population of polynucleotides that are essentially identical or essentially complementary to a BAX inhibitor 1 (BI-1) gene or transcript of a plant; b) topically applying to a surface of at least one of the plants a composition comprising at least one polynucleotide from the population and an transfer agent to obtain a treated plant; and, c) identifying a treated plant that exhibits suppression of the BAX inhibitor 1 (BI-1) gene or exhibits an improvement in fungal disease resistance, thereby identifying a polynucleotide that improves fungal disease resistance in the plant. In certain embodiments of the methods, the polynucleotide is selected from the group consisting of wherein the polynucleotide is selected from the group consisting of SEQ ID NO: 33-106, 109-140, and 142-146, or wherein the polynucleotide comprises at least 18 contiguous nucleotides that are essentially identical or essentially complementary to SEQ ID NO: 2, 4, 6, 8, 10, 12, 14, 16, 18, 20, 22, 24, 26, 28, 30, or 32. In certain embodiments of the methods: a) the plant is a barley plant, the gene or the transcript is a barley BAX inhibitor 1 (BI-1) gene or transcript, and the polynucleotide molecule is selected from the group consisting of SEQ ID NO: 73-76, 93-106, 109-120, and 121, and 121, or the polynucleotide comprises at least 18 contiguous nucleotides that are essentially identical or essentially complementary to SEQ ID NO:24; (b) the plant is a rice plant, the gene or the transcript is a rice BAX inhibitor 1 (BI-1) gene or transcript, and the polynucleotide molecule is selected from the group consisting of SEQ ID NO: 77-79, and 80, or the polynucleotide comprises at least 18 contiguous nucleotides that are essentially identical or essentially complementary to SEQ ID NO: 26; (c) the plant is a wheat plant, the gene or the transcript is a wheat BAX inhibitor 1 (BI-1) gene or transcript, and the polynucleotide molecule is selected from the group consisting of SEQ ID NO:61-67, and 68, or the polynucleotide comprises at least 18 contiguous nucleotides that are essentially identical or essentially complementary to a wheat gene or transcript that encodes SEQ ID NO:18 or 20; (d) the plant is a soybean plant, the gene or the transcript is a soybean BAX inhibitor 1 (BI-1) gene or transcript, and the polynucleotide molecule is selected from the group consisting of SEQ ID NO: 49-52, 69-72, and 122-140, or the polynucleotide comprises at least 18 contiguous nucleotides that are essentially identical or essentially complementary to SEQ ID NO: 12 or 22; (e) the plant is a corn plant, the gene or the transcript is a corn BAX inhibitor 1 (BI-1) gene or transcript, and the polynucleotide molecule is selected from the group consisting of SEQ ID NO:57-59, and 60, or the polynucleotide comprises at least 18 contiguous nucleotides that are essentially identical or essentially complementary to SEQ ID NO: 16; (f) the plant is a sorghum plant, the gene or the transcript is a sorghum BAX inhibitor 1 (BI-1) gene or transcript, and the polynucleotide molecule is selected from the group consisting of SEQ ID NO: 53-55, and 56, or the polynucleotide comprises at least 18 contiguous nucleotides that are essentially identical or essentially complementary to SEQ ID NO: 14; (g) the plant is a pepper plant, the gene or the transcript is a pepper BAX inhibitor 1 (BI-1) gene or transcript, and the polynucleotide molecule is selected from the group consisting of SEQ ID NO: 45-47, and 48, or the polynucleotide comprises at least 18 contiguous nucleotides that are essentially identical or essentially complementary to SEQ ID NO: 10; (h) the plant is a grape plant, the gene or the transcript is a grape BAX inhibitor 1 (BI-1) gene or transcript, and the polynucleotide molecule is selected from the group consisting of SEQ ID NO:41-43, and 44, or the polynucleotide comprises at least 18 contiguous nucleotides that are essentially identical or essentially complementary to SEQ ID NO: 8; (i) the plant is a tomato plant, the gene or the transcript is a tomato BAX inhibitor 1 (BI-1) gene or transcript, and the polynucleotide molecule is selected from the group consisting of SEQ ID NO:37-39, and 40, or the polynucleotide comprises at least 18 contiguous nucleotides that are essentially identical or essentially complementary to SEQ ID NO: 6; (j) the plant is a lettuce plant, the gene or the transcript is a lettuce BAX inhibitor 1 (BI-1) gene or transcript, and the polynucleotide molecule is selected from the group consisting of SEQ ID NO:33-35, and 36, or the polynucleotide comprises at least 18 contiguous nucleotides that are essentially identical or essentially complementary to SEQ ID NO: 4; (k) the plant is a cucumber plant, the gene or the transcript is a cucumber BAX inhibitor 1 (BI-1) gene or transcript, and the polynucleotide molecule is selected from the group consisting of SEQ ID NO:81-88, and 142- 146, or the polynucleotide comprises at least 18 contiguous nucleotides that are essentially identical or essentially complementary to SEQ ID NO: 28 or 30; or (l) the plant is a cotton plant, the gene or the transcript is a cotton BAX inhibitor 1 (BI-1) gene or transcript, and the polynucleotide molecule is selected from the group consisting of SEQ ID NO:89-91, and 92, or the polynucleotide comprises at least 18 contiguous nucleotides that are essentially identical or essentially complementary to SEQ ID NO: 32.

A further embodiment is directed to a plant comprising an exogenous polynucleotide that comprises at least 18 contiguous nucleotides that are essentially identical or essentially complementary to a BAX inhibitor 1 (BI-1) gene or transcript of the gene, wherein the exogenous polynucleotide is not operably linked to a promoter or to a viral vector, is not integrated into the chromosomal DNA of the plant, and is not found in a non-transgenic plant; and, wherein the plant exhibits an improvement in fungal disease resistance that results from suppression of the BAX inhibitor 1 (BI-1) gene. In certain embodiments, the plant further comprises an organosilicone compound or a component thereof. In certain embodiments, the polynucleotide is selected from the group consisting of SEQ ID NO: 33-106, 109-140, and 142-146, or wherein the polynucleotide comprises at least 18 contiguous nucleotides that are essentially identical or essentially complementary to SEQ ID NO: 2, 4, 6, 8, 10, 12, 14, 16, 18, 20, 22, 24, 26, 28, 30, or 32. In certain embodiments: a) the plant is a barley plant, the gene or the transcript is a barley BAX inhibitor 1 (BI-1) gene or transcript, and the polynucleotide molecule is selected from the group consisting of SEQ ID NO: 73-76, 93-106, 109-120, and 121, and 121, or the polynucleotide comprises at least 18 contiguous nucleotides that are essentially identical or essentially complementary to SEQ ID NO:24; (b) the plant is a rice plant, the gene or the transcript is a rice BAX inhibitor 1 (BI-1) gene or transcript, and the polynucleotide molecule is selected from the group consisting of SEQ ID NO: 77-79, and 80, or the polynucleotide comprises at least 18 contiguous nucleotides that are essentially identical or essentially complementary to SEQ ID NO: 26; (c) the plant is a wheat plant, the gene or the transcript is a wheat BAX inhibitor 1 (BI-1) gene or transcript, and the polynucleotide molecule is selected from the group consisting of SEQ ID NO:61-67, and 68, or the polynucleotide comprises at least 18 contiguous nucleotides that are essentially identical or essentially complementary to a wheat gene or transcript that encodes SEQ ID NO:18 or 20; (d) the plant is a soybean plant, the gene or the transcript is a soybean BAX inhibitor 1 (BI-1) gene or transcript, and the polynucleotide molecule is selected from the group consisting of SEQ ID NO: 49-52, 69-72, and 122-140, or the polynucleotide comprises at least 18 contiguous nucleotides that are essentially identical or essentially complementary to SEQ ID NO: 12 or 22; (e) the plant is a corn plant, the gene or the transcript is a corn BAX inhibitor 1 (BI-1) gene or transcript, and the polynucleotide molecule is selected from the group consisting of SEQ ID NO:57-59, and 60, or the polynucleotide comprises at least 18 contiguous nucleotides that are essentially identical or essentially complementary to SEQ ID NO: 16; (f) the plant is a sorghum plant, the gene or the transcript is a sorghum BAX inhibitor 1 (BI-1) gene or transcript, and the polynucleotide molecule is selected from the group consisting of SEQ ID NO: 53-55, and 56, or the polynucleotide comprises at least 18 contiguous nucleotides that are essentially identical or essentially complementary to SEQ ID NO: 14; (g) the plant is a pepper plant, the gene or the transcript is a pepper BAX inhibitor 1 (BI-1) gene or transcript, and the polynucleotide molecule is selected from the group consisting of SEQ ID NO: 45-47, and 48, or the polynucleotide comprises at least 18 contiguous nucleotides that are essentially identical or essentially complementary to SEQ ID NO: 10; (h) the plant is a grape plant, the gene or the transcript is a grape BAX inhibitor 1 (BI-1) gene or transcript, and the polynucleotide molecule is selected from the group consisting of SEQ ID NO:41-43, and 44, or the polynucleotide comprises at least 18 contiguous nucleotides that are essentially identical or essentially complementary to SEQ ID NO: 8; (i) the plant is a tomato plant, the gene or the transcript is a tomato BAX inhibitor 1 (BI-1) gene or transcript, and the polynucleotide molecule is selected from the group consisting of SEQ ID NO:37-39, and 40, or the polynucleotide comprises at least 18 contiguous nucleotides that are essentially identical or essentially complementary to SEQ ID NO: 6; (j) the plant is a lettuce plant, the gene or the transcript is a lettuce BAX inhibitor 1 (BI-1) gene or transcript, and the polynucleotide molecule is selected from the group consisting of SEQ ID NO:33-35, and 36, or the polynucleotide comprises at least 18 contiguous nucleotides that are essentially identical or essentially complementary to SEQ ID NO: 4; (k) the plant is a cucumber plant, the gene or the transcript is a cucumber BAX inhibitor 1 (BI-1) gene or transcript, and the polynucleotide molecule is selected from the group consisting of SEQ ID NO:81-88, and 142-146, or the polynucleotide comprises at least 18 contiguous nucleotides that are essentially identical or essentially complementary to SEQ ID NO: 28 or 30; or (l) the plant is a cotton plant, the gene or the transcript is a cotton BAX inhibitor 1 (BI-1) gene or transcript, and the polynucleotide molecule is selected from the group consisting of SEQ ID NO:89-91, and 92, or the polynucleotide comprises at least 18 contiguous nucleotides that are essentially identical or essentially complementary to SEQ ID NO: 32.

An additional embodiment is directed to a plant part comprising an exogenous polynucleotide that comprises at least 18 contiguous nucleotides that are essentially identical or essentially complementary to a BAX inhibitor 1 (BI-1) gene or transcript of the gene, wherein the exogenous polynucleotide is not operably linked to a promoter or to a viral vector and is not found in a non-transgenic plant; and, wherein the plant part exhibits an improvement in fungal disease resistance that results from suppression of the BAX inhibitor 1 (BI-1) gene. In certain embodiments, the plant part further comprises an organosilicone compound or a component thereof. In certain embodiments, the polynucleotide is selected from the group consisting of SEQ ID NO: 33-106, 109-140, and 142-146, or wherein the polynucleotide comprises at least 18 contiguous nucleotides that are essentially identical or essentially complementary to SEQ ID NO: 2, 4, 6, 8, 10, 12, 14, 16, 18, 20, 22, 24, 26, 28, 30, or 32. In certain embodiments: a) the plant part is a barley plant part, the gene or the transcript is a barley BAX inhibitor 1 (BI-1) gene or transcript, and the polynucleotide molecule is selected from the group consisting of SEQ ID NO: 73-76, 93-106, 109-120, and 121, and 121, or the polynucleotide comprises at least 18 contiguous nucleotides that are essentially identical or essentially complementary to SEQ ID NO:24; (b) the plant part is a rice plant part, the gene or the transcript is a rice BAX inhibitor 1 (BI-1) gene or transcript, and the polynucleotide molecule is selected from the group consisting of SEQ ID NO: 77-79, and 80, or the polynucleotide comprises at least 18 contiguous nucleotides that are essentially identical or essentially complementary to SEQ ID NO: 26; (c) the plant part is a wheat plant part, the gene or the transcript is a wheat BAX inhibitor 1 (BI-1) gene or transcript, and the polynucleotide molecule is selected from the group consisting of SEQ ID NO:61-67, and 68, or the polynucleotide comprises at least 18 contiguous nucleotides that are essentially identical or essentially complementary to a wheat gene or transcript that encodes SEQ ID NO:18 or 20; (d) the plant part is a soybean plant part, the gene or the transcript is a soybean BAX inhibitor 1 (BI-1) gene or transcript, and the polynucleotide molecule is selected from the group consisting of SEQ ID NO: 49-52, 69-72, and 122-140, or the polynucleotide comprises at least 18 contiguous nucleotides that are essentially identical or essentially complementary to SEQ ID NO: 12 or 22; (e) the plant part is a corn plant part, the gene or the transcript is a corn BAX inhibitor 1 (BI-1) gene or transcript, and the polynucleotide molecule is selected from the group consisting of SEQ ID NO:57-59, and 60, or the polynucleotide comprises at least 18 contiguous nucleotides that are essentially identical or essentially complementary to SEQ ID NO: 16; (f) the plant part is a sorghum plant part, the gene or the transcript is a sorghum BAX inhibitor 1 (BI-1) gene or transcript, and the polynucleotide molecule is selected from the group consisting of SEQ ID NO: 53-55, and 56, or the polynucleotide comprises at least 18 contiguous nucleotides that are essentially identical or essentially complementary to SEQ ID NO: 14; (g) the plant part is a pepper plant part, the gene or the transcript is a pepper BAX inhibitor 1 (BI-1) gene or transcript, and the polynucleotide molecule is selected from the group consisting of SEQ ID NO: 45-47, and 48, or the polynucleotide comprises at least 18 contiguous nucleotides that are essentially identical or essentially complementary to SEQ ID NO: 10; (h) the plant part is a grape plant part, the gene or the transcript is a grape BAX inhibitor 1 (BI-1) gene or transcript, and the polynucleotide molecule is selected from the group consisting of SEQ ID NO:41-43, and 44, or the polynucleotide comprises at least 18 contiguous nucleotides that are essentially identical or essentially complementary to SEQ ID NO: 8; (i) the plant part is a tomato plant part, the gene or the transcript is a tomato BAX inhibitor 1 (BI-1) gene or transcript, and the polynucleotide molecule is selected from the group consisting of SEQ ID NO:37-39, and 40, or the polynucleotide comprises at least 18 contiguous nucleotides that are essentially identical or essentially complementary to SEQ ID NO: 6; (j) the plant part is a lettuce plant part, the gene or the transcript is a lettuce BAX inhibitor 1 (BI-1) gene or transcript, and the polynucleotide molecule is selected from the group consisting of SEQ ID NO:33-35, and 36, or the polynucleotide comprises at least 18 contiguous nucleotides that are essentially identical or essentially complementary to SEQ ID NO: 4; (k) the plant part is a cucumber plant part, the gene or the transcript is a cucumber BAX inhibitor 1 (BI-1) gene or transcript, and the polynucleotide molecule is selected from the group consisting of SEQ ID NO:81-88, and 142-146, or the polynucleotide comprises at least 18 contiguous nucleotides that are essentially identical or essentially complementary to SEQ ID NO: 28 or 30; or (l) the plant part is a cotton plant part, the gene or the transcript is a cotton BAX inhibitor 1 (BI-1) gene or transcript, and the polynucleotide molecule is selected from the group consisting of SEQ ID NO:89-91, and 92, or the polynucleotide comprises at least 18 contiguous nucleotides that are essentially identical or essentially complementary to SEQ ID NO: 32. In certain embodiments, the plant part is a flower, meristem, ovule, stem, tuber, fruit, anther, pollen, leaf, root, or seed. In certain embodiments, the plant part is a seed. Also provided are processed plant products obtained from the plant parts that exhibit an improved attribute relative to a processed plant product of an untreated control plant and wherein the improved attribute results from the improved disease tolerance. In certain embodiments, the processed product is a meal, a pulp, a feed, or a food product.

Another embodiment is directed to a plant that exhibits an improvement in fungal disease resistance, wherein the plant was topically treated with a composition that comprises: a. at least one polynucleotide that comprises at least 18 contiguous nucleotides that are essentially identical or essentially complementary to a BAX inhibitor 1 (BI-1) gene or to a transcript of the gene; and, b. a transfer agent; and, wherein the plant exhibits an improvement in fungal disease resistance that results from suppression of the BAX inhibitor 1 (BI-1) gene. In certain embodiments, the transfer agent is an organosilicone preparation.

Certain embodiments are directed to a method for providing a seed that produces a plant exhibiting an improvement in fungal disease resistance comprising: a) soaking the seed in a liquid composition that comprises at least one polynucleotide that comprises at least 18 contiguous nucleotides that are essentially identical or essentially complementary to a BAX inhibitor 1 (BI-1) gene or to a transcript of the gene, wherein the seed produces a plant exhibiting an improvement in fungal disease resistance that results from suppression of the BAX inhibitor 1 (BI-1) gene. In some embodiments, the liquid composition further comprises a transfer agent. In certain embodiments, the polynucleotide comprises sense ssDNA, sense ssRNA, dsRNA, dsDNA, a double stranded DNA/RNA hybrid, anti-sense ssDNA, or anti-sense ssRNA. In certain embodiments, the polynucleotide is selected from the group consisting of SEQ ID NO: 33-106, 109-140, and 142-146, or wherein the polynucleotide comprises at least 18 contiguous nucleotides that are essentially identical or essentially complementary to SEQ ID NO: 2, 4, 6, 8, 10, 12, 14, 16, 18, 20, 22, 24, 26, 28, 30, or 32. In certain embodiments of the methods: (a) the seed is a barley seed, the gene or the transcript is a barley BAX inhibitor 1 (BI-1) gene or transcript, and the polynucleotide molecule is selected from the group consisting of SEQ ID NO: 73-76, 93-106, 109-120, and 121, and 121, or the polynucleotide comprises at least 18 contiguous nucleotides that are essentially identical or essentially complementary to SEQ ID NO:24; (b) the seed is a rice seed, the gene or the transcript is a rice BAX inhibitor 1 (BI-1) gene or transcript, and the polynucleotide molecule is selected from the group consisting of SEQ ID NO: 77-79, and 80, or the polynucleotide comprises at least 18 contiguous nucleotides that are essentially identical or essentially complementary to SEQ ID NO: 26; (c) the seed is a wheat seed, the gene or the transcript is a wheat BAX inhibitor 1 (BI-1) gene or transcript, and the polynucleotide molecule is selected from the group consisting of SEQ ID NO:61-67, and 68, or the polynucleotide comprises at least 18 contiguous nucleotides that are essentially identical or essentially complementary to a wheat gene or transcript that encodes SEQ ID NO:18 or 20; (d) the seed is a soybean seed, the gene or the transcript is a soybean BAX inhibitor 1 (BI-1) gene or transcript, and the polynucleotide molecule is selected from the group consisting of SEQ ID NO: 49-52, 69-72, and 122-140, or the polynucleotide comprises at least 18 contiguous nucleotides that are essentially identical or essentially complementary to SEQ ID NO: 12 or 22; (e) the seed is a corn seed, the gene or the transcript is a corn BAX inhibitor 1 (BI-1) gene or transcript, and the polynucleotide molecule is selected from the group consisting of SEQ ID NO:57-59, and 60, or the polynucleotide comprises at least 18 contiguous nucleotides that are essentially identical or essentially complementary to SEQ ID NO: 16; (f) the seed is a sorghum seed, the gene or the transcript is a sorghum BAX inhibitor 1 (BI-1) gene or transcript, and the polynucleotide molecule is selected from the group consisting of SEQ ID NO: 53-55, and 56, or the polynucleotide comprises at least 18 contiguous nucleotides that are essentially identical or essentially complementary to SEQ ID NO: 14; (g) the seed is a pepper seed, the gene or the transcript is a pepper BAX inhibitor 1 (BI-1) gene or transcript, and the polynucleotide molecule is selected from the group consisting of SEQ ID NO: 45-47, and 48, or the polynucleotide comprises at least 18 contiguous nucleotides that are essentially identical or essentially complementary to SEQ ID NO: 10; (h) the seed is a grape seed, the gene or the transcript is a grape BAX inhibitor 1 (BI-1) gene or transcript, and the polynucleotide molecule is selected from the group consisting of SEQ ID NO:41-43, and 44, or the polynucleotide comprises at least 18 contiguous nucleotides that are essentially identical or essentially complementary to SEQ ID NO: 8; (i) the seed is a tomato seed, the gene or the transcript is a tomato BAX inhibitor 1 (BI-1) gene or transcript, and the polynucleotide molecule is selected from the group consisting of SEQ ID NO:37-39, and 40, or the polynucleotide comprises at least 18 contiguous nucleotides that are essentially identical or essentially complementary to SEQ ID NO: 6; (j) the seed is a lettuce seed, the gene or the transcript is a lettuce BAX inhibitor 1 (BI-1) gene or transcript, and the polynucleotide molecule is selected from the group consisting of SEQ ID NO:33-35, and 36, or the polynucleotide comprises at least 18 contiguous nucleotides that are essentially identical or essentially complementary to SEQ ID NO: 4; (k) the seed is a cucumber seed, the gene or the transcript is a cucumber BAX inhibitor 1 (BI-1) gene or transcript, and the polynucleotide molecule is selected from the group consisting of SEQ ID NO:81-88, and 142-146, or the polynucleotide comprises at least 18 contiguous nucleotides that are essentially identical or essentially complementary to SEQ ID NO: 28 or 30; or (l) the seed is a cotton seed, the gene or the transcript is a cotton BAX inhibitor 1 (BI-1) gene or transcript, and the polynucleotide molecule is selected from the group consisting of SEQ ID NO:89-91, and 92, or the polynucleotide comprises at least 18 contiguous nucleotides that are essentially identical or essentially complementary to SEQ ID NO: 32. In certain embodiments, the liquid composition comprises any combination of two or more polynucleotide molecules. In certain embodiments, the polynucleotide is at least 18 to about 24, about 25 to about 50, about 51 to about 100, about 101 to about 300, about 301 to about 500, or at least about 500 or more residues in length. In certain embodiments of the methods, the composition further comprises an insecticide, a fungicide, a nematocide, or a combination thereof. In certain embodiments, the transfer agent comprises an organosilicone preparation. In certain embodiments, the polynucleotide is not operably linked to a viral vector. In certain embodiments, the polynucleotide is not integrated into the plant chromosome.

Further embodiments are directed to: a plant grown from a seed treated according to the above-described methods; progeny of the plant that exhibit fungal disease resistance; seed of the plant, wherein seed from the plant exhibits fungal disease resistance; and a processed product of the plant, the progeny plant, or the seed, wherein the processed product exhibits fungal disease resistance. In certain embodiments, the processed product exhibits an improved attribute relative to a processed product of an untreated control plant and the improved attribute results from the improved fungal disease resistance. An improved attribute of a processed product can include, but is not limited to, decreased mycotoxin content, improved nutritional content, improved storage characteristics, improved flavor, improved consistency, and the like when compared to a processed product obtained from an untreated plant or plant part.

Also provided herein are transgenic plants, plant parts, plant cells, and processed plant products containing a transgene comprising a heterologous promoter that is operably linked to a polynucleotide that comprises at least 18 contiguous nucleotides that are essentially identical or essentially complementary to a BI-1 gene or transcript of the BI-1 gene. Such transgenes can be integrated into the genome of the transgenic plant or provided in recombinant viral genomes that can be propagated in the plant. In certain embodiments, the transgene confers an improvement in fungal disease resistance and/or nematode resistance to the transgenic plants or plant parts that contain the transgene. In certain embodiments, the polynucleotide comprises at least 18 contiguous nucleotides that are essentially identical or essentially complementary to a polynucleotide selected from the group consisting of SEQ ID NO: 33-106, 109-140, and 142-146 or comprises at least 18 contiguous nucleotides that are essentially identical or essentially complementary to a BI-1 gene or to a transcript of the gene of SEQ ID NO:2, 4, 6, 8, 10, 12, 14, 16, 18, 20, 22, 24, 26, 28, 30, or 32. In certain embodiments: (a) the plant is a barley plant, the gene or the transcript is a barley BAX inhibitor 1 (BI-1) gene or transcript, and the polynucleotide molecule is selected from the group consisting of SEQ ID NO: 73-76, 93-106, 109-120, and 121, and 121, or the polynucleotide comprises at least 18 contiguous nucleotides that are essentially identical or essentially complementary to SEQ ID NO:24; (b) the plant is a rice plant, the gene or the transcript is a rice BAX inhibitor 1 (BI-1) gene or transcript, and the polynucleotide molecule is selected from the group consisting of SEQ ID NO: 77-79, and 80, or the polynucleotide comprises at least 18 contiguous nucleotides that are essentially identical or essentially complementary to SEQ ID NO: 26; (c) the plant is a wheat plant, the gene or the transcript is a wheat BAX inhibitor 1 (BI-1) gene or transcript, and the polynucleotide molecule is selected from the group consisting of SEQ ID NO:61-67, and 68, or the polynucleotide comprises at least 18 contiguous nucleotides that are essentially identical or essentially complementary to a wheat gene or transcript that encodes SEQ ID NO:18 or 20; (d) the plant is a soybean plant, the gene or the transcript is a soybean BAX inhibitor 1 (BI-1) gene or transcript, and the polynucleotide molecule is selected from the group consisting of SEQ ID NO: 49-52, 69-72, and 122-140, or the polynucleotide comprises at least 18 contiguous nucleotides that are essentially identical or essentially complementary to SEQ ID NO: 12 or 22; (e) the plant is a corn plant, the gene or the transcript is a corn BAX inhibitor 1 (BI-1) gene or transcript, and the polynucleotide molecule is selected from the group consisting of SEQ ID NO:57-59, and 60, or the polynucleotide comprises at least 18 contiguous nucleotides that are essentially identical or essentially complementary to SEQ ID NO: 16; (f) the plant is a sorghum plant, the gene or the transcript is a sorghum BAX inhibitor 1 (BI-1) gene or transcript, and the polynucleotide molecule is selected from the group consisting of SEQ ID NO: 53-55, and 56, or the polynucleotide comprises at least 18 contiguous nucleotides that are essentially identical or essentially complementary to SEQ ID NO: 14; (g) the plant is a pepper plant, the gene or the transcript is a pepper BAX inhibitor 1 (BI-1) gene or transcript, and the polynucleotide molecule is selected from the group consisting of SEQ ID NO: 45-47, and 48, or the polynucleotide comprises at least 18 contiguous nucleotides that are essentially identical or essentially complementary to SEQ ID NO: 10; (h) the plant is a grape plant, the gene or the transcript is a grape BAX inhibitor 1 (BI-1) gene or transcript, and the polynucleotide molecule is selected from the group consisting of SEQ ID NO:41-43, and 44, or the polynucleotide comprises at least 18 contiguous nucleotides that are essentially identical or essentially complementary to SEQ ID NO: 8; (i) the plant is a tomato plant, the gene or the transcript is a tomato BAX inhibitor 1 (BI-1) gene or transcript, and the polynucleotide molecule is selected from the group consisting of SEQ ID NO:37-39, and 40, or the polynucleotide comprises at least 18 contiguous nucleotides that are essentially identical or essentially complementary to SEQ ID NO: 6; (j) the plant is a lettuce plant, the gene or the transcript is a lettuce BAX inhibitor 1 (BI-1) gene or transcript, and the polynucleotide molecule is selected from the group consisting of SEQ ID NO:33-35, and 36, or the polynucleotide comprises at least 18 contiguous nucleotides that are essentially identical or essentially complementary to SEQ ID NO: 4; (k) the plant is a cucumber plant, the gene or the transcript is a cucumber BAX inhibitor 1 (BI-1) gene or transcript, and the polynucleotide molecule is selected from the group consisting of SEQ ID NO:81-88, and 142-146, or the polynucleotide comprises at least 18 contiguous nucleotides that are essentially identical or essentially complementary to SEQ ID NO: 28 or 30; or (l) the plant is a cotton plant, the gene or the transcript is a cotton BAX inhibitor 1 (BI-1) gene or transcript, and the polynucleotide molecule is selected from the group consisting of SEQ ID NO:89-91, and 92, or the polynucleotide comprises at least 18 contiguous nucleotides that are essentially identical or essentially complementary to SEQ ID NO: 32. In certain embodiments, the transgenic plant part is a flower, meristem, ovule, stem, tuber, fruit, anther, pollen, leaf, root, or seed. Processed plant products containing the transgene include, but are not limited to, a meal a pulp, a feed, or a food product obtainable from the transgenic plant parts. In certain embodiments, the processed plant products exhibit an improved attribute relative to a processed plant product of an untreated control plant and wherein the improved attribute results from the improved fungal disease resistance and/or nematode resistance conferred by the transgene. In certain embodiments, the processed product is a meal, a pulp, a feed, or a food product. Also provided herein are methods for obtaining transgenic plants exhibiting an improvement in fungal disease resistance and/or nematode resistance comprising the steps of introducing any of the aforementioned transgenes into the genome of a plant and selecting for a transgenic plant wherein expression of an endogenous BAX inhibitor 1 (BI-1) gene is suppressed, thereby obtaining a plant exhibiting an improvement in fungal disease resistance and/or nematode resistance. Also provided herein are methods for improving fungal disease resistance and/or nematode resistance in plants that comprise growing transgenic plants comprising any of the aforementioned transgenes wherein expression of an endogenous BI-1 gene is suppressed in the presence of fungi and/or nematodes, wherein fungal disease resistance and/or nematode resistance of the transgenic plants is improved in comparison to a control plant that lack a transgene that suppresses an endogenous BI-1 gene in the control plant.

BRIEF DESCRIPTION OF THE DRAWINGS

FIG. 1. Panel A. shows a graph of cyst counts for Soy Cyst Nematode (SCN) disease measurement at twenty eight days after treatment and inoculation with SCN. Panel B. shows a graph of gall weights.

DETAILED DESCRIPTION

I. Definitions

Figure 2:
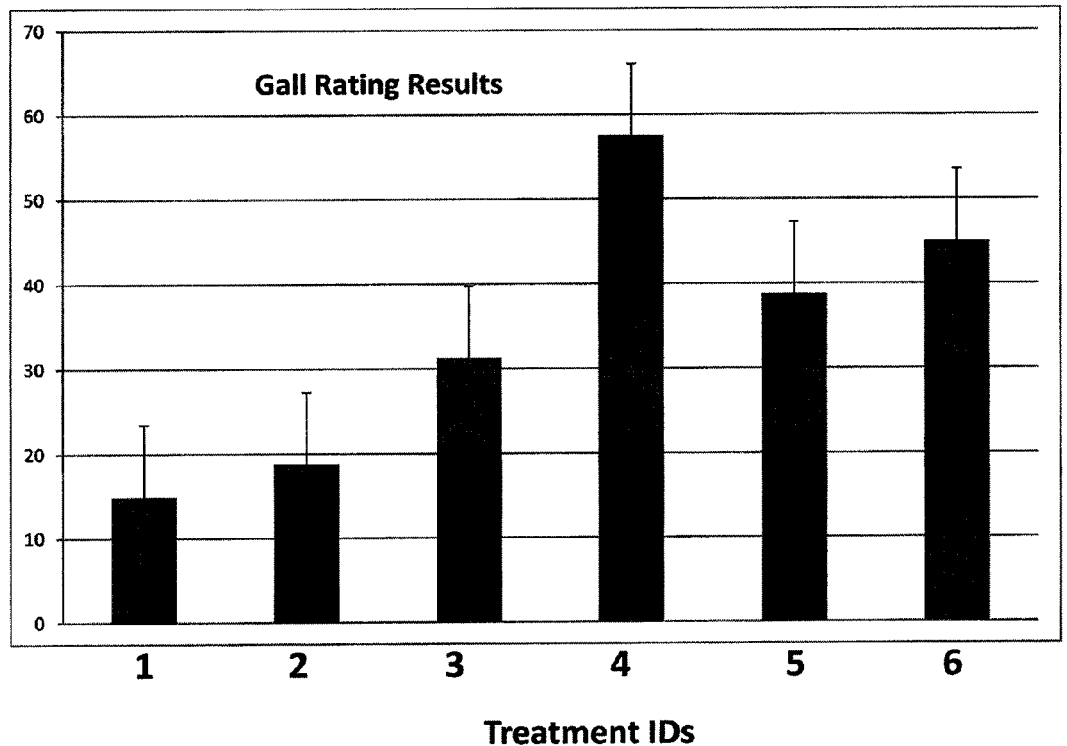
FIG. 2. presents the gall rating results for Root Knot Nematode (RKN) disease measured as % root mass galled for dsRNA treatments (or controls) followed by inoculation with vermiform eggs.

The following definitions and methods are provided to better define the present embodiments and to guide those of ordinary skill in the art in the practice of the present embodiments. Unless otherwise noted, terms are to be understood according to conventional usage by those of ordinary skill in the relevant art.

Where a term is provided in the singular, the inventors also contemplate aspects described by the plural of that term.

As used herein, the terms "DNA," "DNA molecule," and "DNA polynucleotide molecule" refer to a single-stranded DNA or double-stranded DNA molecule of genomic or synthetic origin, such as, a polymer of deoxyribonucleotide bases or a DNA polynucleotide molecule.

As used herein, the terms "DNA sequence," "DNA nucleotide sequence," and "DNA polynucleotide sequence" refer to the nucleotide sequence of a DNA molecule.

As used herein, the term "gene" refers to any portion of a nucleic acid that provides for expression of a transcript or encodes a transcript. A "gene" thus includes, but is not limited to, a promoter region, 5' untranslated regions, transcript encoding regions that can include intronic regions, and 3' untranslated regions.

As used herein, the terms "RNA," "RNA molecule," and "RNA polynucleotide molecule" refer to a single-stranded RNA or double-stranded RNA molecule of genomic or synthetic origin, such as, a polymer of ribonucleotide bases that comprise single or double stranded regions.

Unless otherwise stated, nucleotide sequences in the text of this specification are given, when read from left to right, in the 5' to 3' direction. The nomenclature used herein is that required by Title 37 of the United States Code of Federal Regulations § 1.822 and set forth in the tables in WIPO Standard ST.25 (1998), Appendix 2, Tables 1 and 3.

As used herein, a "plant surface" refers to any exterior portion of a plant. Plant surfaces thus include, but are not limited to, the surfaces of flowers, stems, tubers, fruit, anthers, pollen, leaves, roots, or seeds. A plant surface can be on a portion of a plant that is attached to other portions of a plant or on a portion of a plant that is detached from the plant.

As used herein, the phrase "polynucleotide is not operably linked to a promoter" refers to a polynucleotide that is not covalently linked to a polynucleotide promoter sequence that is specifically recognized by either a DNA dependent RNA polymerase II protein or by a viral RNA dependent RNA polymerase in such a manner that the polynucleotide will be transcribed by the DNA dependent RNA polymerase II protein or viral RNA dependent RNA polymerase. A polynucleotide that is not operably linked to a promoter can be transcribed by a plant RNA dependent RNA polymerase.

As used herein, SEQ ID NO:, though displayed in the Sequence Listing in the form of ssDNA or ssRNA, encompass dsDNA equivalents, dsRNA equivalents, ssRNA as shown or equivalents, ssRNA complements, ssDNA as shown or equivalents, and ssDNA complements.

As used herein, a first nucleic-acid sequence is "operably" connected or "linked" with a second nucleic acid sequence when the first nucleic acid sequence is placed in a functional relationship with the second nucleic acid sequence. For instance, a promoter is operably linked to an RNA and/or protein-coding sequence if the promoter provides for transcription or expression of the RNA or coding sequence. Generally, operably linked DNA sequences are contiguous and, where necessary to join two protein-coding regions, are in the same reading frame.

As used herein, the phrase "organosilicone preparation" refers to a liquid comprising one or more organosilicone compounds, wherein the liquid or components contained therein, when combined with a polynucleotide in a composition that is topically applied to a target plant surface, enable the polynucleotide to enter a plant cell. Examples of organosilicone preparations include, but are not limited to, preparations marketed under the trade names "Silwet®" or "BREAK-THRU®" and preparations provided in Table 1. In certain embodiments, an organosilicone preparation can enable a polynucleotide to enter a plant cell in a manner permitting a polynucleotide suppression of target gene expression in the plant cell.

As used herein, the phrase "provides for an improvement in fungal disease resistance" refers to any measurable increase in a plants resistance to fungal damage. In certain embodiments, an improvement in fungal disease resistance in a plant or plant part can be determined in a comparison to a control plant or plant part that has not been treated with a composition comprising a polynucleotide and a transfer agent. When used in this context, a control plant is a plant that has not undergone treatment with polynucleotide and a transfer agent. Such control plants would include, but are not limited to, untreated plants or mock treated plants.

As used herein, the phrase "provides for a reduction", when used in the context of a transcript or a protein in a plant or plant part, refers to any measurable decrease in the level of transcript or protein in a plant or plant part. In certain embodiments, a reduction of the level of a transcript in a plant or plant part can be determined in a comparison to a control plant or plant part that has not been treated with a composition comprising a polynucleotide and a transfer agent. When used in this context, a control plant or plant part is a plant or plant part that has not undergone treatment with polynucleotide and a transfer agent. Such control plants or plant parts would include, but are not limited to, untreated or mock treated plants and plant parts.

As used herein, the phrase "wherein said plant does not comprise a transgene" refers to a plant that lacks either a DNA molecule comprising a promoter that is operably linked to a polynucleotide or a recombinant viral vector.

As used herein, the phrase "suppressing expression" or "suppression", when used in the context of a gene, refers any measurable decrease in the amount and/or activity of a product encoded by the gene. Thus, expression of a gene can be suppressed when there is a reduction in levels of a transcript from the gene, a reduction in levels of a protein encoded by the gene, a reduction in the activity of the transcript from the gene, a reduction in the activity of a protein encoded by the gene, any one of the preceding conditions, or any combination of the preceding conditions. In this context, the activity of a transcript includes, but is not limited to, its ability to be translated into a protein and/or to exert any RNA-mediated biologic or biochemical effect. In this context, the activity of a protein includes, but is not limited to, its ability to exert any protein-mediated biologic or biochemical effect. In certain embodiments, a suppression of gene expression in a plant or plant part can be determined in a comparison of gene product levels or activities in a treated plant to a control plant or plant part that has not been treated with a composition comprising a polynucleotide and a transfer agent. When used in this context, a control plant or plant part is a plant or plant part that has not undergone treatment with polynucleotide and a transfer agent. Such control plants or plant parts would include, but are not limited to, untreated or mock treated plants and plant parts.

As used herein, the term "transcript" corresponds to any RNA that is produced from a gene by the process of transcription. A transcript of a gene can thus comprise a primary transcription product which can contain introns or can comprise a mature RNA that lacks introns.

As used herein, the term "liquid" refers to both homogeneous mixtures such as solutions and non-homogeneous mixtures such as suspensions, colloids, micelles, and emulsions.

II. Overview

The hypersensitive reaction (HR) in plants is a form of programmed cell death involved in many developmental processes and stress responses including disease resistance to pathogens.

The protein BAX inhibitor 1 (BI-1), localized at the endoplasmic reticulum and the nuclear envelope in both plants and animals, is a negative regulator of programmed cell death. The silencing of BAX inhibitor 1 increases the resistance of barley to powdery mildew infection.

Provided herein are certain methods and polynucleotide compositions that can be applied to living plant cells/tissues to suppress expression of target genes and that provide improved fungal disease resistance to a crop plant. Also provided herein are plants and plant parts exhibiting fungal disease resistance as well as processed products of such plants or plant parts. The compositions may be topically applied to the surface of a plant, such as to the surface of a leaf, and include a transfer agent. Aspects of the method can be applied to various crops, for example, including but not limited to: i) row crop plants including, but are not limited to, corn, barley, sorghum, soybean, cotton, canola, sugar beet, alfalfa, sugarcane, rice, and wheat; ii) vegetable plants including, but not limited to, tomato, potato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra; iii) culinary plants including, but not limited to, basil, parsley, coffee, or tea; iv) fruit plants including but not limited to apple, pear, cherry, peach, plum, apricot, banana, plantain, table grape, wine grape, citrus, avocado, mango, or berry; v) a tree grown for ornamental or commercial use, including, but not limited to, a fruit or nut tree; or, vi) an ornamental plant (e. g., an ornamental flowering plant or shrub or turf grass). The methods and compositions provided herein can also be applied to plants produced by a cutting, cloning, or grafting process (i. e., a plant not grown from a seed) that include fruit trees and plants. Fruit trees produced by such processes include, but are not limited to, citrus and apple trees. Plants produced by such processes include, but are not limited to, avocados, tomatoes, eggplant, cucumber, melons, watermelons, and grapes as well as various ornamental plants.

Without being bound by theory, the compositions and methods of the present embodiments are believed to operate through one or more of the several natural cellular pathways involved in RNA-mediated gene suppression as generally described in Brodersen and Voinnet (2006), *Trends Genetics*, 22:268-280; Tomari and Zamore (2005) *Genes & Dev.*, 19:517-529; Vaucheret (2006) *Genes Dev.*, 20:759-771; Meins et al. (2005) *Annu. Rev. Cell Dev. Biol.*, 21:297-318; and Jones-Rhoades et al. (2006) *Annu. Rev. Plant Biol.*, 57:19-53. RNA-mediated gene suppression generally involves a double-stranded RNA (dsRNA) intermediate that is formed intra-molecularly within a single RNA molecule or inter-molecularly between two RNA molecules. This longer dsRNA intermediate is processed by a ribonuclease of the RNAase III family (Dicer or Dicer-like ribonuclease) to one or more shorter double-stranded RNAs, one strand of which is incorporated into the RNA-induced silencing complex ("RISC"). For example, the siRNA pathway involves the cleavage of a longer double-stranded RNA intermediate to small interfering RNAs ("siRNAs"). The size of siRNAs is believed to range from about 19 to about 25 base pairs, but the most common classes of siRNAs in plants include those containing 21 to 24 base pairs (See, Hamilton et al. (2002) *EMBO J.*, 21:4671-4679).

Polynucleotides

As used herein, "polynucleotide" refers to a DNA or RNA molecule containing multiple nucleotides and generally refers both to "oligonucleotides" (a polynucleotide molecule of 18-25 nucleotides in length) and longer polynucleotides of 26 or more nucleotides. Embodiments include compositions including oligonucleotides having a length of 18-25 nucleotides (18-mers, 19-mers, 20-mers, 21-mers, 22-mers, 23-mers, 24-mers, or 25-mers), or medium-length polynucleotides having a length of 26 or more nucleotides (polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e. g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene). Where a polynucleotide is double-stranded, its length can be similarly described in terms of base pairs.

Polynucleotide compositions used in the various embodiments include compositions including oligonucleotides, polynucleotides, or a mixture of both, including: RNA or DNA or RNA/DNA hybrids or chemically modified oligonucleotides or polynucleotides or a mixture thereof. In certain embodiments, the polynucleotide may be a combination of ribonucleotides and deoxyribonucleotides, for example, synthetic polynucleotides consisting mainly of ribonucleotides but with one or more terminal deoxyribonucleotides or synthetic polynucleotides consisting mainly of deoxyribonucleotides but with one or more terminal dideoxyribonucleotides. In certain embodiments, the polynucleotide includes non-canonical nucleotides such as inosine, thiouridine, or pseudouridine. In certain embodiments, the polynucleotide includes chemically modified nucleotides. Examples of chemically modified oligonucleotides or polynucleotides are well known in the art; see, for example, U.S. Patent Publication 2011/0171287, U.S. Patent Publication 2011/0171176, U.S. Patent Publication 2011/0152353, U.S. Patent Publication 2011/0152346, and U.S. Patent Publication 2011/0160082, which are herein incorporated by reference. Illustrative examples include, but are not limited to, the naturally occurring phosphodiester backbone of an oligonucleotide or polynucleotide which can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labeled with a fluorescent moiety (e. g., fluorescein or rhodamine) or other label (e. g., biotin).

Polynucleotides can be single- or double-stranded RNA, single- or double-stranded DNA, double-stranded DNA/RNA hybrids, and modified analogues thereof. In certain embodiments, the polynucleotides that provide single-stranded RNA in the plant cell may be: (a) a single-stranded RNA molecule (ssRNA), (b) a single-stranded RNA molecule that self-hybridizes to form a double-stranded RNA molecule, (c) a double-stranded RNA molecule (dsRNA), (d) a single-stranded DNA molecule (ssDNA), (e) a single-stranded DNA molecule that self-hybridizes to form a double-stranded DNA molecule, (f) a single-stranded DNA molecule including a modified Pol III gene that is transcribed to an RNA molecule, (g) a double-stranded DNA molecule (dsDNA), (h) a double-stranded DNA molecule including a modified Pol III gene that is transcribed to an RNA molecule, and (i) a double-stranded, hybridized RNA/DNA molecule, or combinations thereof. In certain embodiments, these polynucleotides can comprise both ribonucleic acid residues and deoxyribonucleic acid residues. In certain embodiments, these polynucleotides include chemically modified nucleotides or non-canonical nucleotides. In certain embodiments of the methods, the polynucleotides include double-stranded DNA formed by intramolecular hybridization, double-stranded DNA formed by intermolecular hybridization, double-stranded RNA formed by intramolecular hybridization, or double-stranded RNA formed by intermolecular hybridization. In certain embodiments where the polynucleotide is a dsRNA, the anti-sense strand will comprise at least 18 nucleotides that are essentially complementary to the target gene. In certain embodiments the polynucleotides include single-stranded DNA or single-stranded RNA that self-hybridizes to form a hairpin structure having an at least partially double-stranded structure including at least one segment that will hybridize to RNA transcribed from the gene targeted for suppression. Not intending to be bound by any mechanism, it is believed that such polynucleotides are or will produce single-stranded RNA with at least one segment that will hybridize to RNA transcribed from the gene targeted for suppression. In certain embodiments, the polynucleotides can be operably linked to a promoter—generally a promoter functional in a plant, for example, a pol II promoter, a pol III promoter, a pol IV promoter, or a pol V promoter.

The polynucleotide molecules of the present embodiments are designed to modulate expression by inducing regulation or suppression of an endogenous gene in a plant and are designed to have a nucleotide sequence essentially identical or essentially complementary to the nucleotide sequence of an endogenous gene of a plant or to the sequence of RNA transcribed from an endogenous gene of a plant, which can be coding sequence or non-coding sequence. These effective polynucleotide molecules that modulate expression are referred to herein as "a trigger, or triggers". By "essentially identical" or "essentially complementary" it is meant that the trigger polynucleotides (or at least one strand of a double-stranded polynucleotide) have sufficient identity or complementarity to the endogenous gene or to the RNA transcribed from the endogenous gene (e.g. the transcript) to suppress expression of the endogenous gene (e.g. to effect a reduction in levels or activity of the gene transcript and/or encoded protein). Polynucleotides of the methods and compositions provided herein need not have 100 percent identity to a complementarity to the endogenous gene or to the RNA transcribed from the endogenous gene (i.e. the transcript) to suppress expression of the endogenous gene (i.e. to effect a reduction in levels or activity of the gene transcript or encoded protein). Thus, in certain embodiments, the polynucleotide or a portion thereof is designed to be essentially identical to, or essentially complementary to, a sequence of at least 18 or 19 contiguous nucleotides in either the target gene or messenger RNA transcribed from the target gene (e.g. the transcript). In certain embodiments, an "essentially identical" polynucleotide has 100 percent sequence identity or at least about 83, 84, 85, 86, 87, 88, 89, 90, 91, 92, 93, 94, 95, 96, 97, 98, or 99 percent sequence identity when compared to the sequence of 18 or more contiguous nucleotides in either the endogenous target gene or to an RNA transcribed from the target gene (e.g. the transcript). In certain embodiments, an "essentially complementary" polynucleotide has 100 percent sequence complementarity or at least about 83, 84, 85, 86, 87, 88, 89, 90, 91, 92, 93, 94, 95, 96, 97, 98, or 99 percent sequence complementarity when compared to the sequence of 18 or more contiguous nucleotides in either the target gene or RNA transcribed from the target gene.

In certain embodiments, polynucleotides used in the methods and compositions provided herein can be essentially identical or essentially complementary to any of: i) conserved regions of BAX inhibitor 1 (BI-1) genes of both monocot and dicot plants; ii) conserved regions of BAX inhibitor 1 (BI-1) genes of monocot plants; or iii) conserved regions of BAX inhibitor 1 (BI-1) genes of dicot plants. Such polynucleotides that are essentially identical or essentially complementary to such conserved regions can be used to improve fungal disease resistance by suppressing expression of BAX inhibitor 1 (BI-1) genes in any of: i) both dicot and monocot plants, including, but not limited to, corn, barley, wheat, sorghum, rice, cucumber, pea, *Medicago* sp., soybean, pepper, tomato, and grape; ii) monocot plants, including, but not limited to, corn, barley, wheat, sorghum, switchgrass, and rice, and; or iii) dicot plants, including, but not limited to, cucumber, pea, *Medicago* sp., soybean, pepper, tomato, and grape. Conserved regions of dicot and monocot plant BAX inhibitor 1 (BI-1) genes of SEQ ID NO: 2, 4, 6, 7, 8, 10, 12, 14, 16, 18, 20, 22, 24, 26, 28, 30, and 32 can be targeted by essentially identical or essentially complementary polynucleotides.

Polynucleotides containing mismatches to the target gene or transcript can thus be used in certain embodiments of the compositions and methods provided herein. In certain embodiments, a polynucleotide can comprise at least 19 contiguous nucleotides that are essentially identical or essentially complementary to said gene or said transcript or comprises at least 19 contiguous nucleotides that are essentially identical or essentially complementary to the target gene or target gene transcript. In certain embodiments, a polynucleotide of 19 continuous nucleotides that is essentially identical or essentially complementary to the endogenous target gene or to an RNA transcribed from the target gene (e.g. the transcript) can have 1 or 2 mismatches to the target gene or transcript. In certain embodiments, a polynucleotide of 20 or more nucleotides that contains a contiguous 19 nucleotide span of identity or complementarity to the endogenous target gene or to an RNA transcribed from the target gene can have 1 or 2 mismatches to the target gene or transcript. In certain embodiments, a polynucleotide of 21 continuous nucleotides that is essentially identical or essentially complementary to the endogenous target gene or to an RNA transcribed from the target gene (e.g. the transcript) can have 1, 2, or 3 mismatches to the target gene or transcript. In certain embodiments, a polynucleotide of 22 or more nucleotides that contains a contiguous 21 nucleotide span of identity or complementarity to the endogenous target gene or to an RNA transcribed from the target gene can have 1, 2, or 3 mismatches to the target gene or transcript. In designing polynucleotides with mismatches to an endogenous target gene or to an RNA transcribed from the target gene, mismatches of certain types and at certain positions that are more likely to be tolerated can be used. In certain embodiments, mismatches formed between adenine and cytosine or guanosine and uracil residues are used as described by Du et al. Nucleic Acids Research, 2005, Vol. 33, No. 5 1671-1677. In certain embodiments, mismatches in 19 base pair overlap regions can be at the low tolerance positions 5, 7, 8 or 11 (from the 5' end of a 19 nucleotide target) with well tolerated nucleotide mismatch residues, at medium tolerance positions 3, 4, and 12-17, and/or at the high tolerance nucleotide positions at either end of the region of complementarity (i.e. positions 1, 2, 18, and 19) as described by Du et al. Nucleic Acids Research, 2005, Vol. 33, No. 5 1671-1677. It is further anticipated that tolerated mismatches can be empirically determined in assays where the polynucleotide is applied to the plants via the methods provided herein and the treated plants assayed for suppression of BAX inhibitor 1 (BI-1) expression or appearance of fungal disease resistance.

In certain embodiments, polynucleotide molecules are designed to have 100 percent sequence identity with or complementarity to one allele or one family member of a given target gene coding or non-coding sequence of a BI-1 target gene. In other embodiments, the polynucleotide molecules are designed to have 100 percent sequence identity with or complementarity to multiple alleles or family members of a given BAX inhibitor 1 (BI-1) target gene. In certain embodiments, the polynucleotide can thus comprise at least 18 contiguous nucleotides that are identical or complementary to SEQ ID NO: 33-106, 108-140, or 142-146. In certain embodiments, the polynucleotide comprises at least 18 contiguous nucleotides that are essentially identical or essentially complementary to SEQ ID NO: 2, 4, 6, 8, 10, 12, 14, 16, 18, 20, 22, 24, 26, 28, 30, or 32.

In certain embodiments, polynucleotide compositions and methods provided herein typically effect regulation or modulation (e. g., suppression) of gene expression during a period during the life of the treated plant of at least 1 week or longer and typically in systemic fashion. For instance, within days of treating a plant leaf with a polynucleotide composition as described herein, primary and transitive siRNAs can be detected in other leaves lateral to and above the treated leaf and in apical tissue. In certain embodiments, methods of systemically suppressing expression of a gene in a plant, the methods comprising treating said plant with a composition comprising at least one polynucleotide and a transfer agent, wherein said polynucleotide comprises at least 18 or at least 19 contiguous nucleotides that are essentially identical or essentially complementary to a gene or a transcript encoding a BAX inhibitor 1 (BI-1) gene of the plant are provided, whereby expression of the gene in said plant or progeny thereof is systemically suppressed in comparison to a control plant that has not been treated with the composition.

Compositions used to suppress a target gene can comprise one or more polynucleotides that are essentially identical or essentially complementary to multiple genes, or to multiple segments of one or more genes. In certain embodiments, compositions used to suppress a target gene can comprise one or more polynucleotides that are essentially identical or essentially complementary to multiple consecutive segments of a target gene, multiple non-consecutive segments of a target gene, multiple alleles of a target gene, or multiple target genes from one or more species.

In certain embodiments, the polynucleotide includes two or more copies of a nucleotide sequence (of 18 or more nucleotides) where the copies are arranged in tandem fashion. In another embodiment, the polynucleotide includes two or more copies of a nucleotide sequence (of 18 or more nucleotides) where the copies are arranged in inverted repeat fashion (forming an at least partially self-complementary strand). The polynucleotide can include both tandem and inverted-repeat copies. Whether arranged in tandem or inverted repeat fashion, each copy can be directly contiguous to the next, or pairs of copies can be separated by an optional spacer of one or more nucleotides. The optional spacer can be unrelated sequence (i. e., not essentially identical to or essentially complementary to the copies, nor essentially identical to, or essentially complementary to, a sequence of 18 or more contiguous nucleotides of the endogenous target gene or RNA transcribed from the endogenous target gene). Alternatively the optional spacer can include sequence that is complementary to a segment of the endogenous target gene adjacent to the segment that is targeted by the copies. In certain embodiments, the polynucleotide includes two copies of a nucleotide sequence of between about 20 to about 30 nucleotides, where the two copies are separated by a spacer no longer than the length of the nucleotide sequence.

Tiling

Polynucleotide trigger molecules can be identified by "tiling" gene targets in random length fragments, e.g. 200-300 polynucleotides in length, with partially overlapping regions, e.g. 25 or so nucleotide overlapping regions along the length of the target gene. Multiple gene target sequences can be aligned and polynucleotide sequence regions with homology in common are identified as potential trigger molecules for multiple targets. Multiple target sequences can be aligned and sequence regions with poor homology are identified as potential trigger molecules for selectively distinguishing targets. To selectively suppress a single gene, trigger sequences may be chosen from regions that are unique to the target gene either from the transcribed region or the non-coding regions, e.g., promoter regions, 3' untranslated regions, introns and the like.

Polynucleotides fragments are designed along the length of the full length coding and untranslated regions of a BI-1 gene or family member as contiguous overlapping fragments of 200-300 polynucleotides in length or fragment lengths representing a percentage of the target gene. These fragments are applied topically (as sense or anti-sense ssDNA or ssRNA, dsRNA, or dsDNA) to determine the relative effectiveness in providing the fungal disease resistance phenotype. Fragments providing the desired activity may be further subdivided into 50-60 polynucleotide fragments which are evaluated for providing the fungal disease resistance phenotype. The 50-60 base fragments with the desired activity may then be further subdivided into 19-30 base fragments which are evaluated for providing the fungal disease resistance phenotype. Once relative effectiveness is determined, the fragments are utilized singly, or in combination in one or more pools to determine effective trigger composition or mixture of trigger polynucleotides for providing the fungal disease resistance phenotype.

Coding and/or non-coding sequences of gene families in the crop of interest are aligned and 200-300 polynucleotide fragments from the least homologous regions amongst the aligned sequences are evaluated using topically applied polynucleotides (as sense or anti-sense ssDNA or ssRNA, dsRNA, or dsDNA) to determine their relative effectiveness in providing the fungal disease resistance phenotype. The effective segments are further subdivided into 50-60 polynucleotide fragments, prioritized by least homology, and reevaluated using topically applied polynucleotides. The effective 50-60 polynucleotide fragments are subdivided into 19-30 polynucleotide fragments, prioritized by least homology, and again evaluated for induction of the fungal disease resistance phenotype. Once relative effectiveness is determined, the fragments are utilized singly, or again evaluated in combination with one or more other fragments to determine the trigger composition or mixture of trigger polynucleotides for providing the fungal disease resistance phenotype.

Coding and/or non-coding sequences of gene families in the crop of interest are aligned and 200-300 polynucleotide fragments from the most homologous regions amongst the aligned sequences are evaluated using topically applied polynucleotides (as sense or anti-sense ssDNA or ssRNA, dsRNA, or dsDNA) to determine their relative effectiveness in inducing the fungal disease resistance phenotype. The effective segments are subdivided into 50-60 polynucleotide fragments, prioritized by most homology, and reevaluated using topically applied polynucleotides. The effective 50-60 polynucleotide fragments are subdivided into 19-30 polynucleotide fragments, prioritized by most homology, and again evaluated for induction of the yield/quality phenotype. Once relative effectiveness is determined, the fragments may be utilized singly, or in combination with one or more other fragments to determine the trigger composition or mixture of trigger polynucleotides for providing the fungal disease resistance phenotype.

Also, provided herein are methods for identifying a preferred polynucleotide for improving fungal disease in a plant. Populations of candidate polynucleotides that are essentially identical or essentially complementary to a BI-1 gene or transcript of the gene can be generated by a variety of approaches, including but not limited to, any of the tiling, least homology, or most homology approaches provided herein. Such populations of polynucleotides can also be generated or obtained from any of the polynucleotides or genes provided herewith in SEQ ID NO: 2, 4, 6, 8, 10, 12, 14, 16, 18, 20, 22, 24, 26, 28, 30, 32, 33-106, 108-140, or 142-146. Such populations of polynucleotides can also be generated or obtained from any genes that are orthologous to the genes or proteins provided herewith as SEQ ID NO: 1-32. Such polynucleotides can be topically applied to a surface of plants in a composition comprising at least one polynucleotide from said population and a transfer agent to obtain treated plants. Treated plants that exhibit suppression of the BI-1 gene and/or exhibit an improvement in fungal disease resistance are identified, thus identifying a preferred polynucleotide that improves fungal disease in a plant. Suppression of the gene can be determined by any assay for the levels and/or activity of a gene product (i.e. transcript or protein). Suitable assays for transcripts include, but are not limited to, semi-quantitative or quantitative reverse transcriptase PCR® (qRT-PCR) assays. Suitable assays for proteins include, but are not limited to, semi-quantitative or quantitative immunoassays, biochemical activity assays, or biological activity assays. In certain embodiments, the polynucleotides can be applied alone. In other embodiments, the polynucleotides can be applied in pools of multiple polynucleotides. When a pool of polynucleotides provides for suppression of the BI-1 gene and/or an improvement in fungal disease resistance are identified, the pool can be de-replicated and retested as necessary or desired to identify one or more preferred polynucleotide(s) that improves fungal disease resistance in a plant.

Methods of making polynucleotides are well known in the art. Such methods of making polynucleotides can include in vivo biosynthesis, in vitro enzymatic synthesis, or chemical synthesis. In certain embodiments, RNA molecules can be made by either in vivo or in vitro synthesis from DNA templates where a suitable promoter is operably linked to the polynucleotide and a suitable DNA-dependent RNA polymerase is provided. DNA-dependent RNA polymerases include, but are not limited to, *E. coli* or other bacterial RNA polymerases as well as the bacteriophage RNA polymerases such as the T7, T3, and SP6 RNA polymerases. Commercial preparation of oligonucleotides often provides two deoxyribonucleotides on the 3' end of the sense strand. Long polynucleotide molecules can be synthesized from commercially available kits, for example, kits from Applied Biosystems/Ambion (Austin, Tex.) have DNA ligated on the 5' end that encodes a bacteriophage T7 polymerase promoter that makes RNA strands that can be assembled into a dsRNA. Alternatively, dsRNA molecules can be produced from expression cassettes in bacterial cells that have regulated or deficient RNase III enzyme activity. Long polynucleotide molecules can also be assembled from multiple RNA or DNA fragments. In some embodiments design parameters such as Reynolds score (Reynolds et al. *Nature Biotechnology* 22, 326-330 (2004) and Tuschl rules (Pei and Tuschl, Nature Methods 3(9): 670-676, 2006) are known in the art and are used in selecting polynucleotide sequences effective in gene silencing. In some embodiments random design or empirical selection of polynucleotide sequences is used in selecting polynucleotide sequences effective in gene silencing. In some embodiments the sequence of a polynucleotide is screened against the genomic DNA of the intended plant to minimize unintentional silencing of other genes.

While there is no upper limit on the concentrations and dosages of polynucleotide molecules that can be useful in the methods and compositions provided herein, lower effective concentrations and dosages will generally be sought for efficiency. The concentrations can be adjusted in consideration of the volume of spray or treatment applied to plant leaves or other plant part surfaces, such as flower petals, stems, tubers, fruit, anthers, pollen, leaves, roots, or seeds. In one embodiment, a useful treatment for herbaceous plants using 25-mer polynucleotide molecules is about 1 nanomole (nmol) of polynucleotide molecules per plant, for example, from about 0.05 to 1 nmol polynucleotides per plant. Other embodiments for herbaceous plants include useful ranges of about 0.05 to about 100 nmol, or about 0.1 to about 20 nmol, or about 1 nmol to about 10 nmol of polynucleotides per plant. In certain embodiments, about 40 to about 50 nmol of a ssDNA polynucleotide are applied. In certain embodiments, about 0.5 nmol to about 2 nmol of a dsRNA is applied. In certain embodiments, a composition containing about 0.5 to about 2.0 mg/mL, or about 0.14 mg/mL of dsRNA or ssDNA (21-mer) is applied. In certain embodiments, a composition of about 0.5 to about 1.5 mg/mL of a long dsRNA polynucleotide (i.e. about 50 to about 200 or more nucleotides) is applied. In certain embodiments, about 1 nmol to about 5 nmol of a dsRNA is applied to a plant. In certain embodiments, the polynucleotide composition as topically applied to the plant contains the at least one polynucleotide at a concentration of about 0.01 to about 10 milligrams per milliliter, or about 0.05 to about 2 milligrams per milliliter, or about 0.1 to about 2 milligrams per milliliter. Very large plants, trees, or vines may require correspondingly larger amounts of polynucleotides. When using long dsRNA molecules that can be processed into multiple oligonucleotides, lower concentrations can be used. To illustrate certain embodiments, the factor 1×, when applied to oligonucleotide molecules is arbitrarily used to denote a treatment of 0.8 nmol of polynucleotide molecule per plant; 10×, 8 nmol of polynucleotide molecule per plant; and 100×, 80 nmol of polynucleotide molecule per plant.

The polynucleotide compositions of certain embodiments are useful in compositions, such as liquids that comprise polynucleotide molecules, alone or in combination with other components either in the same liquid or in separately applied liquids that provide a transfer agent. As used herein, a transfer agent is an agent that, when combined with a polynucleotide in a composition that is topically applied to a target plant surface, enables the polynucleotide to enter a plant cell. In certain embodiments, a transfer agent is an agent that conditions the surface of plant tissue, e. g., seeds, leaves, stems, roots, flowers, or fruits, to permeation by the polynucleotide molecules into plant cells. The transfer of polynucleotides into plant cells can be facilitated by the prior or contemporaneous application of a polynucleotide-transferring agent to the plant tissue. In some embodiments the transferring agent is applied subsequent to the application of the polynucleotide composition. The polynucleotide transfer agent enables a pathway for polynucleotides through cuticle wax barriers, stomata and/or cell wall or membrane barriers into plant cells. Suitable transfer agents to facilitate transfer of the polynucleotide into a plant cell include agents that increase permeability of the exterior of the plant or that increase permeability of plant cells to oligonucleotides or polynucleotides. Such agents to facilitate transfer of the composition into a plant cell include a chemical agent, or a physical agent, or combinations thereof. Chemical agents for conditioning or transfer include (a) surfactants, (b) an organic solvent or an aqueous solution or aqueous mixtures of organic solvents, (c) oxidizing agents, (d) acids, (e) bases, (f) oils, (g) enzymes, or combinations thereof. Embodiments of the method can optionally include an incubation step, a neutralization step (e.g., to neutralize an acid, base, or oxidizing agent, or to inactivate an enzyme), a rinsing step, or combinations thereof. Embodiments of agents or treatments for conditioning of a plant to permeation by polynucleotides include emulsions, reverse emulsions, liposomes, and other micellar-like compositions. Embodiments of agents or treatments for conditioning of a plant to permeation by polynucleotides include counter-ions or other molecules that are known to associate with nucleic acid molecules, e. g., inorganic ammonium ions, alkyl ammonium ions, lithium ions, polyamines such as spermine, spermidine, or putrescine, and other cations. Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e. g., plant-sourced oils, crop oils (such as those listed in the 9$^{th}$ Compendium of Herbicide Adjuvants, publicly available on the worldwide web (internet) at herbicide.adjuvants.com can be used, e. g., paraffinic oils, polyol fatty acid esters, or oils with short-chain molecules modified with amides or polyamines such as polyethyleneimine or N-pyrrolidine. Transfer agents include, but are not limited to, organosilicone preparations.

In certain embodiments, an organosilicone preparation that is commercially available as Silwet® L-77 surfactant having CAS Number 27306-78-1 and EPA Number: CAL-.REG.NO. 5905-50073-AA, and currently available from Momentive Performance Materials, Albany, N.Y. can be used to prepare a polynucleotide composition. In certain embodiments where a Silwet L-77 organosilicone preparation is used as a pre-spray treatment of plant leaves or other plant surfaces, freshly made concentrations in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation comprising Silwet L-77 in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided. In certain embodiments of the methods and compositions provided herein, a composition that comprises a polynucleotide molecule and an organosilicone preparation comprising Silwet L-77 in the range of about 0.3 to about 1 percent by weight (wt percent) or about 0.5 to about 1% by weight (wt percent) is used or provided.

In certain embodiments, any of the commercially available organosilicone preparations provided in the following Table 1 can be used as transfer agents in a polynucleotide composition. In certain embodiments where an organosilicone preparation of Table 1 is used as a pre-spray treatment of plant leaves or other surfaces, freshly made concentrations in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation of the following Table 1 in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

TABLE 1

| Name | CAS number | Manufacturer [1, 2] |
|---|---|---|
| BREAK-THRU ® S 321 | na | Evonik Industries AG |
| BREAK-THRU ® S 200 | 67674-67-3 | Evonik Industries AG |
| BREAK-THRU ® OE 441 | 68937-55-3 | Evonik Industries AG |
| BREAK-THRU ® S 278 | 27306-78-1 | Evonik Goldschmidt |
| BREAK-THRU ® S 243 | na | Evonik Industries AG |
| Silwet ® L-77 | 27306-78-1 | Momentive Performance Materials |
| Silwet ® HS 429 | na | Momentive Performance Materials |
| Silwet ® HS 312 | na | Momentive Performance Materials |
| BREAK-THRU ® S 233 | 134180-76-0 | Evonik Industries AG |
| Silwet ® HS 508 | | Momentive Performance Materials |
| Silwet ® HS 604 | | Momentive Performance Materials |

[1] Evonik Industries AG, Essen, Germany
[2] Momentive Performance Materials, Albany, New York Organosilicone preparations used in the methods and compositions provided herein can comprise one or more effective organosilicone compounds. As used herein, the phrase "effective organosilicone compound" is used to describe any organosilicone compound that is found in an organosilicone preparation that enables a polynucleotide to enter a plant cell. In certain embodiments, an effective organosilicone compound can enable a polynucleotide to enter a plant cell in a manner permitting a polynucleotide mediated suppression of a target gene expression in the plant cell. In general, effective organosilicone compounds include, but are not limited to, compounds that can comprise: i) a trisiloxane head group that is covalently linked to, ii) an alkyl linker including, but not limited to, an n-propyl linker, that is covalently linked to, iii) a poly glycol chain, that is covalently linked to, iv) a terminal group. Trisiloxane head groups of such effective organosilicone compounds include, but are not limited to, heptamethyltrisiloxane. Alkyl linkers can include, but are not limited to, an n-propyl linker. Poly glycol chains include, but are not limited to, polyethylene glycol or polypropylene glycol. Poly glycol chains can comprise a mixture that provides an average chain length "n" of about "7.5". In certain embodiments, the average chain length "n" can vary from about 5 to about 14. Terminal groups can include, but are not limited to, alkyl groups such as a methyl group. Effective organosilicone compounds are believed to include, but are not limited to, trisiloxane ethoxylate surfactants or polyalkylene oxide modified heptamethyl trisiloxane.

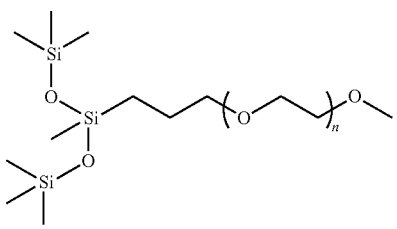

(Compound I: polyalkyleneoxide heptamethyltrisiloxane, average n=7.5).

One organosilicone compound believed to be ineffective comprises the formula:

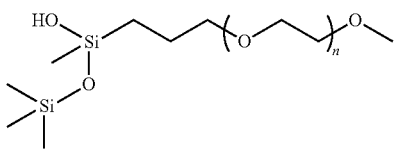

In certain embodiments, an organosilicone preparation that comprises an organosilicone compound comprising a trisiloxane head group is used in the methods and compositions provided herein. In certain embodiments, an organosilicone preparation that comprises an organosilicone compound comprising a heptamethyltrisiloxane head group is used in the methods and compositions provided herein. In certain embodiments, an organosilicone composition that comprises Compound I is used in the methods and compositions provided herein. In certain embodiments, an organosilicone composition that comprises Compound I is used in the methods and compositions provided herein. In certain embodiments of the methods and compositions provided herein, a composition that comprises a polynucleotide molecule and one or more effective organosilicone compound in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

In certain embodiments, the polynucleotide compositions that comprise an organosilicone preparation can comprise a salt such as ammonium chloride, tetrabutylphosphonium bromide, and/or ammonium sulfate. Ammonium chloride, tetrabutylphosphonium bromide, and/or ammonium sulfate can be provided in the polynucleotide composition at a concentration of about 0.5% to about 5% (w/v). An ammonium chloride, tetrabutylphosphonium bromide, and/or ammonium sulfate concentration of about 1% to about 3%, or about 2% (w/v) can also be used in the polynucleotide compositions that comprise an organosilicone preparation. In certain embodiments, the polynucleotide compositions can comprise an ammonium salt at a concentration greater or equal to 300 millimolar. In certain embodiments, the polynucleotide compositions that comprise an organosilicone preparation can comprise ammonium sulfate at concentrations from about 80 to about 1200 mM or about 150 mM to about 600 mM.

In certain embodiments, the polynucleotide compositions can also comprise a phosphate salt. Phosphate salts used in the compositions include, but are not limited to, calcium, magnesium, potassium, or sodium phosphate salts. In certain embodiments, the polynucleotide compositions can comprise a phosphate salt at a concentration of at least about 5 millimolar, at least about 10 millimolar, or at least about 20 millimolar. In certain embodiments, the polynucleotide compositions will comprise a phosphate salt in a range of about 1 mM to about 25 mM or in a range of about 5 mM to about 25 mM. In certain embodiments, the polynucleotide compositions can comprise sodium phosphate at a concentration of at least about 5 millimolar, at least about 10 millimolar, or at least about 20 millimolar. In certain embodiments, the polynucleotide compositions can comprise sodium phosphate at a concentration of about 5 millimolar, about 10 millimolar, or about 20 millimolar. In certain embodiments, the polynucleotide compositions will comprise a sodium phosphate salt in a range of about 1 mM to about 25 mM or in a range of about 5 mM to about 25 mM. In certain embodiments, the polynucleotide compositions can comprise a sodium phosphate buffer at a pH of about 6.8.

In certain embodiments, other useful transfer agents or adjuvants to transfer agents that can be used in polynucleotide compositions provided herein include surfactants and/or effective molecules contained therein. Surfactants and/or effective molecules contained therein include, but are not limited to, sodium or lithium salts of fatty acids (such as tallow or tallowamines or phospholipids) and organosilicone surfactants. In certain embodiments, the polynucleotide compositions that comprise a transfer agent are formulated with counter-ions or other molecules that are known to associate with nucleic acid molecules. Illustrative examples include, tetraalkyl ammonium ions, trialkyl ammonium ions, sulfonium ions, lithium ions, and polyamines such as spermine, spermidine, or putrescine. In certain embodiments, the polynucleotide compositions are formulated with a non-polynucleotide herbicide. Non-polynucleotide herbicidal molecules include, but are not limited to, glyphosate, auxin-like benzoic acid herbicides including dicamba, chloramben and TBA, glufosinate, auxin-like herbicides including phenoxy carboxylic acid herbicide, pyridine carboxylic acid herbicide, quinoline carboxylic acid herbicide, pyrimidine carboxylic acid herbicide, and benazolin-ethyl herbicide, sulfonylureas, imidazolinones, bromoxynil, delapon, cyclohezanedione, protoporphyrionogen oxidase inhibitors, and 4-hydroxyphenyl-pyruvate-dioxygenase inhibiting herbicides.

In certain embodiments, the polynucleotides used in the compositions that are essentially identical or essentially complementary to the BI-1 target gene or transcript will comprise the predominant nucleic acid in the composition. Thus in certain embodiments, the polynucleotides that are essentially identical or essentially complementary to the target gene or transcript will comprise at least about 50%, 75%, 95%, 98%, or 100% of the nucleic acids provided in the composition by either mass or molar concentration. However, in certain embodiments, the polynucleotides that are essentially identical or essentially complementary to the target gene or transcript can comprise at least about 1% to about 50%, about 10% to about 50%, about 20% to about 50%, or about 30% to about 50% of the nucleic acids provided in the composition by either mass or molar concentration. Also provided are compositions where the polynucleotides that are essentially identical or essentially complementary to the target gene or transcript can comprise at least about 1% to 100%, about 10% to 100%, about 20% to about 100%, about 30% to about 50%, or about 50% to a 100% of the nucleic acids provided in the composition by either mass or molar concentration.

Polynucleotides comprising ssDNA, dsDNA, ssRNA, dsRNA, or RNA/DNA hybrids that are essentially identical or complementary to certain plant target genes or transcripts and that can be used in compositions containing transfer agents that include, but are not limited to, organosilicone preparations, to suppress those target genes when topically applied to plants are disclosed in co-assigned U.S. patent application Ser. No. 13/042,856. Various polynucleotide herbicidal molecules, compositions comprising those polynucleotide herbicidal molecules and transfer agents that include, but are not limited to, organosilicone preparations, and methods whereby herbicidal effects are obtained by the topical application of such compositions to plants are also disclosed in co-assigned U.S. patent application Ser. No. 13/042,856 (U.S. Patent Application Publication No. 20110296556), and those polynucleotide herbicidal molecules, compositions, and methods are incorporated herein by reference in their entireties. Genes encoding proteins that can provide tolerance to an herbicide and/or that are targets of a herbicide are collectively referred to herein as "herbicide target genes". Herbicide target genes include, but are not limited to, a 5-enolpyruvylshikimate-3-phosphate synthase (EPSPS), a glyphosate oxidoreductase (GOX), a glyphosate decarboxylase, a glyphosate-N-acetyl transferase (GAT), a dicamba monooxygenase, a phosphinothricin acetyltransferase, a 2,2-dichloropropionic acid dehalogenase, an acetohydroxyacid synthase, an acetolactate synthase, a haloarylnitrilase, an acetyl-coenzyme A carboxylase (ACCase), a dihydropteroate synthase, a phytoene desaturase (PDS), a protoporphyrin IX oxygenase (PPO), a hydroxyphenylpyruvate dioxygenase (HPPD), a para-aminobenzoate synthase, a glutamine synthase, a cellulose synthase, a beta tubulin, and a serine hydroxymethyltransferase gene. The effects of applying certain compositions comprising polynucleotides that are essentially identical or complementary to certain herbicide target genes and transfer agents on plants containing the herbicide target genes was shown to be potentiated or enhanced by subsequent application of an herbicide that targets the same gene as the polynucleotide in co-assigned U.S. patent application Ser. No. 13/042,856. For example, compositions comprising polynucleotides targeting the EPSPS herbicide target gene were potentiated by glyphosate in experiments disclosed in co-assigned U.S. patent application Ser. No. 13/042,856.

In certain embodiments of the compositions and methods disclosed herein, the composition comprising a polynucleotide and a transfer agent can thus further comprise a second polynucleotide comprising at least 19 contiguous nucleotides that are essentially identical or essentially complementary to a transcript to a protein that confers resistance to a herbicide. In certain embodiments, the second polynucleotide does not comprise a polynucleotide that is essentially identical or essentially complementary to a transcript encoding a protein of a target plant that confers resistance to said herbicidal molecule. Thus, in a non-limiting embodiment, the second polynucleotide could be essentially identical or essentially complementary to a transcript encoding a protein that confers resistance to a herbicide in a weed (such as an EPSPS encoding transcript) but would not be essentially identical or essentially complementary to a transcript encoding a protein that confers resistance to that same herbicide in a crop plant.

In certain embodiments, the polynucleotide compositions that comprise a transfer agent can comprise glycerin. Glycerin can be provided in the composition at a concentration of about 0.1% to about 1% (w/v or v/v). A glycerin concentration of about 0.4% to about 0.6%, or about 0.5% (w/v or v/v) can also be used in the polynucleotide compositions that comprise a transfer agent.

In certain embodiments, the polynucleotide compositions that comprise a transfer agent can further comprise organic solvents. Such organic solvents include, but are not limited to, DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions).

In certain embodiments, the polynucleotide compositions that comprise a transfer agent can further comprise naturally derived or synthetic oils with or without surfactants or emulsifiers. Such oils include, but are not limited to, plant-sourced oils, crop oils (such as those listed in the 9th Compendium of Herbicide Adjuvants, publicly available on line at www.herbicide.adjuvants.com), paraffinic oils, polyol fatty acid esters, or oils with short-chain molecules modified with amides or polyamines such as polyethyleneimine or N-pyrrolidine.

In some embodiments, methods include one or more applications of the composition comprising a polynucleotide and a transfer agent or one or more effective components contained therein. In certain embodiments of the methods, one or more applications of a transfer agent or one or more effective components contained therein can precede one or more applications of the composition comprising a polynucleotide and a transfer agent. In embodiments where a transfer agent and/or one or more effective molecules contained therein is used either by itself as a pre-treatment or as part of a composition that includes a polynucleotide, embodiments of the polynucleotide molecules are double-stranded RNA oligonucleotides, single-stranded RNA oligonucleotides, double-stranded RNA polynucleotides, single-stranded RNA polynucleotides, double-stranded DNA oligonucleotides, single-stranded DNA oligonucleotides, double-stranded DNA polynucleotides, single-stranded DNA polynucleotides, chemically modified RNA or DNA oligonucleotides or polynucleotides or mixtures thereof.

Compositions and methods described herein are useful for modulating or suppressing the expression of an endogenous BAX inhibitor 1 (BI-1) target gene or transgenic BAX inhibitor 1 (BI-1) target gene in a plant cell or plant. In certain embodiments of the methods and compositions provided herein, expression of BI-1 target genes can be suppressed completely, partially and/or transiently to result in an improvement in fungal disease resistance. In various embodiments, a BAX inhibitor 1 (BI-1) target gene includes coding (protein-coding or translatable) sequence, non-coding (non-translatable) sequence, or both coding and non-coding sequence. Compositions can include polynucleotides and oligonucleotides designed to target multiple BAX inhibitor 1 (BI-1) genes, or multiple segments of one or more BAX inhibitor 1 (BI-1) genes. The target gene can include multiple consecutive segments of a target BAX inhibitor 1 (BI-1) gene, multiple non-consecutive segments of a BAX inhibitor 1 (BI-1) target gene, multiple alleles of a target gene, or multiple BAX inhibitor 1 (BI-1) target genes from one or more species. BAX inhibitor 1 (BI-1) target genes include, but are not limited to, the endogenous BAX inhibitor 1 (BI-1) plant genes of SEQ ID NO: or. BAX inhibitor 1 (BI-1) target genes include, but are not limited to, BAX inhibitor 1 (BI-1) plant genes that encode proteins that are orthologous to the proteins encoded by SEQ ID NO:1, 3, 5, 7, 9, 11, 13, 15, 17, 19, 21, 23, 25, 27, 29, or 31. BAX inhibitor 1 (BI-1) target genes include, but are not limited to, BAX inhibitor 1 (BI-1) plant genes that encode the proteins of SEQ ID NO: 1, 3, 5, 7, 9, 11, 13, 15, 17, 19, 21, 23, 25, 27, 29, or 31.

Target genes and plants containing those target genes can be obtained from: i) row crop plants including, but are not limited to, corn, soybean, cotton, canola, sugar beet, alfalfa, sugarcane, rice, and wheat; ii) vegetable plants including, but not limited to, tomato, potato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra; iii) culinary plants including, but not limited to, basil, parsley, coffee, or tea; iv) fruit plants including but not limited to apple, pear, cherry, peach, plum, apricot, banana, plantain, table grape, wine grape, citrus, avocado, mango, or berry; v) a tree grown for ornamental or commercial use, including, but not limited to, a fruit or nut tree; or, vi) an ornamental plant (e. g., an ornamental flowering plant or shrub or turf grass). The methods and compositions provided herein can also be applied to plants produced by a cutting, cloning, or grafting process (i. e., a plant not grown from a seed) include fruit trees and plants that include, but are not limited to, citrus, apples, avocados, tomatoes, eggplant, cucumber, melons, watermelons, and grapes as well as various ornamental plants. Such row crop, vegetable, culinary, fruit, tree, or ornamental plants improvements in fungal disease resistance that result from suppressing BAX inhibitor 1 (BI-1) gene expression are provided herein. Such row crop, vegetable, culinary, fruit, tree, or ornamental plant parts or processed plant products exhibiting improvements in fungal disease resistance that result from suppressing BAX inhibitor 1 (BI-1) gene expression are also provided herein. Such plant parts can include, but are not limited to, flowers, stems, tubers, fruit, anthers, meristems, ovules, pollen, leaves, or seeds. Such processed plant products obtained from the plant parts can include, but are not limited to, a meal, a pulp, a feed, or a food product.

In some embodiments, a method for modulating or suppressing expression of an BAX inhibitor 1 (BI-1) gene in a plant including (a) conditioning of a plant to permeation by polynucleotides and (b) treatment of the plant with the polynucleotide molecules, wherein the polynucleotide molecules include at least one segment of 18 or more contiguous nucleotides cloned from or otherwise identified from the BAX inhibitor 1 (BI-1) target gene in either anti-sense or sense orientation, whereby the polynucleotide molecules permeate the interior of the plant and induce modulation of the target gene is provided. The conditioning and polynucleotide application can be performed separately or in a single step. When the conditioning and polynucleotide application are performed in separate steps, the conditioning can precede or can follow the polynucleotide application within minutes, hours, or days. In some embodiments more than one conditioning step or more than one polynucleotide molecule application can be performed on the same plant. In embodiments of the method, the segment can be cloned or identified from (a) coding (protein-encoding), (b) non-coding (promoter and other gene related molecules), or (c) both coding and non-coding parts of the BAX inhibitor 1 (BI-1) target gene. Non-coding parts include DNA, such as promoter regions or the RNA transcribed by the DNA that provide RNA regulatory molecules, including but not limited to: introns, 5' or 3' untranslated regions, and microRNAs (miRNA), trans-acting siRNAs, natural anti-sense siRNAs, and other small RNAs with regulatory function or RNAs having structural or enzymatic function including but not limited to: ribozymes, ribosomal RNAs, t-RNAs, aptamers, and riboswitches. In certain embodiments where the polynucleotide used in the composition comprises a promoter sequence essentially identical to, or essentially complementary to at least 18 contiguous nucleotides of the promoter of the endogenous target gene, the promoter sequence of the polynucleotide is not operably linked to another sequence that is transcribed from the promoter sequence.

Compositions comprising a polynucleotide and a transfer agent provided herein can be topically applied to a plant or plant part by any convenient method, e.g., spraying or coating with a powder, or with a liquid composition comprising any of an emulsion, suspension, or solution. Such topically applied sprays or coatings can be of either all or of any a portion of the surface of the plant or plant part. Similarly, compositions that comprise a transfer agent or other pre-treatment can in certain embodiments be applied to the plant or plant part by any convenient method, e. g., spraying or wiping a solution, emulsion, or suspension. Compositions comprising a polynucleotide and a transfer agent provided herein can be topically applied to plant parts that include, but are not limited to, flowers, stems, tubers, meristems, ovules, fruit, anthers, pollen, leaves, or seeds.

Application of compositions comprising a polynucleotide and a transfer agent to seeds is specifically provided herein. Seeds can be contacted with such compositions by spraying, misting, immersion, and the like.

In certain embodiments, application of compositions comprising a polynucleotide and a transfer agent to plants, plant parts, or seeds in particular can provide for an improvement in fungal disease resistance in progeny plants, plant parts, or seeds derived from those treated plants, plant parts, or seeds. In certain embodiments, progeny plants, plant parts, or seeds derived from those treated plants, plant parts, or seeds will exhibit an improvement in an improvement in fungal disease resistance that results from suppressing expression of an BI-1 gene. In certain embodiments, the methods and compositions provided herein can provide for an improvement in an improvement in fungal disease resistance in progeny plants or seeds as a result of epigenetically inherited suppression of BI-1 expression. In certain embodiments, such progeny plants exhibit an improvement in an improvement in fungal disease resistance from epigenetically inherited suppression of BI-1 gene expression that is not caused by a transgene where the polynucleotide is operably linked to a promoter, a viral vector, or a copy of the polynucleotide that is integrated into a non-native location in the chromosomal DNA of the plant. Without seeking to be limited by theory, progeny plants or seeds derived from those treated plants, plant parts, or seeds can exhibit an improvement in an improvement in fungal disease resistance through an epigenetic mechanism that provides for propagation of an epigenetic condition where suppression of BI-1 gene expression occurs in the progeny plants, plant parts, or plant seeds. In certain embodiments, progeny plants or seeds exhibiting an improvement in an improvement in fungal disease resistance as a result of epigenetically inherited suppression of BI-1 gene expression can also exhibit increased methylation, and in particular, increased methylation of cytosine residues, in the endogenous BI-1 gene of the plant. Plant parts, including seeds, of the progeny plants that exhibit an improvement in an improvement in fungal disease resistance as a result of epigenetically inherited suppression of BI-1 gene expression, can also in certain embodiments exhibit increased methylation, and in particular, increased methylation of cytosine residues, in the endogenous BI-1 gene. In certain embodiments, DNA methylation levels in DNA encoding the endogenous BI-1 gene can be compared in plants that exhibit the an improvement in fungal disease resistance and control plants that do not exhibit an improvement in fungal disease resistance to correlate the presence of the an improvement in fungal disease resistance to epigenetically inherited suppression of BI-1 gene expression and to identify plants that comprise the epigenetically inherited improvement in fungal disease resistance.

Various methods of spraying compositions on plants or plant parts can be used to topically apply to a plant surface a composition comprising a polynucleotide that comprises a transfer agent. In the field, a composition can be applied with a boom that extends over the crops and delivers the composition to the surface of the plants or with a boomless sprayer that distributes a composition across a wide area. Agricultural sprayers adapted for directional, broadcast, or banded spraying can also be used in certain embodiments. Sprayers adapted for spraying particular parts of plants including, but not limited to, leaves, the undersides of leaves, flowers, stems, male reproductive organs such as tassels, meristems, pollen, ovules, and the like can also be used. Compositions can also be delivered aerially, such as by a crop dusting airplane. In certain embodiments, the spray can be delivered with a pressurized backpack sprayer calibrated to deliver the appropriate rate of the composition. In certain embodiments, such a backpack sprayer is a carbon dioxide pressurized sprayer with a 11015 flat fan or equivalent spray nozzle with a customized single nozzle assembly (to minimize waste) at a spray pressure of about 0.25 MPa and/or any single nozzle sprayer providing an effective spray swath of 60 cm above the canopy of 3 to 12 inch tall growing plants can be used. Plants in a greenhouse or growth chamber can be treated using a track sprayer or laboratory sprayer with a 11001XR or equivalent spray nozzle to deliver the sample solution at a determined rate. In some embodiments, a non-limiting rate is about 140 L/ha at about 0.25 MPa pressure.

In certain embodiments, it is also contemplated that a plant part can be sprayed with the composition comprising a polynucleotide that comprises a transfer agent. Such plant parts can be sprayed either pre- or post-harvest to provide for an improvement in fungal disease resistance in the plant part that results from suppression of BI-1 gene expression. Compositions can be topically applied to plant parts attached to a plant by a spray as previously described. Compositions can be topically applied to plant parts that are detached from a plant by a spray as previously described or by an alternative method. Alternative methods for applying compositions to detached parts include, but are not limited to, passing the plant parts through a spray by a conveyor belt or trough, or immersing the plant parts in the composition.

Compositions comprising polynucleotides and transfer agents can be applied to plants or plant parts at one or more developmental stages as desired and/or as needed. Application of compositions to pre-germination seeds and/or to post-germination seedlings is provided in certain embodiments. Seeds can be treated with polynucleotide compositions provided herein by methods including, but not limited to, spraying, immersion, or any process that provides for coating, imbibition, and/or uptake of the polynucleotide composition by the seed. Seeds can be treated with polynucleotide compositions using seed batch treatment systems or continuous flow treatment systems. Seed coating systems are at least described in U.S. Pat. Nos. 6,582,516, 5,891,246, 4,079,696, and 4,023,525. Seed treatment can also be effected in laboratory or commercial scale treatment equipment such as a tumbler, a mixer, or a pan granulator. A polynucleotide composition used to treat seeds can contain one or more other desirable components including, but not limited to liquid diluents, binders to serve as a matrix for the polynucleotide, fillers for protecting the seeds during stress conditions, and plasticizers to improve flexibility, adhesion and/or spreadability of the coating. In addition, for oily polynucleotide compositions containing little or no filler, drying agents such as calcium carbonate, kaolin or bentonite clay, perlite, diatomaceous earth or any other adsorbent material can be added. Use of such components in seed treatments is described in U.S. Pat. No. 5,876,739. Additional ingredients can be incorporated into the polynucleotide compositions used in seed treatments. Such ingredients include but are not limited to: conventional sticking agents, dispersing agents such as methylcellulose (Methocel A15LV or Methocel A15C, for example, serve as combined dispersant/sticking agents for use in seed treatments), polyvinyl alcohol (e.g., Elvanol 51-05), lecithin (e.g., Yelkinol P), polymeric dispersants (e.g., polyvinylpyrrolidone/vinyl acetate PVPNA S-630), thickeners (e.g., clay thickeners such as Van Gel B to improve viscosity and reduce settling of particle suspensions), emulsion stabilizers, surfactants, antifreeze compounds (e.g., urea), dyes, colorants, and the like that can be combined with compositions comprising a polynucleotide and a transfer agent. Further ingredients used in compositions that can be applied to seeds can be found in McCutcheon's, vol. 1, "Emulsifiers and Detergents," MC Publishing Company, Glen Rock, N.J., U.S.A., 1996 and in McCutcheon's, vol. 2, "Functional Materials," MC Publishing Company, Glen Rock, N.J., U.S.A., 1996. Methods of applying compositions to seeds and pesticidal compositions that can be used to treat seeds are described in US Patent Application publication 20080092256, which is incorporated herein by reference in its entirety.

Application of the compositions in early, mid-, and late vegetative stages of plant development is provided in certain embodiments. Application of the compositions in early, mid-, and late reproductive stages is also provided in certain embodiments. Application of the compositions to plant parts at different stages of maturation is also provided.

The following examples are included to demonstrate certain embodiments. Those of skill in the art should, in light of the present disclosure, appreciate that many changes can be made in the specific embodiments that are disclosed and still obtain a like or similar result without departing from the spirit and scope of the invention.

EXAMPLES

Example 1. BI-1 Target Gene Sequences

Target BI-1 genes at least occur in the genome of plants provided in Table 2. The BI-1 genes and provided in Table 2 or their corresponding transcripts, can be used as targets of polynucleotide compositions comprising a polynucleotide that of at least 18 contiguous nucleotides that are essentially identical or essentially complementary to those genes or transcripts. The genes and proteins provided in Table 2, or sequences contained within those genes provided herewith in Example 5 can also be used to obtain orthologous BI-1 genes from plants not listed in Table 2. Such orthologous genes and their transcripts can then serve as targets of polynucleotides provided herein or as a source of polynucleotides that are specifically designed to target the orthologous genes or transcripts.

TABLE 2

BAX inhibitor 1 (BI-1) sequences from various plants that are useful targets for topical suppression to control fungal pathogens.

| | | |
|---|---|---|
| SEQ ID NO: 1 | *Arabidopsis thaliana* | *Arabidopsis* BI-1 protein |
| SEQ ID NO: 2 | *Arabidopsis thaliana* | *Arabidopsis* BI-1 gene |
| SEQ ID NO: 3 | *Lactuca sativa* | Lettuce BI-1 protein |
| SEQ ID NO: 4 | *Lactuca sativa* | Lettuce BI-1 gene |
| SEQ ID NO: 5 | Q ID NO: 4; opersicum | Tomato BI-1 protein |
| SEQ ID NO: 6 | *Solanum lycopersicum* | Tomato BI-1 gene |
| SEQ ID NO: 7 | *Vitis vinifera* | Grape BI-1 protein |
| SEQ ID NO: 8 | *Vitis vinifera* | Grape BI-1 gene |
| SEQ ID NO: 9 | *Capsicum annuum* | Pepper BI-1 protein |
| SEQ ID NO: 10 | *Capsicum annuum* | Pepper BI-1 gene |
| SEQ ID NO: 11 | *Glycine max* | Soybean BI-1 protein |
| SEQ ID NO: 12 | *Glycine max* | Soybean BI-1 gene |
| SEQ ID NO: 13 | *Sorghum bicolor* | *Sorghum* BI-1 protein |
| SEQ ID NO: 14 | *Sorghum bicolor* | *Sorghum* BI-1 gene |
| SEQ ID NO: 15 | *Zea mays* | Corn BI-1 protein |
| SEQ ID NO: 16 | *Zea mays* | Corn BI-1 gene |
| SEQ ID NO: 17 | *Triticum aestivum* | Wheat BI-1 protein |
| SEQ ID NO: 18 | *Triticum aestivum* | Wheat BI-1 gene |
| SEQ ID NO: 19 | *Triticum aestivum* | Wheat BI-1 protein |
| SEQ ID NO: 20 | *Triticum aestivum* | Wheat BI-1 gene |
| SEQ ID NO: 21 | *Glycine max* | Soybean BI-2 protein |
| SEQ ID NO: 22 | *Glycine max* | Soybean BI-2 gene |
| SEQ ID NO: 23 | *Hordeum vulgare* | Barley BI-1 protein |
| SEQ ID NO: 24 | *Hordeum vulgare* | Barley BI-1 gene |
| SEQ ID NO: 25 | *Oryza sativa* subsp. *Japonica* | Rice BI-1 protein |
| SEQ ID NO: 26 | *Oryza sativa* subsp. *Japonica* | Rice BI-1 gene |
| SEQ ID NO: 27 | *Cucumis sativus* | BI-1 protein |
| SEQ ID NO: 28 | *Cucumis sativus* | BI-1 gene |
| SEQ ID NO: 29 | *Cucumis sativus* | Cucumber BI-1 protein |
| SEQ ID NO: 30 | *Cucumis sativus* | Cucumber BI-1 gene |
| SEQ ID NO: 31 | *Gossypium hirsutum* | Cotton BI-1 protein |
| SEQ ID NO: 32 | *Gossypium hirsutum* | Cotton BI-1 gene |

Table 2 contains the target BI-1 DNA sequences from the indicated plant species. For each gene having a DNA sequence provided in Table 2, polynucleotides such as single stranded or double stranded DNA or RNA fragments in sense and/or antisense orientation will be mixed with an organosilicone preparation. These compositions will be topically applied to plants to effect expression of the target genes in the specified plant to obtain the plants that exhibit disease resistance. In particular, plants that are resistant to powdery mildew, downy mildew, rust and/or other fungal infections will be obtained through the application of such compositions.

Example 2. Identification of Orthologous BI-1 Genes

The sequences disclosed in SEQ ID NO: 1 through 32, along with the phylogenetic method for functional assignment described above, can be used to efficiently identify and clone BI-1 homologs useful for the control on pathogens causing powdery mildews, downy mildews or rusts, from other plant species not explicitly described here.

Example 3. Polynucleotides that can be Used to Reduce BI-1 Expression in Various Plants Examples of polynucleotides that can be used to reduce expression of BI-1 genes in various plants is provided herewith as SEQ ID NOS: 33-106, 109-140, and 142-146. Other regions of BI-1 genes can also be targeted to modify expression including the use of antisense DNA oligonucleotides against coding regions and/or targeting promoter regions using sense/antisense dsRNA, sense or antisense ssDNA as well as sense/antisense double stranded DNA. For example, a polynucleotide that comprises at least 18 contiguous nucleotides that are essentially identical or essentially complementary to SEQ ID NO: 2, 4, 6, 8, 10, 12, 14, 16, 18, 20, 22, 24, 26, 28, 30, or 32 can be used to downregulate expression of those BI-1 genes.

Example 4. Topical Oligonucleotide Application and Powdery Mildew Testing Methods Barley seeds are planted in 2 inch pots in the greenhouse. Five days later, barley seedlings are sprayed with polynucleotides such as ssDNA and/or dsRNA oligos directed to the promoter and/or targeting the coding region of a target gene of interest. The nucleotide solution applied consists of 6-20 nm of each ssDNA oligonucleotide or 0.5-4 nm dsRNA, 0.1 to 0.3% L77 silwet, 50 mM NaPO$_4$ in a final volume of 40 microliters of water. Two to 4 days post spraying, seedlings will be infected with dry spores of barley powdery mildew (*Blumeria graminis* f. sp. *hordei*) and 7 days post infection, disease development is scored for the percentage of leaf area covered with powdery mildew.

Cucumber seeds are planted in a 3-inch square pot and thinned to one plant per pot after emergence. When the first true leaf is fully expanded and the second leaf is opening, a polynucleotide solution such as ssDNA and/or dsRNA oligos directed to the promoter and/or targeting the coding region of a target gene of interest is applied to the first true leaf or the cotyledons. The nucleotide solution applied consists of 6-20 nm of each ssDNA oligonucleotide or 0.5-4 nm dsRNA, 0.1 to 0.3% L77 Silwet, 50 mM NaPO$_4$ in a final volume of 40 microliters of water. Two days later the entire cucumber plant is inoculated with a shower of dry spores of cucumber powdery mildew (*Sphaerotheca fuliginea*) shaken off diseased plants. Disease severity will be evaluated on the treated leaf and succeeding leaves 10 days later and at subsequent intervals.

Tomato seeds are planted in a 3-inch square pot and thinned to one plant per pot after emergence. Two weeks old tomato seedlings are treated with 6-20 nm of each ssDNA oligonucleotide or 0.5-4 nm dsRNA, 0.2-0.5% L77 silwet, 50 mM NaPO$_4$, 1% ammonium sulfate in a final volume of 30 microliters of water. Two to 4 days post spraying plants are innoculated with dry spores of tomato powdery mildew (*Oidium neolycopersici*) and 13 days post infection, disease development is scored for the percentage of leaf area covered with powdery mildew.

Example 5. Control of Powdery Mildew with Oligonucleotide Applications

Barley plants were treated with control and oligonucleotide containing solutions essentially as indicated in Example 4. More specifically, Barley seeds (Perry variety) are planted about ¼" into soil in 2 inch pots in the growth chamber and grown at 25° C. with a 16 hr light cycle in 50% humidity. Before polynucleotide application the plants are randomized. Application of polynucleotides (either ssDNA oligos and/or dsRNA) is performed by pipet application where 5 µL of solution containing nucleotides is applied to both sides of the first leaf. The nucleotide solution applied consists of ~3-15 nm of each ssDNA oligonucleotide or ~0.5-1 nm dsRNA, 0.1-0.3% Silwet L-77, 5 mM NaPO4, and 1% AMS in Gibco ultra pure water. Two days post treatment seedlings are infected with barley powdery mildew (*Blumeria graminis* f. sp. *hordei*). The growth chamber settings for the infection are as follows: 23° C., with a 12 hr light cycle in 70% humidity. At seven days post infection disease severity is scored for the percentage of leaf area covered with powdery mildew.

Data is analyzed using Anova Single Factor Analysis ($\alpha=0.1$). The ½ A LSD is calculated and custom error bars created for the bar graphs. Percent disease reduction is compared to formulation blank and nucleic acid control Experiments were conducted using pools of polynucleotides from the following Table 3.

TABLE 3

| Polynucleotides | | | | |
|---|---|---|---|---|
| Sequence Type | Sequence name | Sequence | Length | SEQ ID NO: |
| antisense DNA | T5895 | TCAGGGCAATGTGTAGGTAAGCACC | 25 | 93 |
| antisense DNA | T5896 | AGCATTGTCAGCATCCCGCCGATGT | 25 | 94 |
| antisense DNA | T5897 | TTCCAGGAGGGCTGCACCCATCAGC | 25 | 95 |
| antisense DNA | T5898 | CAATCAGAGGTCCAACCGAAGCCCC | 25 | 96 |
| antisense DNA | T5899 | CTTGGGTCAAAGTCTATGGCAAGCT | 25 | 97 |
| antisense DNA | T5900 | TCCGACAAACCCTGTCACGAGGATG | 25 | 98 |
| antisense DNA | T5901 | AGAAGCACCCAAAGGCGATGGCGGT | 25 | 99 |
| antisense DNA | T5902 | CGCTTGGCGATGATGGCGGCGCCAG | 25 | 100 |
| antisense DNA | T5903 | GCCACCGAGGTACAGGTACTCCCTG | 25 | 101 |
| antisense DNA | T5904 | GGATCGACAGGCCAGACGAGAGCAG | 25 | 102 |
| antisense DNA | T5905 | GACGTGACAAACTGCAGCCAGAGCA | 25 | 103 |
| antisense DNA | T5906 | GCTGCCAGAGGAGTGGCCAAAGATG | 25 | 104 |
| antisense DNA | T5907 | GGCCAAAGTAAACCTCAAACATGAA | 25 | 105 |
| antisense DNA | T5908 | ACCATGTACCCCAGGAAGATCAACA | 25 | 106 |
| antisense DNA | T4211 | GGGGTGCTGGAGAGGCCCAGGTGG | 24 | 107 |
| sense | T4211_S | CCACCTGGGCCTCTCCAGCACCCC | 24 | 108 |

TABLE 3-continued

Polynucleotides

| Sequence Type | Sequence name | Sequence | Length | SEQ ID NO: |
|---|---|---|---|---|
| antisense DNA | T5909 | CTCGATGATCTCCTGCGTGTCGTAC | 25 | 109 |
| antisense DNA | T4223A_AS | GACCCCCTCTTCCTCTTCTTCTTG | 24 | 110 |
| antisense DNA | T4223B_AS | CGTTCTTGAGCATGATGATGAGGA | 24 | 111 |
| antisense DNA | T4223C_AS | GCAACAAAGTCGGTGAAGAGG | 21 | 112 |
| antisense DNA | T4223D_AS | GTCAGCATCCCGCCGATGTTCAG | 23 | 113 |
| antisense DNA | T4223E_AS | CCACGGCAGATGAGGCCAGTGCA | 23 | 114 |
| antisense DNA | T4223F_AS | TAAACGAGCTTGAGGTGGGACTG | 23 | 115 |
| antisense DNA | T4223G_AS | AACTGCAGCCAGAGCAGGATCG | 22 | 116 |
| antisense DNA | T4223H_AS | AGCAGGCCACCGAGGTACAGGT | 22 | 117 |
| antisense DNA | T4223I_AS | GGCGGCGCCAGAGAAGCACCC | 21 | 118 |
| dsRNA | T5942 | ATGGACGCCTTCTACTCGACCTCGTC GGCGGCGGCGAGCGGCTGGGGCCA CGACTCCCTCAAGAACTTCCGCCAGA TCTCCCCCGCCGTGCAGTCCCACCTC AAGCTCGTTTACCTGACTCTATGCTTT GCACTGGCCTCATCTGCCGTG | 150 | 119 |
| dsRNA | T5943 | AGGGCGCACCATGGCGACATGGACT ACATCAAGCACGCCCTCACCCTCTTC ACCGACTTTGTTGCCGTCCTCGTCCG AGTCCTCATCATCATGCTCAAGAACG CAGGCGACAAGTCGGAGGACAAGA AGAAGAGGAAGAGGGGGTCCTGA | 150 | 120 |
| dsRNA | T5944 | CGCTTGTGTCGGAACTATCGCCTGGA TGTTCTCGGTGCCAGTCTATGAGGAG AGGAAGAGGTTTGGGCTGCTGATGG GTGCAGCCCTCCTGGAAGGGGCTTC GGTTGGACCTCTGATTGAGCTTGCCA TAGACTTTGACCCAAGCATCCT | 150 | 121 |

Table 4 provides a summary of the results obtained.

TABLE 4

Powdery Mildew control results
Anova: Single Factor
SUMMARY

| Groups | Oligos in pool | Count | Sum | Average Percent Disease Area | Variance |
|---|---|---|---|---|---|
| Non Treated | | 10 | 256 | 25.6 | 480.2667 |
| Blank | | 10 | 321 | 32.1 | 405.2111 |
| MLO_T4211[1] | SEQ ID NO: 107 | 10 | 6 | 0.6 | 0.266667 |
| BI1_T5895-98 | SEQ ID NO: 93, 94, 95, 96 | 10 | 14 | 1.4 | 1.6 |
| BI1_T5899-02 | SEQ ID NO: 97, 98, 99, 100 | 10 | 31 | 3.1 | 14.98889 |
| BI1_T5903-06 | SEQ ID NO: 101, 102, 103, 104 | 10 | 42 | 4.2 | 56.17778 |
| BI1_T5907-09 | SEQ ID NO: 105, 106, 109 | 10 | 78 | 7.8 | 52.17778 |

[1] A positive control oligonucleotide that suppresses the endogenous barley Mildew Resistance Locus O (MLO) gene and provides fungal disease control.

Example 6. Topical Oligonucleotide Application and Nematode Testing Methods

Application of Oligonucleotides to Seeds for Nematode Control

Cucumber seeds are soaked approximately 5-72 hours in nucleotides, either ssDNA and/or dsRNA oligos directed to the promoter and/or the coding region of a target of interest. Optionally, seeds can be soaked in water for a few hours prior to soaking in oligonucleotide solution. Soaking solution consists of 20 nm of each ssDNA nucleotide or 0.03-1 nm dsRNA, 0.1% silwet L77, 50 mM NaPO4 in a final volume 200 uL in water. The radicals of the cucumber seeds emerge within 72 hours, after which the seeds are placed on germination paper until root length is approximately 2 inches. Seedlings are transplanted to sand vials for RKN inoculation 24 hours later. Ten mL dry sand is added to each vial and seedlings are planted by tilting the vial and laying the seedling in the correct orientation so that the cotyledons are just above the sand and then tilting back to cover the radicles with sand. 3.3 ml water is added to each vial and the vials placed in racks under fluorescent light banks. 500 vermiform eggs or 300 J2 RKN are inoculated in each tube in 50 uL of deionized or spring water. Harvest of the cucumber plants is performed 10 to 12 days after inoculation by washing sand off the roots. A root gall rating and visual phytotoxicity rating is assigned using the following scales: Gall rating scale (Gall: % root mass galled): 0=0-5%; 1=6-20%; 2=21-50%; and 3=51-100%. The average of the triplicate gall rating is then calculated: no galls=0.00-0.33; mild galling=0.67-1.33; moderate galling=1.67-2.33; severe galling=2.67-3.00. Visual phytotoxicity scale is also assigned (Vis. tox; visual reduction in root mass compared to the control): rs1=mild stunting; rs2=moderate stunting; rs3=severe stunting.

Experiments in soybeans using soy cyst nematodes (SCN) are similar to RKN assays except for the following changes. After 5-72 hours of soaking soybean seeds are planted in 100% sand in two inch square plastic pots. Optionally, seeds are soaked in water for a few hours prior to soaking in oligonucleotide solution. Seven days after planting the soybean seed, the nematode soybean cyst nematode (SCN) inoculum (1000 vermiform eggs or 1000 J2s) are applied to the pot. Watering of the test plants is then restricted to only water as needed to prevent wilt for a period of 24 hours. After the 24 hour restricted watering, normal sub-irrigation watering is done for the duration of the test. Twenty eight days after inoculation the test is harvested and cysts counted.

Experiments in corn using lesion nematodes are similar to above except for the following changes. After 5-72 hours of soaking, corn seeds are planted in a sand:Turface mix 2:1 in 4 inch deep pots (Turface™ MVP, Profile Products, LLC., Buffalo Grove, Ill.). Optionally, seeds are soaked in water for a few hours prior to soaking in oligonucleotide solution. Inoculum of 2 gm of roots *P. scribneri* infested corn roots are applied to seedings and removed from the pot after 7 days. Watering of the test plants is then restricted to only water as needed to prevent wilt for a period of 24 hours after inoculation. After the 24 hour restricted watering, normal sub-irrigation watering as needed is done for the duration of the test. 12-14 days post inoculation, plants are harvested and nematodes extracted for 6 days from the cut up roots in a mist tent.

RKN and SCN J2s are prepared from hatchbowls using the following solutions: RKN solution: 1 L aerated tap water, 1 ml of 50 mg/ml kanamycin, 0.5 ml of 20 mg/ml imazalil sulfate; SCN solution: 1 L aerated tap water, 1 ml of 50 mg/ml kanamycin, 0.5 ml of 20 mg/ml imazalil sulfate, 1430 mg zinc sulfate.

Hatchbowls are autoclaved 6 oz bowls, lined with screen mesh and paper filter. Approximately 20 ml of appropriate hatch solution is poured into each bowl. Eggs are then place in the bowls and covered with foil. The bowls are then placed in a 25° C. incubator overnight. The next day the hatched J2's are extracted, additional solution added as needed and replaced in the incubator. Each bowl is used for 2 weeks and then disposed.

Example 7. Protection of Soybean from Soy Cyst Nematode (SCN)

Soybean cotyledons of the variety W82 were treated with the treatments indicated in Table 5 by topical application of the oligonucleotide solution in 5 mM NaPO$_4$, 1% Ammonium Sulfate, and 0.20% Silwet™ (wt percent). Approximately 50 μl of solution containing the ssDNA oligonucleotides of Table 6, in pools of 4 ssDNAs/pool, was applied to each cotyledon of the plants and 4 plants were subjected to each treatment. One day following treatment, the plants were infected with approximately 1000 vermiform eggs of Soy Cyst Nematode applied directly to the pot. Twenty eight days after inoculation the root weights and cyst counts were recorded. ANOVA analysis for cyst count is provided in Table 8 and root weight is in Table 10. FIG. 1 shows the bar chart for cyst count and root weight.

TABLE 5

| | Treatments | |
|---|---|---|
| Treatment # | Description | Oligo Final Conc. |
| 1 | Bi1-1 pool 1 AS coding | 80 nmol/4 × 10 μL |
| 2 | Bi1-1 pool 2 AS coding | 80 nmol/4 × 10 μL |
| 3 | Bi1-1 pool 3 AS coding | 80 nmol/4 × 10 μL |
| 4 | Bi 1-2 pool 4 AS coding | 80 nmol/4 × 10 μL |
| 5 | Bi1-2 pool 5 AS coding | 80 nmol/4 × 10 μL |
| 6 | GFP AS control | 80 nmol/4 × 10 μL |
| 7 | Mock treated no Silwet L-77 | |
| 8 | Formulation | |

TABLE 6

| | Oligonucleotides used | | |
|---|---|---|---|
| SEQ ID NO | Sequence | Maps to | Pool ID |
| 122 | TTGAATCGAAGAAGGAATTGAAGGAGTCCAT | Soybean Bi1-1 SEQ ID NO 12 | 1 |
| 123 | AGGTAAGCCCCAACAGCCGCAGCAACCA | Soybean Bi1-1 SEQ ID NO 12 | 1 |
| 124 | CTCTTTTCCTCTCTTCAAAAGGAGGTGTC | Soybean Bi1-1 SEQ ID NO 12 | 1 |
| 125 | TGCACTAAAGATAAGGCTTGGATCGAT | Soybean Bi1-1 SEQ ID NO 12 | 1 |
| 126 | ATCCAGAAGAAACCAAGCCACCAAGGT | Soybean Bi1-1 SEQ ID NO 12 | 2 |
| 127 | CCTACAAACACCAAAAGCCCAAAGTAC | Soybean Bi1-1 SEQ ID NO 12 | 2 |
| 128 | ACTGCAACCAAATCGGTAAACAAGGTCAA | Soybean Bi1-1 SEQ ID NO 12 | 2 |
| 129 | TCAATCTCTCCTCTTCTTTTTCTTC | Soybean Bi1-1 SEQ ID NO 12 | 2 |
| 130 | TCAAGGGACCAACGAAGGCTAATTTCG | Soybean Bi1-1 SEQ ID NO 12 | 3 |
| 131 | GGCTTTGAATTTCAACACCCCTAATT | Soybean Bi1-1 SEQ ID NO 12 | 3 |

TABLE 6-continued

Oligonucleotides used

| SEQ ID NO | Sequence | Maps to | Pool ID |
|---|---|---|---|
| 132 | GCTTGCAATCGGAGAAACACAAATTT | Soybean Bi1-1 SEQ ID NO 12 | 3 |
| 133 | ATGGGGACTTGAAGAAAGTGTCCAT | Soybean Bi1-2 SEQ ID NO 22 | 4 |
| 134 | TAAAATAAACCAGTTTGATGTGATTCTG | Soybean Bi1-2 SEQ ID NO 22 | 4 |
| 135 | TGCTCCCAATGGAAGCCACCGTGGTGA | Soybean Bi1-2 SEQ ID NO 22 | 4 |
| 136 | AATCAGAGGTCCAATGGAAGCACCCTGA | Soybean Bi1-2 SEQ ID NO 22 | 4 |
| 137 | GCCTTGCAACTAAGGCTACTGCAGAAAA | Soybean Bi1-2 SEQ ID NO 22 | 5 |
| 138 | AGAGCTATAGAGCCCCCAAAGAGAGAGG | Soybean Bi1-2 SEQ ID NO 22 | 5 |
| 139 | TCCAGGTCACCAAAGTGAGCCCTCTCA | Soybean Bi1-2 SEQ ID NO 22 | 5 |
| 140 | CTTCTCATTTCTCTTAGATGAATTATT | Soybean Bi1-2 SEQ ID NO 22 | 5 |
| 141 | GTTGTAGTTGTACTCCATCTTATTG | GFP Control | |

TABLE 7

Cyst counts

| trt# | rep1 | rep2 | rep3 | rep4 | avg |
|---|---|---|---|---|---|
| 1 | 143.0 | 109.0 | 90.0 | 111.0 | 113.3 |
| 2 | 42.0 | 46.0 | 44.0 | 31.0 | 40.8 |
| 3 | 78.0 | 197.0 | 193.0 | 101.0 | 142.3 |
| 4 | 138.0 | 75.0 | 80.0 | 51.0 | 86.0 |
| 5 | 141.0 | 136.0 | 92.0 | 107.0 | 119.0 |
| 6 | 72.0 | 67.0 | 75.0 | 95.0 | 77.3 |
| 7 | 83.0 | 128.0 | 52.0 | 103.0 | 91.5 |
| 8 | 179.0 | 122.0 | 165.0 | 184.0 | 162.5 |

TABLE 8

ANOVA Single Factor analysis of Cyst counts

Anova: Single Factor
SUMMARY

| Groups | Count | Sum | Average | Variance |
|---|---|---|---|---|
| Row 1 | 4 | 453 | 113.25 | 482.9167 |
| Row 2 | 4 | 163 | 40.75 | 44.91667 |
| Row 3 | 4 | 569 | 142.25 | 3800.917 |
| Row 4 | 4 | 344 | 86 | 1362 |
| Row 5 | 4 | 476 | 119 | 548.6667 |
| Row 6 | 4 | 309 | 77.25 | 150.9167 |
| Row 7 | 4 | 366 | 91.5 | 1032.333 |
| Row 8 | 4 | 650 | 162.5 | 793.6667 |

ANOVA

| Source of Variation | SS | df | MS | F | P-value | F crit |
|---|---|---|---|---|---|---|
| Between Groups | 41568.88 | 7 | 5938.411 | 5.782054 | 0.000521 | 2.422629 |
| Within Groups | 24649 | 24 | 1027.042 | | | |
| Total | 66217.88 | 31 | | | | |
| std of diff | 22.6 | | df = 1.711 | | | |
| lsd | 38.8 | | | | | |
| ½ lsd | 19.4 | | | | | |

TABLE 9

Root Weight

| trt# | rep1 | rep2 | rep3 | rep4 | avg |
|---|---|---|---|---|---|
| 1 | 16.0 | 18.4 | 14.8 | 18.8 | 17.0 |
| 2 | 13.5 | 16.7 | 18.6 | 4.0 | 13.2 |
| 3 | 5.6 | 15.1 | 11.7 | 10.5 | 10.7 |
| 4 | 14.8 | 14.1 | 12.6 | 12.4 | 13.5 |
| 5 | 12.9 | 13.1 | 14.1 | 12.4 | 13.1 |
| 6 | 15.8 | 17.0 | 19.8 | 16.9 | 17.4 |
| 7 | 15.6 | 15.1 | 14.0 | 11.5 | 14.1 |
| 8 | 14.2 | 16.2 | 17.2 | 14.8 | 15.6 |

TABLE 10

ANOVA analysis of root weight

Anova: Single Factor
SUMMARY

| Treatment | Count | Sum | Average | Variance |
|---|---|---|---|---|
| 1 | 4 | 68 | 17 | 3.68 |
| 2 | 4 | 52.8 | 13.2 | 42.04667 |
| 3 | 4 | 42.9 | 10.725 | 15.46917 |
| 4 | 4 | 53.9 | 13.475 | 1.355833 |
| 5 | 4 | 52.5 | 13.125 | 0.509167 |
| 6 | 4 | 69.5 | 17.375 | 2.909167 |
| 7 | 4 | 56.2 | 14.05 | 3.336667 |
| 8 | 4 | 62.4 | 15.6 | 1.84 |

ANOVA

| Source of Variation | SS | df | MS | F | P-value | F crit |
|---|---|---|---|---|---|---|
| Between Treatm. | 138.1888 | 7 | 19.74125 | 2.219781 | 0.068719 | 2.422629 |
| Within Treatment | 213.44 | 24 | 8.893333 | | | |
| Total | 351.6288 | 31 | | | | |
| std of diff | 2.1 | | df = 1.711 | | | |
| lsd | 3.6 | | | | | |
| ½ lsd | 1.8 | | | | | |

Example 8. Protection of Cucumber from Root Knot Nematode (RKN)

Cucumber seed were soaked for 72 hr in dsRNA polynucleotide solution directed to the coding sequence of soybean Bi-1 gene. Soaking solution consisted of 0.01-1 nm dsRNA, 0.2% Silwet L77, 20 mM NaPO4 in a final volume 200 uL in water as outlined in Table 11. The radicals of the cucumber seeds emerged within 72 hours, after which the seeds were placed on germination paper until root length was approximately 2 inches. Seedlings were transplanted to sand vials for RKN inoculation 24 hours later. Ten mL dry sand was added to each vial and seedlings were planted by tilting the vial and laying the seedling in the correct orientation so that the cotyledons were just above the sand and then tilting back to cover the radicles with sand. 3.3 ml water was added to each vial and the vials placed in racks under fluorescent light banks. 500 vermiform eggs or 300 J2 RKN were inoculated in each tube in 50 uL of deionized or spring water. Harvest of the cucumber plants was performed 10 to 12 days after inoculation by washing sand off the roots.

A root gall rating and visual phytotoxicity rating was assigned using the following scales: Gall rating scale (Gall: % root mass galled): 0=0-5%; 1=6-20%; 2=21-50%; and 3=51-100%. The average of the triplicate gall rating was then calculated: no galls=0.00-0.33; mild galling=0.67-1.33; moderate galling=1.67-2.33; severe galling=2.67-3.00. Table 11 summarizes the treatments performed and Table 12 shows the gall rating results. These results are also graphically displayed in FIG. 2.

TABLE 11

Treatments

| Treatment# | Trigger type | Trigger | SEQ ID NOs | Conc (nmol/μL) | Volume of each dsRNA |
|---|---|---|---|---|---|
| 1 | dsRNA | Bi-1 0.06 nmol (0.012 nmol each) | 142 143 144 145 146 | 0.0172 0.022 0.0148 0.0195 0.0216 | 0.70 0.55 0.81 0.62 0.56 |
| 2 | dsRNA | Bi-1 0.15 nmol (0.03 nmol each) | 142 143 144 145 146 | 0.0172 0.022 0.0148 0.0195 0.0216 | 1.74 1.36 2.03 1.54 1.39 |
| 3 | dsRNA | GFP control 0.06 nmol | 147 | 0.0157 | 3.82 |
| 4 | dsRNA | GFP control 0.15 nmol | 147 | 0.0157 | 9.55 |
| 5 | Mock, no Silwet | | | | |
| 6 | Formulation | | | | |

TABLE 12

RKN Assay Results

| Treatment No. | Treatment | Score % | | | | AVG | St Dev |
|---|---|---|---|---|---|---|---|
| 1 | Bax1 dsRNA coding .06 nmol (.012 nmol each) | 15 | 25 | 10 | 10 | 15 | 7.071067812 |
| 2 | Bax1 dsRNA coding .15 nmol (0.03 nmol each) | 10 | 40 | 5 | 20 | 18.76 | 15.47847968 |
| 3 | GFP dsRNA control .06 nmol | 15 | 40 | 50 | 20 | 31.25 | 16.52 |
| 4 | GFP dsRNA control .15 nmol | 50 | 65 | | | 57.50 | 10.61 |
| 5 | Mock no silwet | 25 | 50 | 40 | 40 | 38.75 | 10.31 |
| 6 | Formulation | 50 | 30 | 70 | 30 | 45 | 19.15 |

What is claimed is:

1. A method for producing a soybean plant exhibiting an improvement in Soy Cyst Nematode (SCN) resistance, the method comprising topically applying to a plant surface a composition that comprises:

(a) at least four polynucleotides that comprise: (i) a polynucleotide of 25 to 150 nucleotides in length that comprises a segment of 25 contiguous nucleotides that are identical or complementary to SEQ ID NO: 126; (ii) a polynucleotide of 25 to 150 nucleotides in length that comprises a segment of 25 contiguous nucleotides that are identical or complementary to SEQ ID NO: 127; (iii) a polynucleotide of 25 to 150 nucleotides in length that comprises a segment of 25 contiguous nucleotides that are identical or complementary to SEQ ID NO: 128; and (iv) a polynucleotide of 25 to 150 nucleotides in length that comprises a segment of 25 contiguous nucleotides that are identical or complementary to SEQ ID NO: 129, wherein said polynucleotides are polynucleotide is not operably linked to a promoter or a viral vector and wherein said polynucleotides are not integrated into the plant chromosome; and (b) a transfer agent; and thereby producing a soybean plant that exhibits an improvement in SCN resistance resulting from suppression of a BAX inhibitor 1 (BI-1) gene.

2. The method of claim 1, wherein said polynucleotides comprise sense ssDNA, sense ssRNA, dsRNA, dsDNA, a double stranded DNA/RNA hybrid, anti-sense ssDNA, or anti-sense ssRNA.

3. The method of claim 1, wherein said composition further comprises a non-polynucleotide herbicidal molecule, a polynucleotide herbicidal molecule, a polynucleotide that suppresses an herbicide target gene, an insecticide, a fungicide, a nematocide, or a combination thereof.

4. The method of claim 1, wherein said composition further comprises a non-polynucleotide herbicidal molecule and said plant is resistant to said non-polynucleotide herbicidal molecule.

5. The method of claim 1, wherein said transfer agent comprises an organosilicone preparation.

* * * * *